United States Patent
Wang

(10) Patent No.: US 10,144,767 B2
(45) Date of Patent: Dec. 4, 2018

(54) ANTI-MICROBIAL PEPTIDES AND COATINGS

(71) Applicant: Board of Regents of the University of Nebraska, Lincoln, NE (US)

(72) Inventor: Guangshun Wang, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 15/680,429

(22) Filed: Aug. 18, 2017

(65) Prior Publication Data

US 2018/0051061 A1 Feb. 22, 2018

Related U.S. Application Data

(60) Provisional application No. 62/376,514, filed on Aug. 18, 2016.

(51) Int. Cl.
| | | |
|---|---|---|
| C07K 14/47 | (2006.01) | |
| A61K 38/17 | (2006.01) | |
| C07K 7/06 | (2006.01) | |
| C07K 7/08 | (2006.01) | |
| A61K 45/06 | (2006.01) | |
| A61K 38/00 | (2006.01) | |
| C12N 15/09 | (2006.01) | |

(52) U.S. Cl.
CPC .......... *C07K 14/4723* (2013.01); *A61K 38/17* (2013.01); *A61K 45/06* (2013.01); *C07K 7/06* (2013.01); *C07K 7/08* (2013.01); *C12N 15/09* (2013.01); *A61K 38/00* (2013.01)

(58) Field of Classification Search
CPC ............ A61K 2039/53; A61K 2039/54; A61K 39/00; A61K 39/092; A61K 38/00; C07K 14/3156; C07K 14/415; C07K 14/47; C07K 14/605; C07K 7/06; C07K 7/08; G01N 33/56944; G01N 2333/7051; G01N 2800/52; G01N 2800/56; G01N 33/57484; C12N 15/8273; C12N 15/8271; A47J 31/56; B01D 17/0214; C11B 13/00; C12Q 1/18; E01B 9/36; H01Q 1/10; H05H 13/00; Y02W 30/74; Y10T 137/7306; Y10T 403/32426; Y10T 403/32501

See application file for complete search history.

(56) References Cited

U.S. PATENT DOCUMENTS

| | | |
|---|---|---|
| 7,465,784 B2 | 12/2008 | Wang |
| 7,985,836 B2 | 7/2011 | Wang |
| 8,722,616 B2 | 5/2014 | Wang |
| 9,580,472 B2 | 2/2017 | Wang |
| 2014/0206016 A1* | 7/2014 | Lozano Sanchez ..... C12Q 1/04 435/7.1 |
| 2015/0259382 A1 | 9/2015 | Wang |

OTHER PUBLICATIONS

Mishra, B., et al., "Anti-Staphylococcal Biofilm Effects of Human Cathelicidin Peptides" ACS Med. Chem. Lett. (2016) 7:117-121.

Mishra, B., et al., "Titanium surfaces immobilized with the major antimicrobial fragment FK-16 of human cathelicidin LL-37 are potent against multiple antibiotic-resistant bacteria" Biofouling (2017) 33(7):544-555.

Mishra, B., et al., "Design and surface immobilization of short anti-biofilm peptides" Acta Biomaterialia (2017) 49:316-328.

Wang, G., et al., "Antimicrobial Peptides in 2014" Pharmaceuticals (2015) 8:123-150.

Zarena, D., et al. "The pi Configuration of the WWW Motif of a Short Trp-Rich Peptide Is Critical for Targeting Bacterial Membranes, Disrupting Preformed Biofilms, and Killing Methicillin-Resistant *Staphylococcus aureus*" Biochemistry (2017) 56:4039-4043.

Wang, G., et al., "APD3: the antimicrobial peptide database as a tool for research and education" Nucleic Acids Research (2016) 44:D1087-D1093.

Wang, G., "Database-Guided Discovery of Potent Peptides to Combat HIV-1 or Superbugs" Pharmaceuticals (2013) 6:728-758.

Wang, G., "Human Antimicrobial Peptides and Proteins" Pharmaceuticals (2014) 7:545-594.

Wang, G., et al., "Correlation of Three-dimensional Structures with the Antibacterial Activity of a Group of Peptides Designed Based on a Nontoxic Bacterial Membrane Anchor" J. Biol. Chem. (2005) 280(7):5803-5811.

Li, X , et al., "Solution Structures of Human LL-37 Fragments and NMR-Based Identification of a Minimal Membrane-Targeting Antimicrobial and Anticancer Region" J. Am. Chem. Soc. (2006) 128:5776-5785.

Wang, G., "Structures of Human Host Defense Cathelicidin LL-37 and Its Smallest Antimicrobial Peptide KR-12 in Lipid Micelles" J. Biol. Chem. (2008) 283(47):32637-32643.

Menousek, J., et al., "Database screening and in vivo efficacy of antimicrobial peptides against meticillin-resistant *Staphylococcus aureus* USA300" Int. J. Antimicrob. Agents (2012) 39(5):402-406.

Mishra, B., et al., "Ab Initio Design of Potent Anti-MRSA Peptides based on Database Filtering Technology" J. Am. Chem. Soc. (2012) 134(30):12426-12429.

Abbassi, F., et al., "Temporin-SHf, a New Type of Phe-rich and Hydrophobic Ultrashort Antimicrobial Peptide" J. Biol. Chem. (2010) 285(22):16880-16892.

Yau, W.M., et al., "The Preference of Tryptophan for Membrane Interfaces" Biochemistry (1998) 37:14713-14718.

Wang, G., et al., "Conformations of Human Apolipoprotein E(263-286) and E(267-289) in Aqueous Solutions of Sodium Dodecyl Sulfate by CD and 1H NMR" Biochemistry (1996) 35:10358-10366.

Khandelia, H., et al., "Cation—π Interactions Stabilize the Structure of the Antimicrobial Peptide Indolicidin near Membranes: Molecular Dynamics Simulations" J. Phys. Chem. B (2007) 111(1):242-250.

(Continued)

*Primary Examiner* — Sarvamangala Devi
(74) *Attorney, Agent, or Firm* — Robert C. Netter, Jr.; Dann, Dorfman, Herrell & Skillman, P.C.

(57) ABSTRACT

Antimicrobial peptides and methods of use are provided.

24 Claims, 19 Drawing Sheets

Specification includes a Sequence Listing.

(56) References Cited

OTHER PUBLICATIONS

Mishra, B., et al., "Small lipopeptides possess anti-biofilm capability comparable to daptomycin and vancomycin" RSC Adv. (2015) 5(73):59758-59769.

Wang, G., et al., "Transformation of Human Cathelicidin LL-37 into Selective, Stable, and Potent Antimicrobial Compounds" ACS Chem. Biol. (2014) 9:1997-2002.

Chan, D.I., et al., "Tryptophan- and arginine-rich antimicrobial peptides: Structures and mechanisms of action" Biochimica et Biophysica Acta (2006) 1758:1184-1202.

Blondelle, S.E., et al., "The antimicrobial activity of hexapeptides derived from synthetic combinatorial libraries" J. Appl. Bacter. (1995) 78:39-46.

Boman, H.G., et al., "Antibacterial peptides: basic facts and emerging concepts" J. Internal Med. (2003) 254:197-215.

Hancock, R.E.W., et al., "Antimicrobial and host-defense peptides as new anti-infective therapeutic strategies" Nat. Biotech. (2006) 24(12):1551-1557.

Wang, G., et al., "Identification of Novel Human Immunodeficiency Virus Type 1—Inhibitory Peptides Based on the Antimicrobial Peptide Database" Antimicrob. Agents Chemotherapy (2010) 54:1343-1346.

Chen, X., et al., "Antimicrobial GL13K Peptide Coatings Killed and Ruptured the Wall of *Streptococcus gordonii* and Prevented Formation and Growth of Biofilms" PLoS ONE (2014) 9(11):e111579.

Godoy-Gallardo, M., et al., "Antibacterial Properties of hLf1-11 Peptide onto Titanium Surfaces: A Comparison Study Between Silanization and Surface Initiated Polymerization" Biomacromolecules (2015) 16:483-496.

Wang, G., et al., "High-quality 3D structures shine light on antibacterial, anti-biofilm and antiviral activities of human cathelicidin LL-37 and its fragments" Biochimica et Biophysica Acta (2014) 1838:2160-2172.

Gabriel, M., et al., "Preparation of LL-37-Grafted Titanium Surfaces with Bactericidal Activity" Bioconjugate Chem. (2006) 17:548-550.

Mishra, B., et al., "Site specific immobilization of a potent antimicrobial peptide onto silicone catheters: evaluation against urinary tract infection pathogens" J. Mater. Chem. B (2014) 2:1706-1716.

Wang, G., et al., "Decoding the Functional Roles of Cationic Side Chains of the Major Antimicrobial Region of Human Cathelicidin LL-37" Antimicrob. Agents Chemotherapy (2012) 56:845-856.

Rozek, A., "Structure of the Bovine Antimicrobial Peptide Indolicidin Bound to Dodecylphosphocholine and Sodium Dodecyl Sulfate Micelles" Biochemistry (2000) 39:15765-15774.

Schibli, D.J., et al., "Structure of the Antimicrobial Peptide Tritrpticin Bound to Micelles: A Distinct Membrane-Bound Peptide Fold" Biochemistry (1999) 38:16749-16755.

Wang, G., "Determination of solution structure and lipid micelle location of an engineered membrane peptide by using one NMR experiment and one sample" Biochimica et Biophysica Acta (2007) 1768:3271-3281.

Schmidtchen, et al., "Boosting Antimicrobial Peptides by Hydrophobic Oligopeptide End Tags" J. Biol. Chem. (2009) 284(26):17584-17594.

* cited by examiner

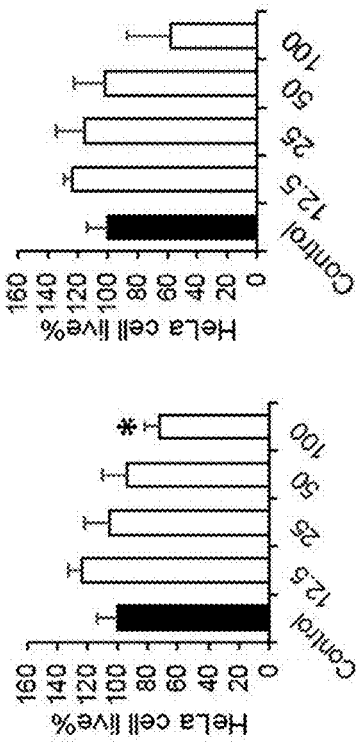
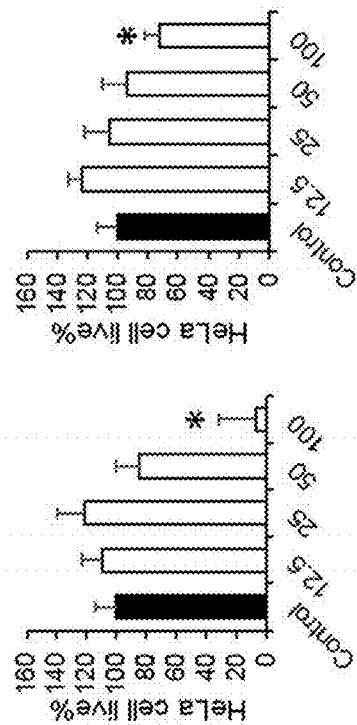
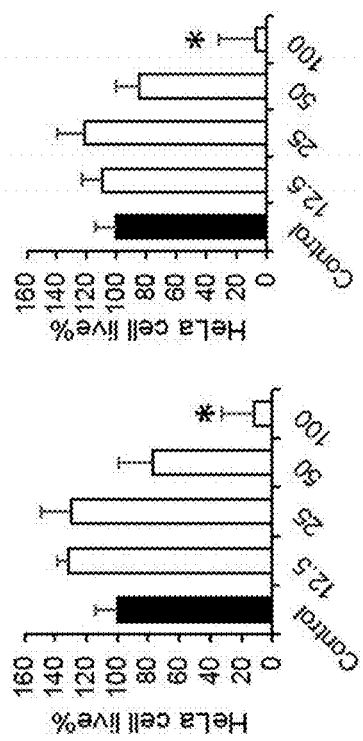
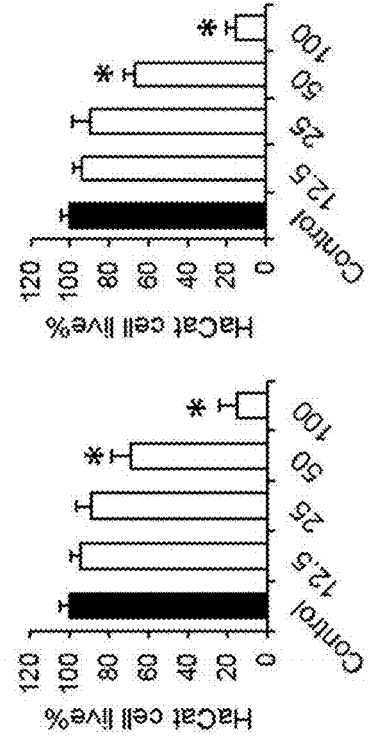
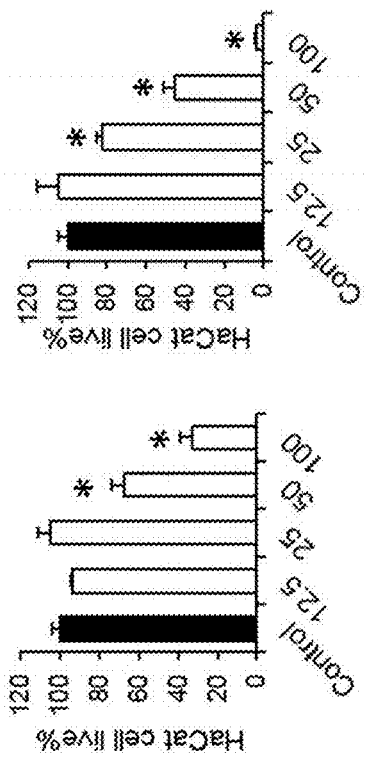

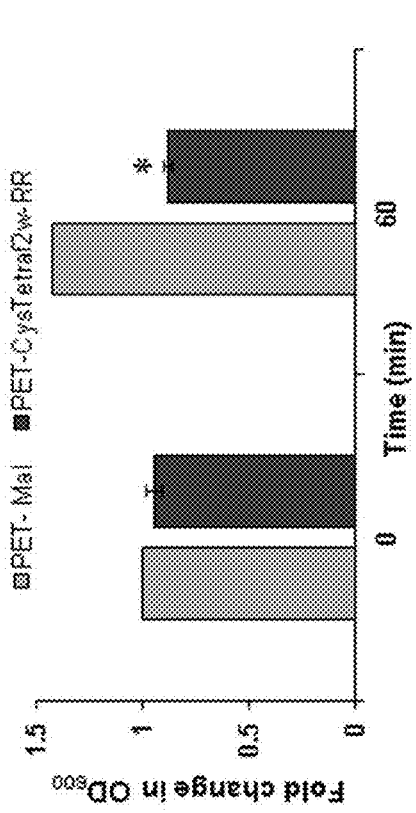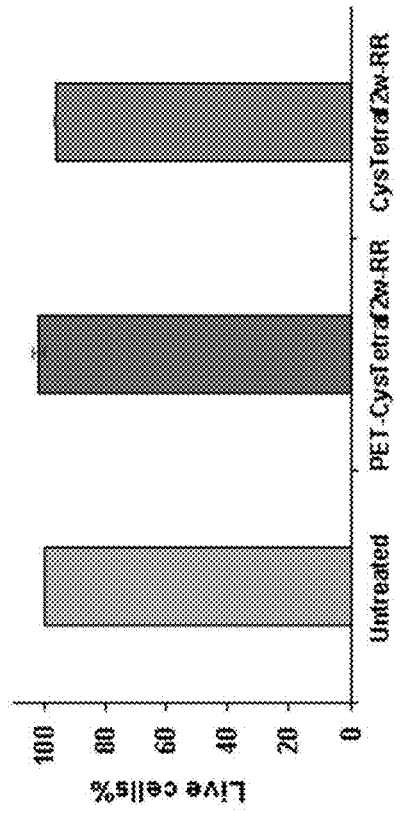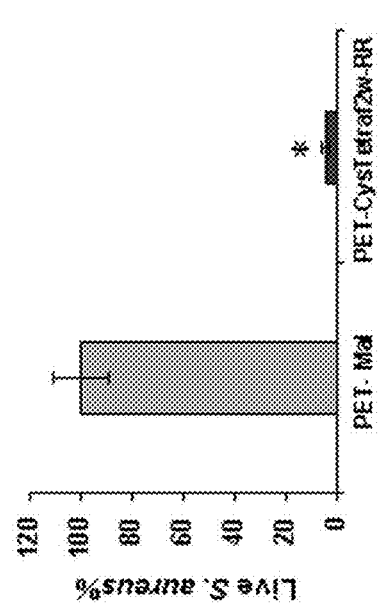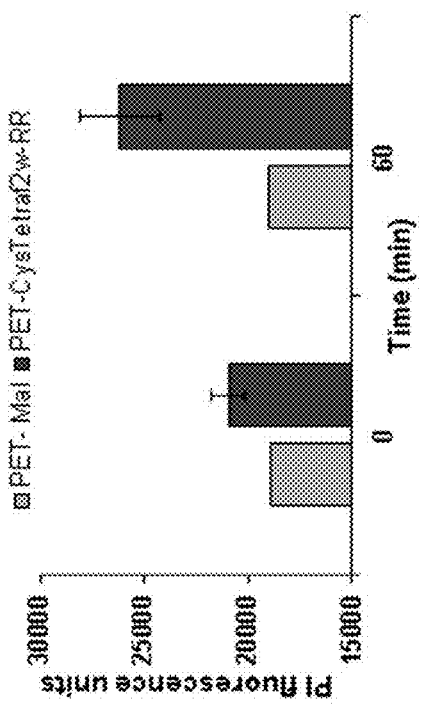
Figure 7A
Figure 7B
Figure 7C
Figure 7D

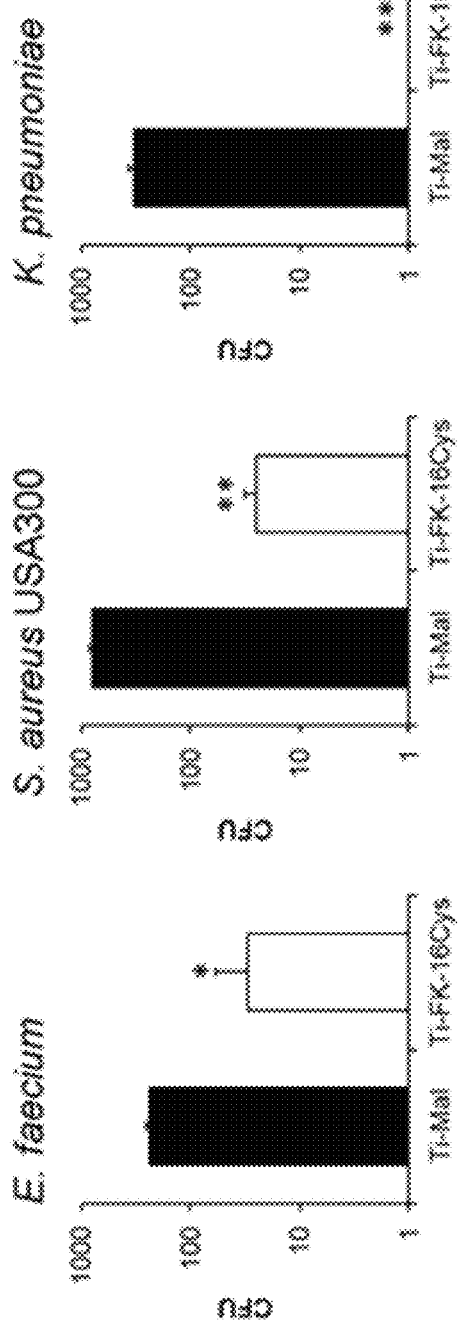
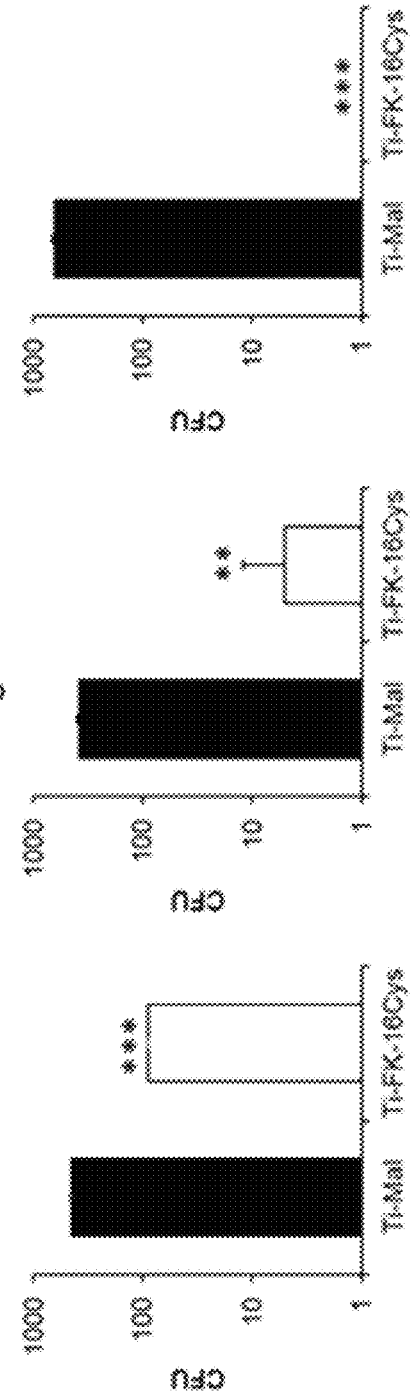
Figure 10A, Figure 10B, Figure 10C, Figure 10D, Figure 10E, Figure 10F

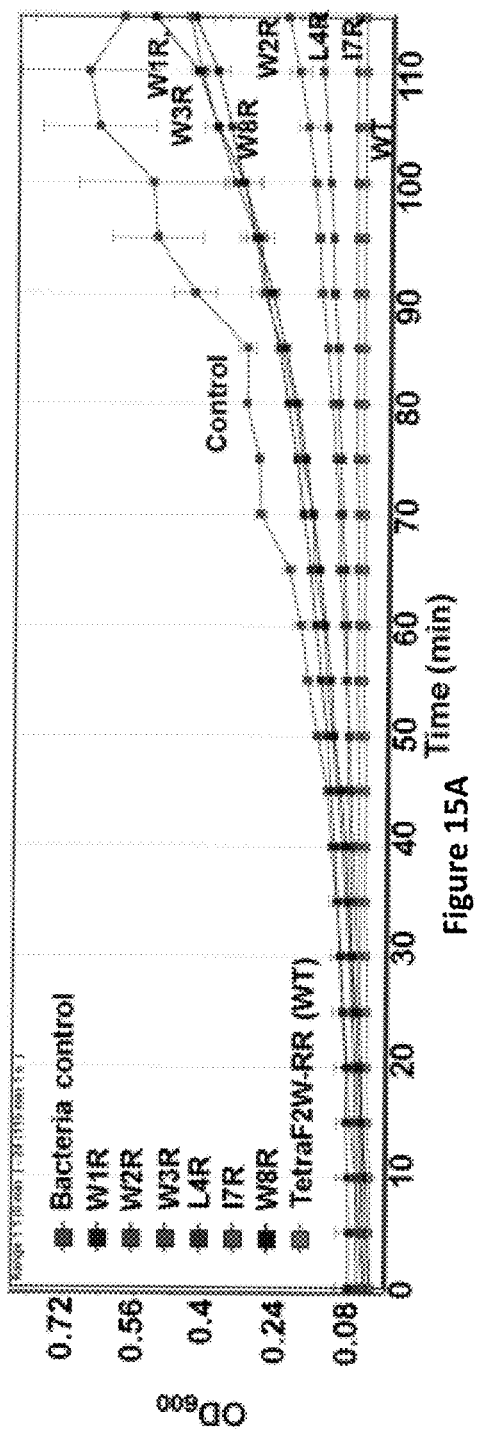
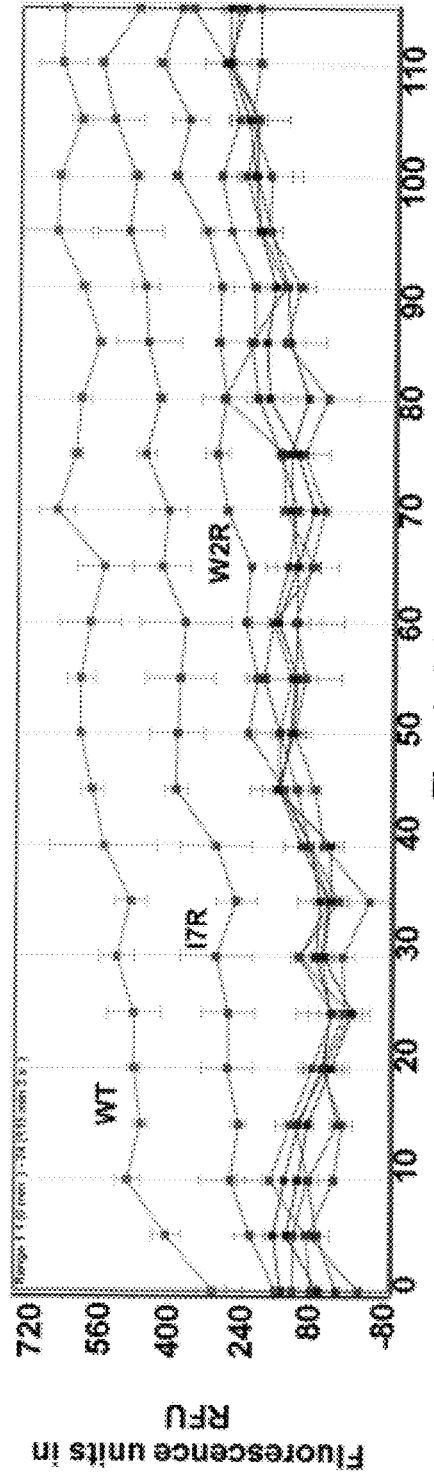
Figure 15A
Figure 15B

ANTI-MICROBIAL PEPTIDES AND COATINGS

This application claims priority under 35 U.S.C. § 119(e) to U.S. Provisional Patent Application No. 62/376,514, filed on Aug. 18, 2016. The foregoing application is incorporated by reference herein.

This invention was made with government support under R01 AI105147 and R03 AI128230 awarded by the National Institutes of Health. The government has certain rights in the invention.

FIELD OF THE INVENTION

The present invention relates to the field of antimicrobial peptides and the treatment of microbial infections. More specifically the invention provides anti-microbial peptides, anti-microbial biofilms, and methods of using such peptides and biofilms for the inhibition, treatment, and/or prevention of microbial infections.

BACKGROUND OF THE INVENTION

Methicillin-resistant *Staphylococcus aureus* (MRSA) strains that are resistant to multiple antibiotics first appeared in clinical settings. Subsequently, resistant Staphylococcal strains were also isolated from the communities (Bancroft et al. (2007) JAMA 298:1803-1804; Kennedy et al. (2008) Proc. Natl. Acad. Sci., 105:1327-1332). MRSA infections can cause life-threatening endocarditis, pneumonia, septicemia, septic arthritis, and osteomyelitis. The community-associated MRSA USA300 strain is responsible for the majority of the skin and soft tissue infection (Krishna et al. (2012) Semin. Immunopathol., 34:261-280). The total deaths due to MRSA infections are comparable to the deaths caused by human immunodeficiency virus type 1 (HIV-1) (Klevens et al. (2007) JAMA 298:1763-1771; Klimek et al. (1976) Am. J. Med., 61:340-345). Bacterial resistance in general—not just limited to MRSA—has rendered many traditional antibiotics ineffective, adding an unwanted burden to medical care. As a consequence, it is critical to develop a new generation of antibiotics that can eliminate microbial infections including superbugs such as MRSA by a mechanism different from those of traditional antibiotics.

SUMMARY OF THE INVENTION

In accordance with one aspect of the instant invention, antimicrobial peptides are provided. In a particular embodiment, the antimicrobial peptide comprises SEQ ID NO: 17 or any antimicrobial peptide disclosed herein. Compositions comprising at least one antimicrobial peptide of the instant invention and at least one pharmaceutically acceptable carrier are also provided. The compositions may further comprise at least one other antimicrobial compound (e.g., antibiotic). Medical devices and medical implants comprising an antimicrobial peptide (e.g., on its surface) are also provided, along with methods of making the same.

In accordance with another aspect of the instant invention, methods for inhibiting, treating, and/or preventing a microbial infection in a subject are provided. The methods comprise administering to a subject at least one antimicrobial peptide of the instant invention, particularly as a composition with a carrier or covalently attached to the surface of a medical device or implant. In a particular embodiment, the methods further comprise the administration at least one other antimicrobial treatment, such as the administration of at least one additional antibiotic.

BRIEF DESCRIPTIONS OF THE DRAWING

FIGS. 1A and 1B show the *Staphylococcus aureus* USA300 killing kinetics of the TetraF2W peptides based on colony counting (FIG. 1A) and propidium iodide cell entrance assay (FIG. 1B). Untreated bacteria were used as a positive control (normal growth), while TSB media served as a negative control (no growth).

FIGS. 2A, 2B, and 2C show the ability of TetraF2W-RR at 25 µM to inhibit the attachment of the *S. aureus* USA300 bacterial cells to solid surfaces (FIG. 2A), inhibit biofilm formation (FIG. 2B), and disrupt preformed biofilms (FIG. 2C), quantified by XTT. Significant values are marked with a * with a P value of <0.04 calculated based on paired student t-test with a two-tailed distribution. FIG. 2D provides confocal laser scanning microscopic images of *S. aureus* biofilms after LIVE/DEAD® staining without (left) and with (right) peptide treatment. FIG. 2E shows the hemolytic effects of the tryptophan-rich peptides on different animal red blood cells. Plotted are hemolysis percentages of 2% red blood cells from bovine, chicken and porcine due to the action of the TetraF2W peptides at 50 µM.

FIGS. 3A-3H show the toxic effects of the TetraF2W peptides on HeLa CCL-2 (FIGS. 3A, 3B, 3C and 3D) and HaCaT cells (FIGS. 3E, 3F, 3G, and 3H). Significant values are marked with a * with a P value <0.05 calculated based on paired student t-test with a two-tailed distribution.

Figure 5:
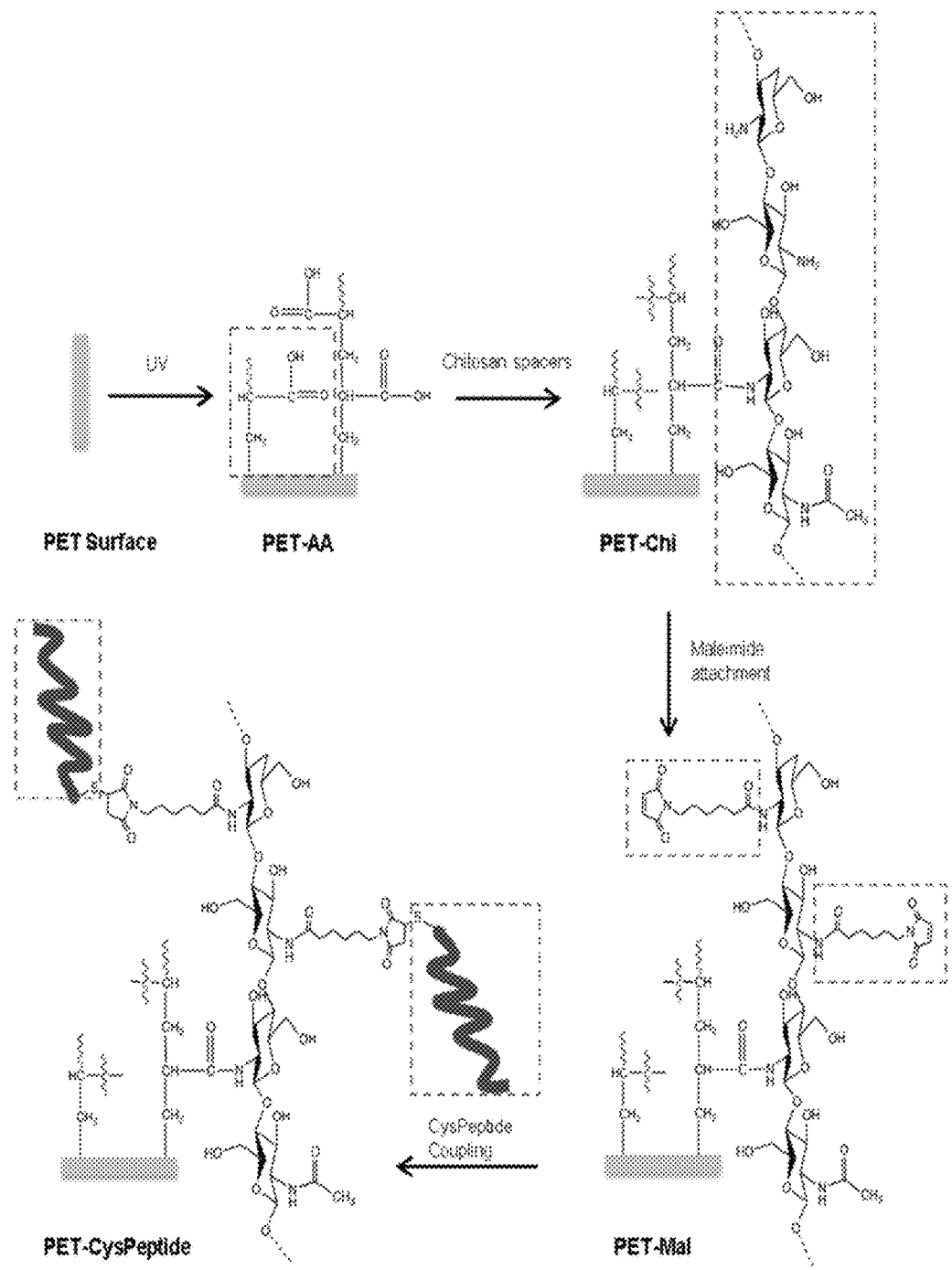

FIG. 5 provides a schematic diagram that depicts the reaction for covalent immobilization of CysTetraF2W-RR onto the PET surface. Newly appended groups in each step are boxed in dotted lines.

Figures 6A, 6B:
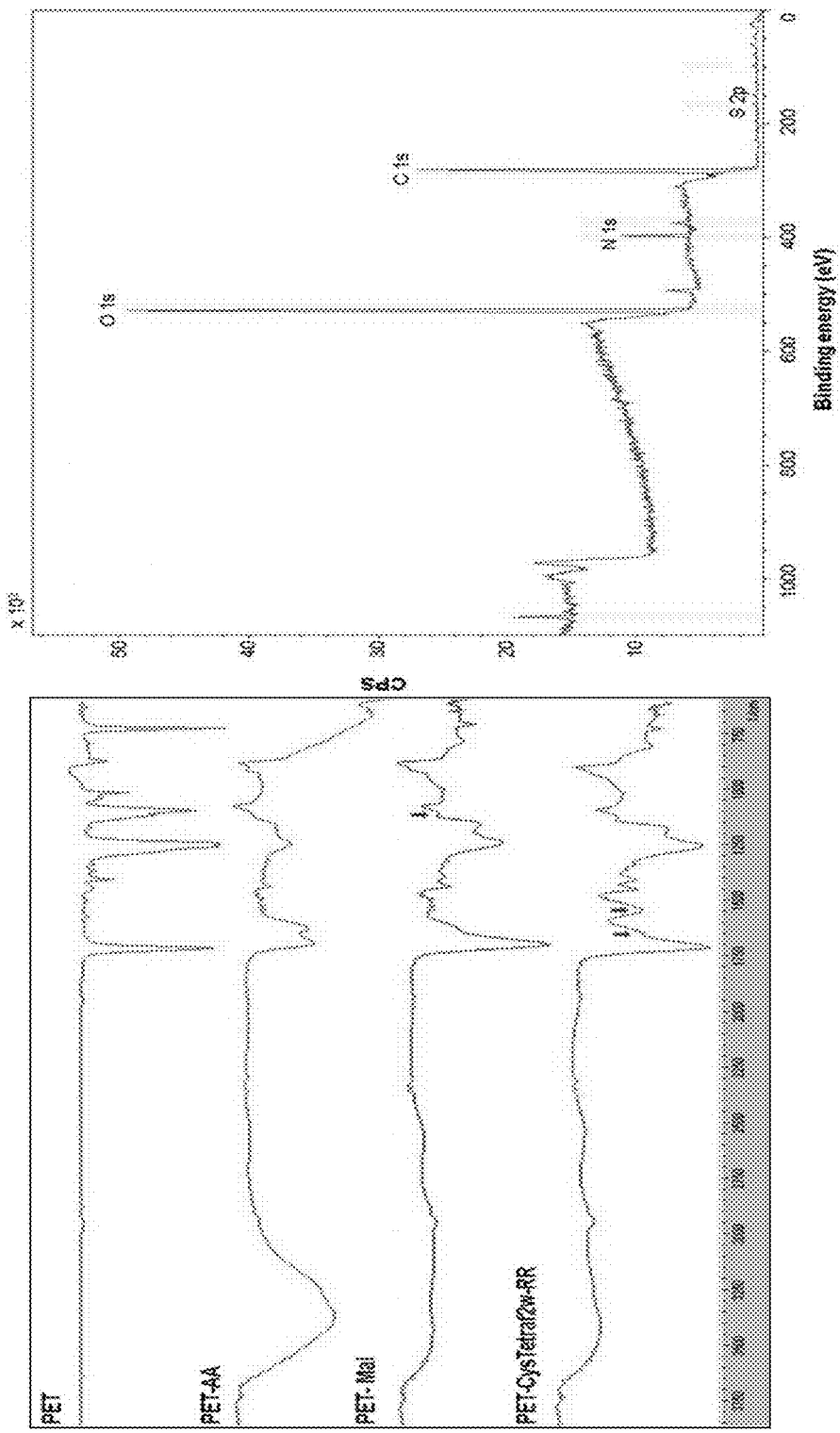

FIG. 6A provides the FT-IR spectra for the products at major reaction steps during the TetraF2W immobilization to the PET surface. The arrows represent the characteristic peaks of glucopyranose at 1080 cm$^{-1}$, the amide I and amide II at 1650 and 1560 cm$^{-1}$, respectively. FIG. 6B provides wide spectrum XPS spectra of the final product showing typical spectra of N 1 s and S 2p.

FIG. 7A provides the *S. aureus* USA300 killing efficacy of the CysTetraF2W-RR peptide-coated PET surfaces as determined by the standard colony counting method. FIG. 7B shows the kinetic killing of *S. aureus* USA300 as a function of optical density with respect to time. FIG. 7C shows the time-dependent increase in the number of dead cells based on the propidium iodide fluorescence. FIG. 7D shows the cytotoxicity of PET-CysTetraF2W-RR to Hela CCL-2 cell lines. An equal amount of soluble peptide was used for comparison (CysTetraF2W-RR). Dead cells are represented by dark right bars. Significant values are marked with a * with a P value <0.05 calculated based on paired student t-test with a two-tailed distribution.

Figure 8B:
Figure 8A:
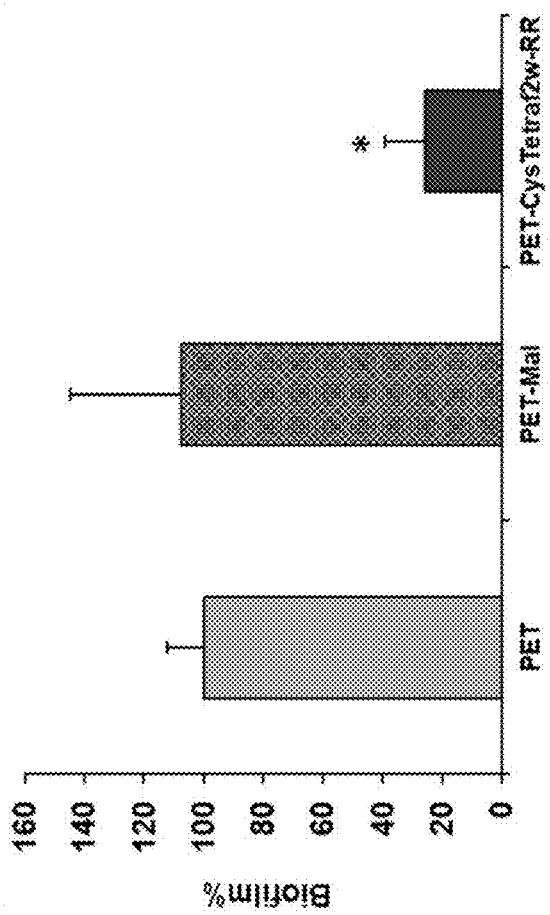

FIG. 8A shows the anti-biofilm activity of the CysTetraF2W-RR coated PET surface. Biofilm formation was allowed for 24 hours followed by quantitative estimation using the XTT assay. The PET surfaces without coating were regarded as 100% biofilm growth whereas coated surfaces without the last step of peptide coupling were compared with the CysTetraF2W-RR coated PET surface to see the distinct effects of peptide immobilization. Significant values are marked with a * with a P value <0.01 calculated based on paired student t-test with a two-tailed distribution. FIG. 8B shows confocal laser scanning microscopic images of 24 hour *S. aureus* biofilms after LIVE/DEAD® staining on PET-Mal control (left) and PET-CysTetraF2W-RR coated surface (right). The presence of a large number of dead cells due to propidium iodide staining on the peptide immobilized surface provides clear evidence for its antibiofilm nature.

Figure 9A:
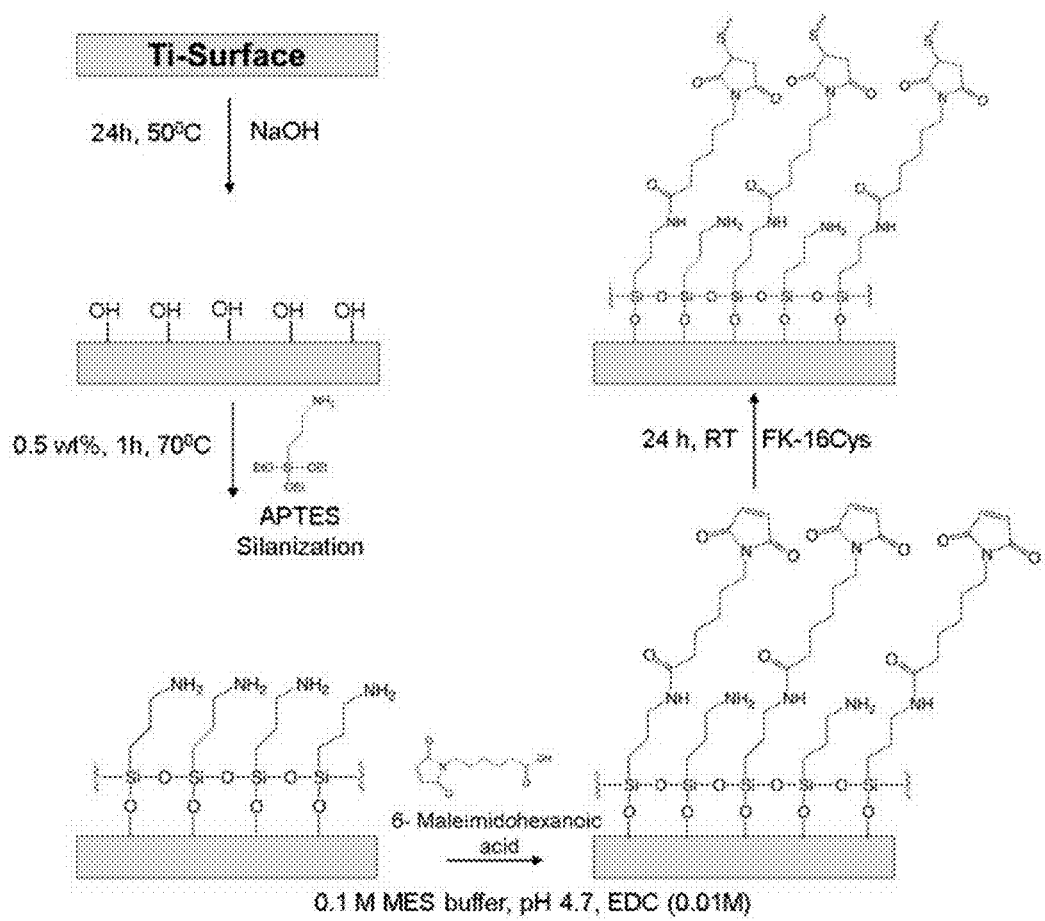
Figure 9B:
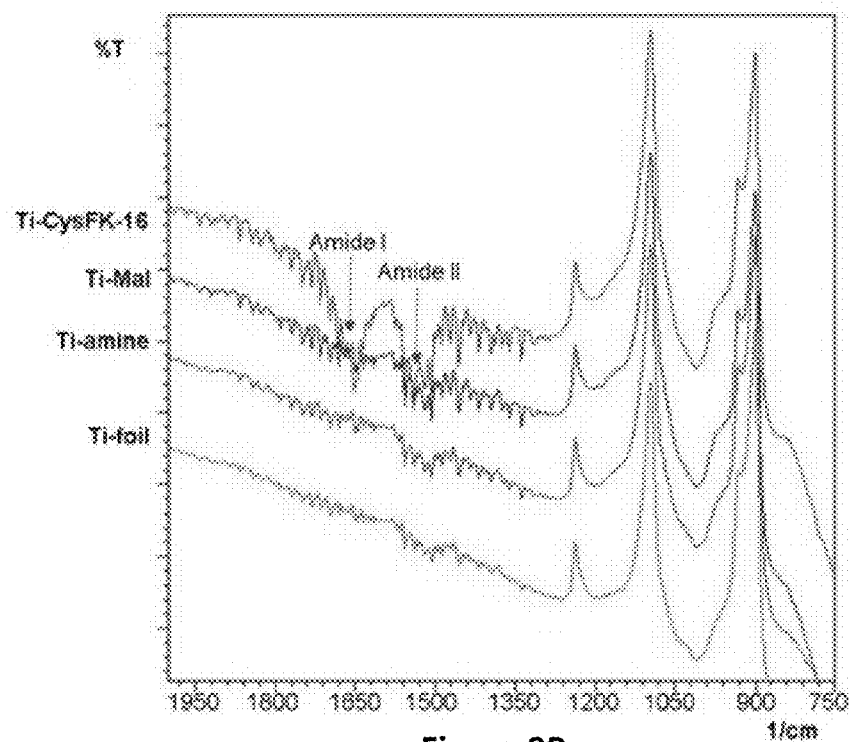
Figure 9C:
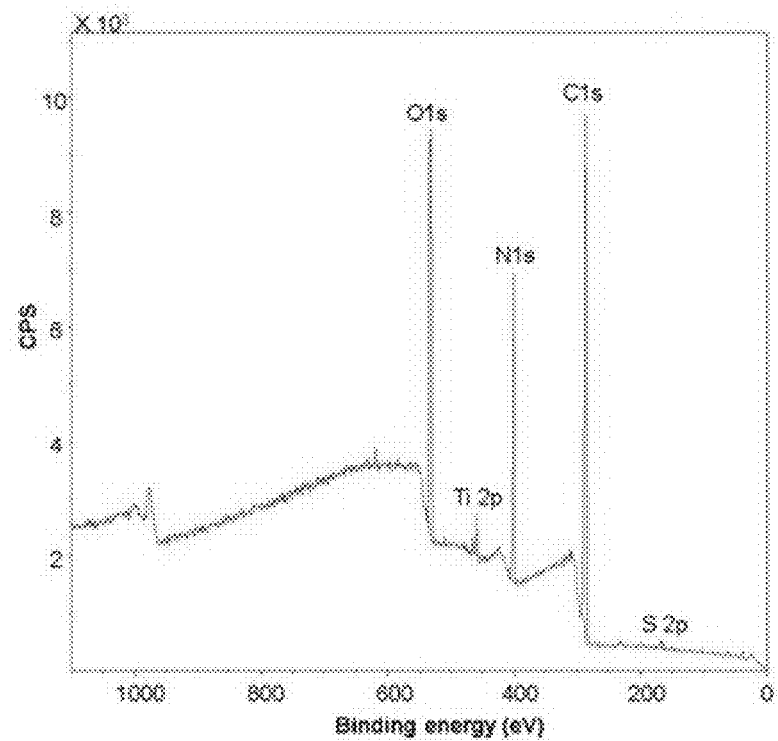

FIG. 9A provides a scheme for peptide coating showing stepwise immobilization of FK-16Cys onto the titanium surface. FIG. 9B provides FT-IR analysis of different reaction steps toward the immobilization of FK-16. FIG. 9C provides XPS analysis showing the wide range spectra of different elements on a FK-16 coated surface.

FIGS. 10A-10F show the antimicrobial activity of the Ti-FK-16Cys surfaces against different ESKAPE pathogens ($2 \times 10^3$ CFU): *E. faecium* (FIG. 10A), *S. aureus* USA300 (FIG. 10B), *K. pneumoniae* (FIG. 10C), *A. baumannii* (FIG. 10D), *P. aeruginosa* (FIG. 10E), and *E. coli* ATCC 25922 (FIG. 10F). Killing efficiency is expressed as the CFU changes of live bacteria compared to the surface coated up to maleimide but no peptide coupling (Ti-Mal). Experiments were done in duplicates and average results were reported. For confirmation, the entire experiment was also repeated on a different date. The error bars represent the standard deviation of the values from the mean. The level of significance was determined by performing Student t-Test with parameters of one tailed distribution with samples of equal variance (*: $p<0.05$; : $p<0.005$ and *: $p<0.0005$).

Figure 11A:
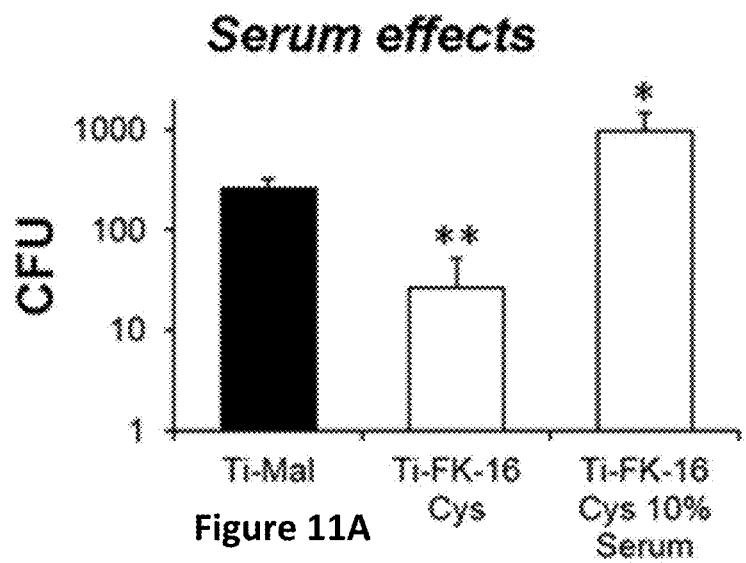
Figure 11B:
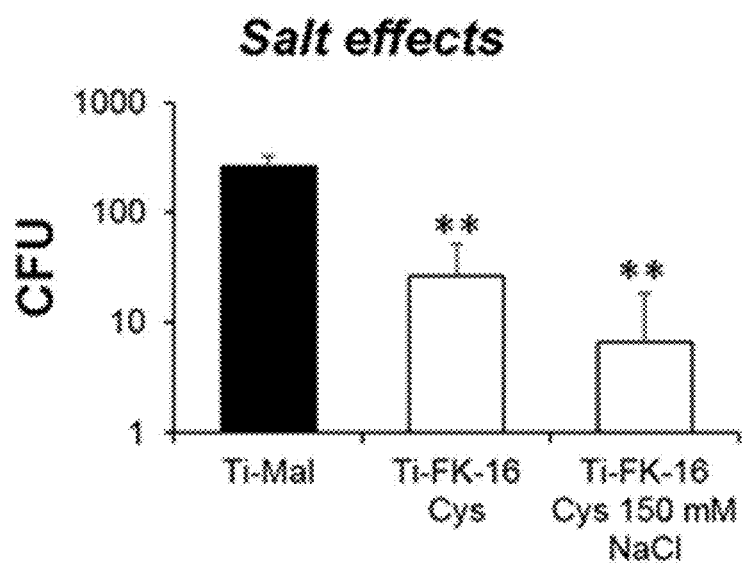

FIGS. 11A and 11B show the antimicrobial activity of the Ti-FK-16Cys surfaces against *S. aureus* USA300 ($2 \times 10^3$ CFU) in the presence of 10% human serum (FIG. 11A) or 150 mM NaCl (FIG. 11B). Killing efficiency is expressed as the CFU changes of live bacteria compared to the surface coated up to maleimide without the peptide (Ti-Mal). Experiments were performed, data processed, and statistically analyzed as described in the legend of FIG. 10.

Figure 12A:
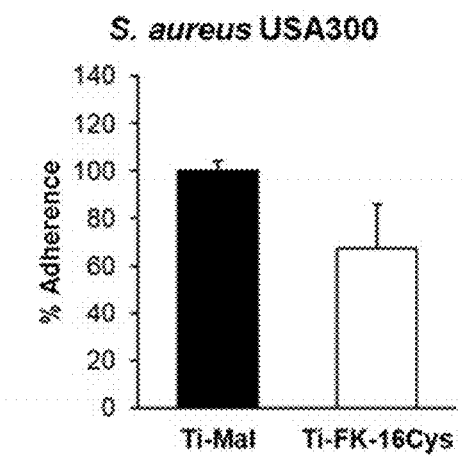
Figure 12B:
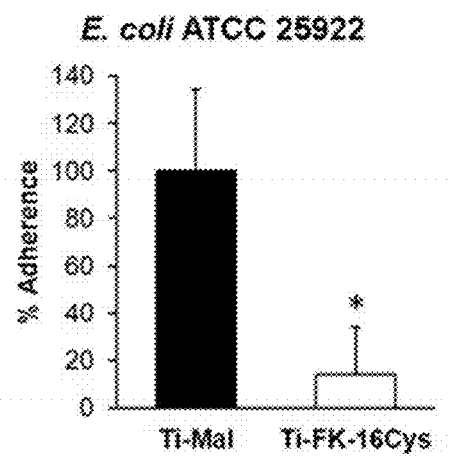

FIGS. 12A and 12B show the anti-adherent property of the FK-16Cys immobilized titanium surfaces. An overnight bacterial culture of *S. aureus* USA300 (FIG. 12A) and *E. coli* ATCC 25922 (FIG. 12B) was allowed to attach to the titanium surface with (open bar) and without (filled bar) the peptide. Experiments were performed, data processed, and statistically analyzed as described in the legend of FIG. 10.

Figure 13:
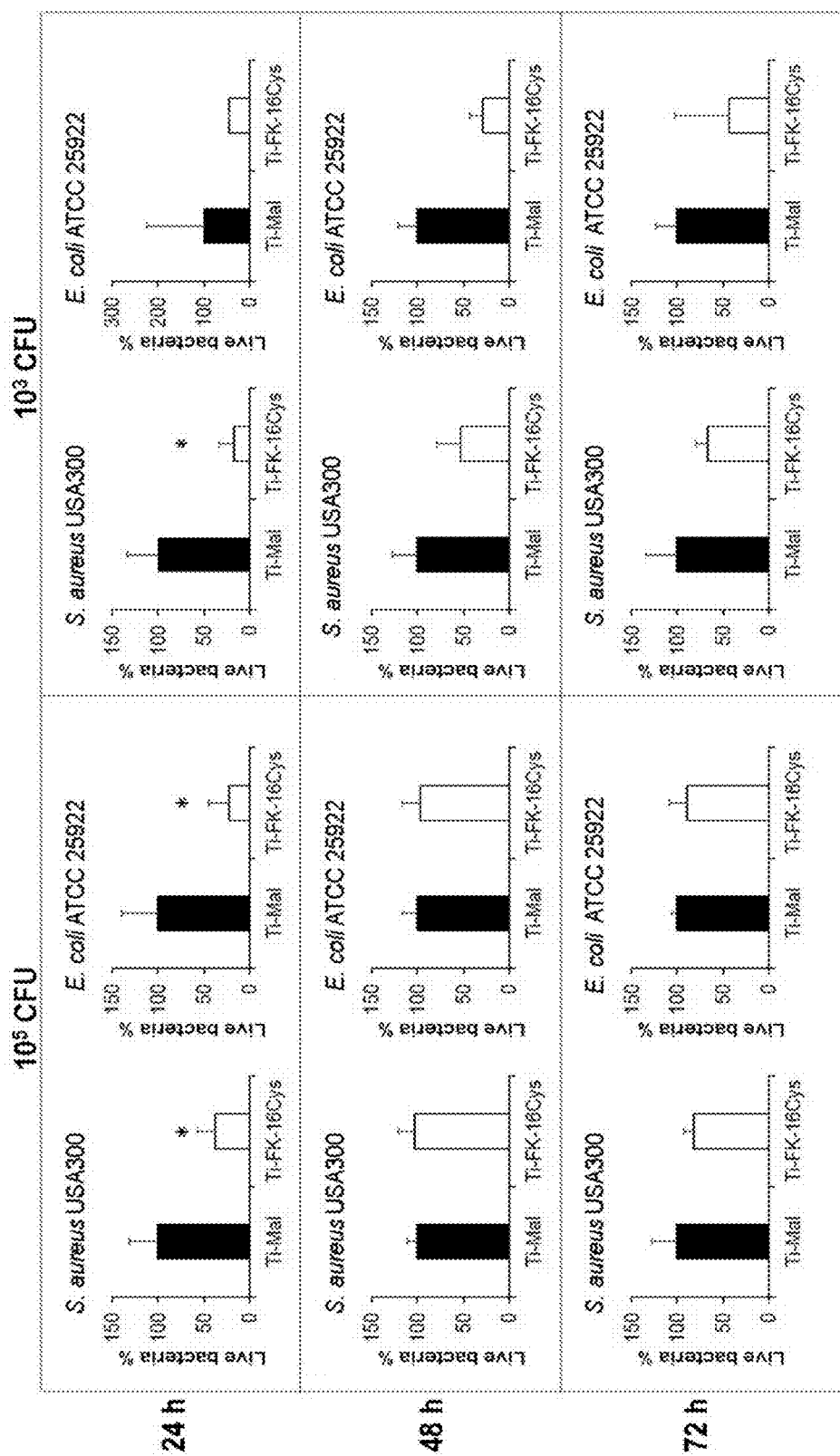

FIG. 13 shows the inhibition of bacterial biofilm formation on the FK-16Cys coated surfaces at bacterial CFU $10^5$ (left) or $10^3$ (right) against *S. aureus* USA300 and *E. coli* ATCC 25922, as indicated. In each experiment, comparison was made between the FK-16Cys peptide coated Ti surfaces (Ti-FK16Cys) and the maleimide coated surfaces devoid of the FK-16 peptide (Ti-Mal). Experiments were performed, data processed, and statistically analyzed as described in the legend of FIG. 10.

Figure 14B:
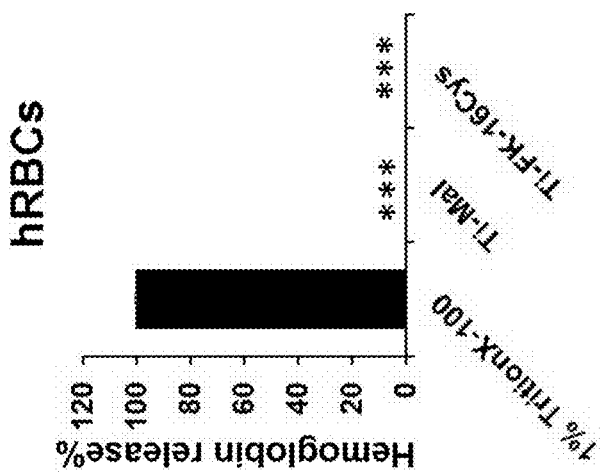
Figure 14A:
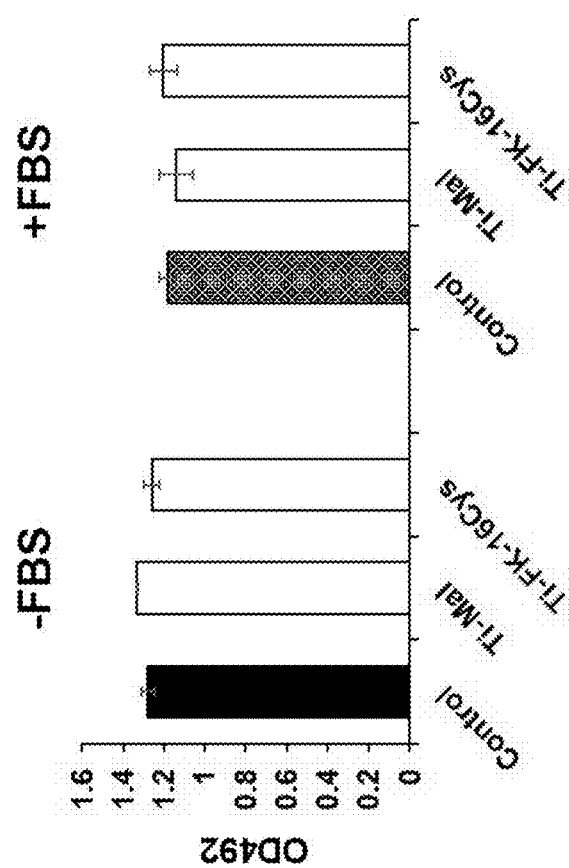

FIGS. 14A and 14B show the cytotoxicity evaluation of the FK-16Cys coated surface to human epidermal keratinocytes HaCaT cells in the absence and presence of FBS (FIG. 14A) and human red blood cells (hRBCs) (FIG. 14B). In each experiment, comparison was made between the peptide coated Ti surface (Ti-FK-16Cys) and the maleimide coated surface devoid of the FK-16 peptide (Ti-Mal). Additional controls (filled columns) were used for the case of HaCaT cells without any treatment (100% live in FIG. 14A) and for hRBCs treated with 1% TRITON™ X-100 (100% lysis in FIG. 14B). Experiments were performed, data processed, and statistically analyzed as described in the legend of FIG. 10.

FIGS. 15A and 15B show the growth inhibition (FIG. 15A) and propidium iodide-based membrane permeation (FIG. 15B) of *S. aureus* USA300 in TSB media by 3.1 µM of TetraF2W-RR and its single arginine variants (Table 8) at 37° C. with shaking at 100 rpm.

Figure 16A:
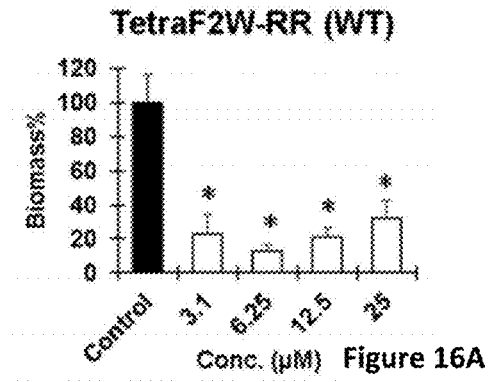
Figure 16B:
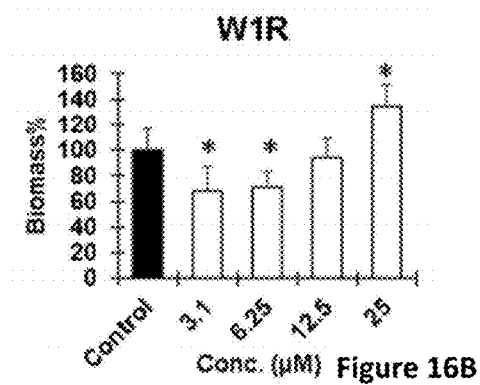
Figure 16C:
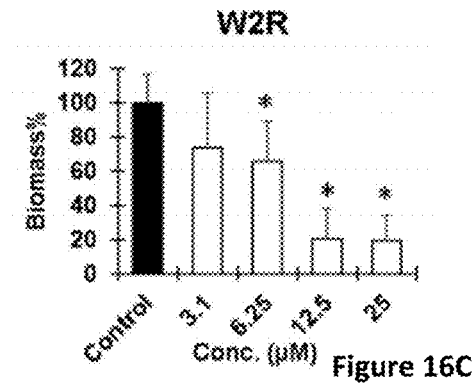
Figure 16D:
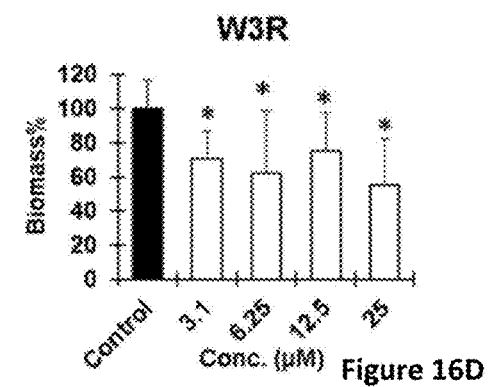
Figure 16E:
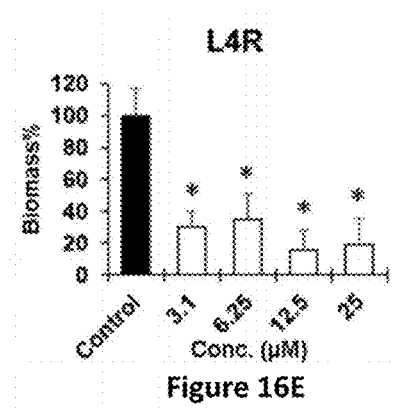
Figure 16F:
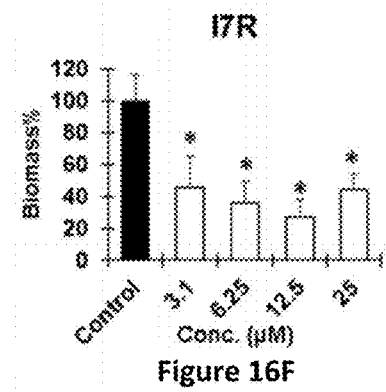
Figure 16G:
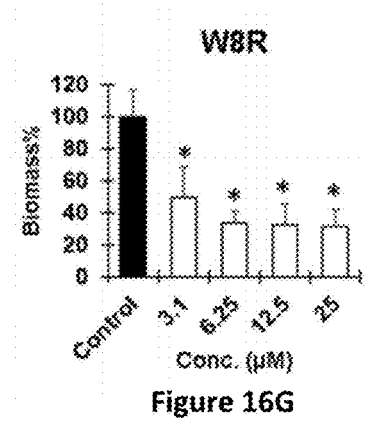
Figure 16H:
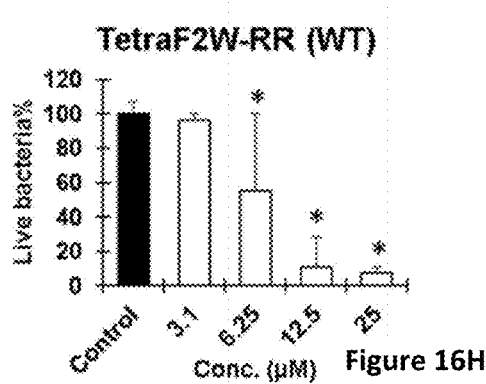
Figure 16L:
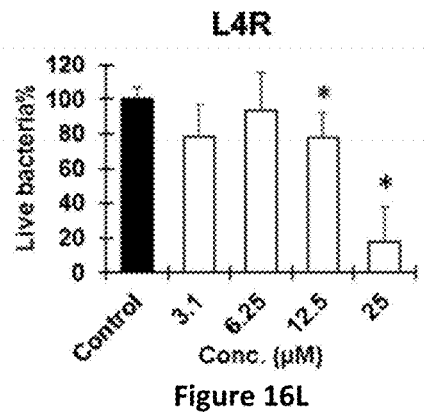
Figure 16I:
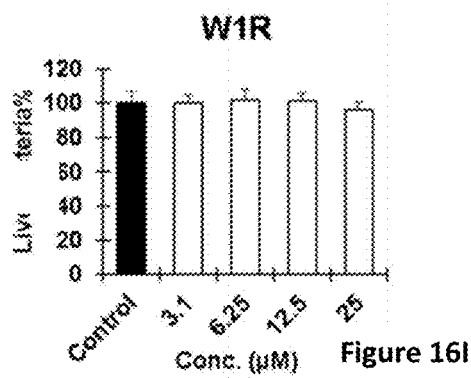
Figure 16M:
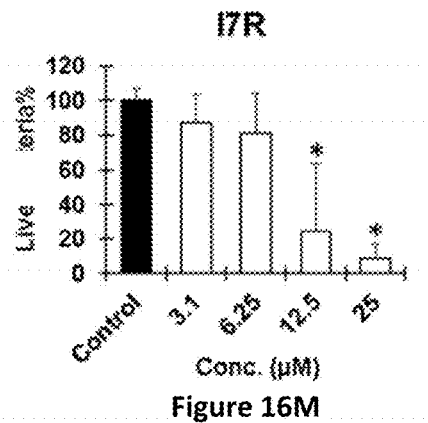
Figure 16J:
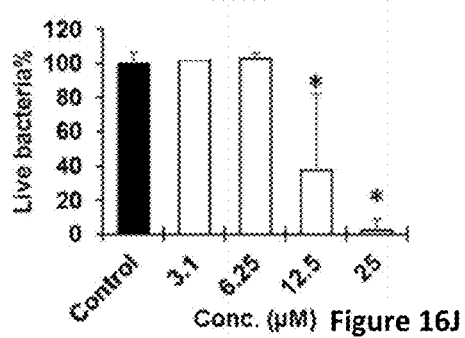
Figure 16N:
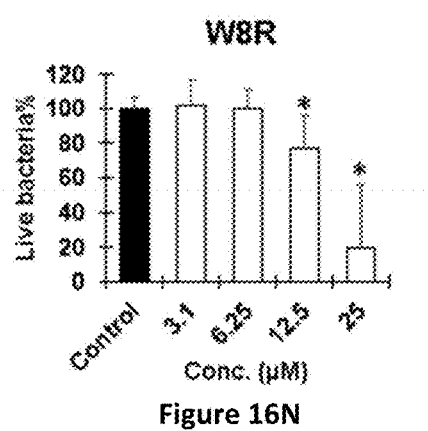
Figure 16K:
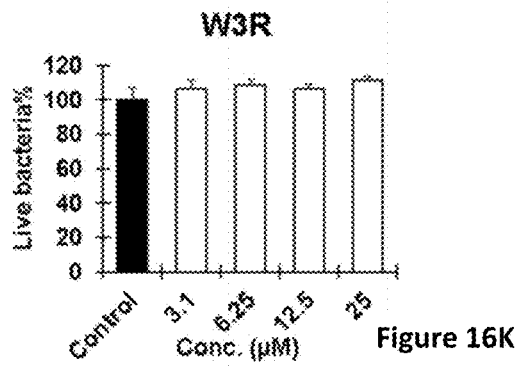

FIGS. 16A-16N show the antibiofilm ability of the Trp-rich peptides (Table 8) against 24-hour preformed biofilms of *S. aureus* USA300. FIGS. 16A-16G were stained with crystal violet, while FIGS. 16H-16N were stained with XTT. Thus, there are two figures for each peptide: peptide TetraF2W-RR (WT): FIGS. 16A and 16H; W1R: FIGS. 16B and 16I; W2R: FIGS. 16C and 16J; W3R: FIGS. 16D and 16K; L4R: FIGS. 16E and 16L; I7R: FIGS. 16F and 16M; W8R: FIGS. 16G and 16N. P values were calculated based on paired Student's t-test with two-tailed distribution. P values <0.05 were considered significant (*).

DETAILED DESCRIPTION OF THE INVENTION

The proliferation of drug resistant bacteria necessitates new bactericidal agents. The present invention provides a variety of short peptides that can kill a wide variety of bacteria including *staphylococcus*. The peptides are further capable of chemical affixation to polymer implements and other kinds of materials.

Infections involving implanted medical devices cost billions of dollars a year. The development of preventative antimicrobial surfaces is considered as the most promising method to combat such infection. Surface coating materials include both metals (e.g., silver, zinc, copper, and zirconium) and non-metals (e.g., selenium and antibiotics). However, the effective use of metals such as silver is complicated by leaching and cytotoxicity issues, whereas a prolonged use of antibiotics results in reduced efficacy due to the emergence of multi-drug resistance pathogens. Surface coating with antimicrobial peptides is the best option to prevent biofilm formation. Antimicrobial peptides have the advantage of being potent against drug-resistant superbugs and will not leak into the surrounding tissues due to covalent immobilization. Notably, the prevention of staphylococcal biofilm formation has been demonstrated in an animal catheter model by injecting merecidin (formerly known as 17BIPHE2), a peptide engineered based on the only human cathelicidin. This invention demonstrates the covalent immobilization of novel antimicrobial peptides to different surfaces ranging from plastics (e.g., polyethylene terephthalate) to metals (e.g., titanium). Notably, the titanium surfaces—after the peptide coating with FK-16 (which corresponds to the major antimicrobial region (residues 17-32) of human cathelicidin LL-37)—show broad spectrum activity against the ESKAPE pathogens (including *Enterococcus faecium*, *Staphylococcus aureus*, *Klebsiella pneumoniae*, *Acinetobacter baumannii*, *Pseudomonas aeruginosa*, and *Enterobacter* species) and can prevent biofilm formation, such as by *S. aureus* and *E. coli*.

Herein, a family of eight-residue tryptophan-rich peptides (TetraF2W) is provided which was obtained by converting the four phenylalanines in temporin-SHf to tryptophans. The temporin-SHf template was identified from the antimicrobial peptide database (aps.unmc.edu/AP). Remarkably, the double arginine variant (TetraF2W-RR) was more effective in killing methicillin-resistant *Staphylococcus aureus* (MRSA) USA300, but less cytotoxic to human skin HaCat and kidney HEK293 cells than the lysine-containing dibasic combinations (KR, RK and KK). Killing kinetics and fluorescence spectroscopy indicate membrane targeting of TetraF2W-RR, making it more difficult for bacteria to develop resistance. Because established biofilms on medical devices are difficult to remove, TetraF2W-RR was covalently immobilized onto a polyethylene terephthalate (PET) surface to prevent biofilm formation. The successful surface coating of the peptide is supported by FT-IR and XPS spectroscopies, chemical quantification, and antibacterial assays. This peptide-coated surface prevented *S. aureus* biofilm formation with no cytotoxicity to human cells. An arginine scan produced further antimicrobial peptides that kill methicillin-resistant *Staphylococcus aureus* USA300 and disrupt preformed bacterial biofilms. Notably, a change of I7 to R led to a potent antimicrobial and antibiofilm peptide with four-fold improvement in cell selectivity. In conclusion, short Trp-rich peptides (e.g., TetraF2W-RR and I7R) with demonstrated antimicrobial and anti-biofilm potency against MRSA in both the free and immobilized forms are provided. Because these short peptides can be synthesized cost effectively, they may be used as new free antimicrobial agents and/or as surface coating compounds.

In accordance with the instant invention, antimicrobial peptides are provided. In a particular embodiment of the instant invention, the peptide comprises the sequence: WWWX$_1$X$_2$X$_3$X$_4$W (SEQ ID NO: 16), wherein X$_1$-X$_4$ are any amino acid or derivative thereof (e.g., an analog). In a particular embodiment, X$_1$ is selected from the group consisting of Ile, Leu, and Val. In a particular embodiment, X$_1$ is Leu. In a particular embodiment, X$_2$ and X$_3$ are positively charged amino acids (e.g., selected from the group of Arg, Lys, His, and a derivatives or analogs thereof). In a particular embodiment, X$_2$ and X$_3$ are independently Arg or Lys. In a particular embodiment, X$_2$ and X$_3$ are independently Arg. In a particular embodiment, X$_4$ is selected from the group consisting of Ile, Arg, and Lys. In a particular embodiment, X$_4$ is Arg.

In a particular embodiment of the instant invention, the peptide comprises the sequence: WWWLX$_1$X$_2$X$_3$W (SEQ ID NO: 17), wherein X$_1$-X$_3$ are any amino acid or derivative thereof (e.g., an analog). In a particular embodiment, X$_1$ and X$_2$ are positively charged amino acids (e.g., selected from the group of Arg, Lys, His, and a derivatives or analogs thereof). In a particular embodiment, X$_1$ and X$_2$ are independently Arg or Lys. In a particular embodiment, X$_1$ and X$_2$ are independently Arg. In a particular embodiment, X$_3$ is selected from the group consisting of Ile, Arg, and Lys. In a particular embodiment, X$_3$ is Arg.

In a particular embodiment, the peptide comprises any one of SEQ ID NOs: 1-6 or 10-15.

The amino acid sequence of the antimicrobial peptide of the instant invention may have at least 75%, at least 80%, at least 85%, at least 90%, at least 95%, at least 97%, at least 99%, or 100% homology with any one of the above sequences (e.g., SEQ ID NOs: 1-6 or 10-17), particularly at least 90% homology (e.g., the sequence may contain additions, deletions, and/or substitutions). In a particular embodiment, the antimicrobial peptide of the instant invention may extend beyond the above sequences (e.g., SEQ ID NOs: 1-6 or 10-17) at the amino and/or carboxyl terminus by 1, 2, 3, 4, 5, 6, 7, 8, 9, or 10 amino acids, particularly by 1, 2, 3, 4, or 5 amino acids, by 1, 2, or 3 amino acids, by 1 or 2 amino acids, or by 1 amino acid. In yet another embodiment, the antimicrobial inhibitory peptides of the instant invention may also be in reverse orientation (i.e., the sequence from amino terminus to carboxyl terminus is reversed).

In a particular embodiment, the peptides of the instant invention have fewer than about 50 amino acids, fewer than about 25 amino acids, fewer than about 20 amino acids, fewer than about 17 amino acids, fewer than about 15 amino acids, fewer than about 12 amino acids, fewer than about 10 amino acids, or fewer than 9 amino acids. In a particular embodiment, the peptides of the instant invention have more than about 6 amino acids, particularly more than about 7 amino acids. In a particular embodiment, the peptides of the instant invention are about 7 to about 12 amino acids in length, about 8-10 amino acids in length, about 8 or 9 amino acids in length, or about 8 amino acids in length.

In a particular embodiment, the antimicrobial peptide of the instant invention comprises one of the above sequences (e.g., SEQ ID NOs: 1-6 or 10-17) and a terminal cysteine. In a particular embodiment, the cysteine is at the amino terminus. In a particular embodiment, the cysteine is at the carboxyl terminus. As explained herein, the presence of the cysteine provides functionality to allow the covalent linkage of the antimicrobial peptide to, for example, a solid surface (e.g., a medical implant).

As stated hereinabove, the antimicrobial peptide of the instant invention may contain substitutions for the amino acids of the provided sequence. These substitutions may be similar to the amino acid (i.e., a conservative change) present in the provided sequence (e.g., an acidic amino acid in place of another acidic amino acid, a basic amino acid in place of a basic amino acid, a large hydrophobic amino acid in place of a large hydrophobic, etc.). The substitutions may also comprise amino acid analogs and mimetics. In a particular embodiment, the substitutions are predicted to promote helicity or helix formation.

The antimicrobial peptide of the instant invention may have capping, protecting and/or stabilizing moieties at the C-terminus and/or N-terminus. Such moieties are well known in the art and include, without limitation, amidation and acetylation. The peptide template may also be lipidated or glycosylated at any amino acid (i.e., a glycopeptide). In particular, these peptides may be PEGylated to improve druggability. The number of the PEG units (NH$_2$(CH$_2$CH$_2$O)CH$_2$CH$_2$CO) may vary, for example, from 1 to about 50.

The antimicrobial peptide of the instant invention may also comprise at least one D-amino acid instead of the native L-amino acid. The antimicrobial peptide may comprise only D-amino acids. In a particular embodiment, the antimicrobial peptides comprise D-amino acids which are spaced apart by about 1, 2, 3, and/or 4 (e.g., 3) consecutive L-amino acids.

The antimicrobial peptides of the instant invention may contain at least one derivative of standard amino acids, such as, without limitation, fluorinated residues or nonstandard amino acids (e.g., beta-amino acids). In yet another embodiment, the peptide may also be circulated head to tail or locally involving a few residues.

The present invention also encompasses compositions comprising at least one antimicrobial peptide of the instant invention and at least one carrier (e.g., a pharmaceutically acceptable carrier). The present invention also encompasses methods for preventing, inhibiting, and/or treating microbial infections (as explained further hereinbelow). The compositions of the instant invention can be administered to an animal, in particular a mammal, more particularly a human, in order to treat, inhibit, and/or prevent a microbial (e.g., bacterial such as by *E. coli*, MRSA, etc.) infection (e.g., the composition may be administered before, during, and/or after a microbial infection). The compositions of the instant invention may also comprise at least one other antimicrobial agent (e.g., an antibiotic). The additional antimicrobial agent may also be administered in a separate composition from the antimicrobial peptides of the instant invention. The compositions may be administered at the same time and/or at different times (e.g., sequentially). The composition(s) comprising at least one antimicrobial peptide of the instant invention and the composition(s) comprising at least one additional antibiotic may be contained within a kit.

The antimicrobial peptides of the present invention may be prepared in a variety of ways, according to known methods. In a particular embodiment, the antimicrobial peptides of the instant invention are chemically synthesized. For example, the peptides may be synthesized using a liquid-phase method or solid-phase method. The chemically synthesized peptides may then be purified (e.g., by HPLC).

The antimicrobial peptides may also be purified from appropriate sources (e.g., bacterial or animal cultured cells or tissues, optionally transformed) by immunoaffinity purification. The availability of nucleic acid molecules encoding the antimicrobial peptides enables production of the protein using in vitro expression methods and cell-free expression systems known in the art.

Larger quantities of antimicrobial peptides may be produced by expression in a suitable prokaryotic or eukaryotic system. For example, part or all of a DNA molecule encoding for an antimicrobial peptide may be inserted into a plasmid vector adapted for expression in a bacterial cell, such as *E. coli*. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

Antimicrobial peptides produced by gene expression in a recombinant prokaryotic or eukaryotic system may be purified according to methods known in the art. A commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemaglutinin epitope. Such methods are commonly used by skilled practitioners.

Antimicrobial peptides of the invention, prepared by the aforementioned methods, may be analyzed and verified according to standard procedures. For example, such protein may be subjected to amino acid sequence analysis, according to known methods.

In accordance with another aspect of the instant invention, medical devices or implants comprising at least one antimicrobial peptide are provided, along with methods of making the same. As used herein, the term "medical device" or "medical implant" includes devices, implants, and materials that are permanently implanted and those that are temporarily or transiently present in the patient. In a particular embodiment, at least part of the exposed surface of the medical device or implant is coated with at least one antimicrobial peptide of the instant invention. In a particular embodiment, the medical device or implant comprises a plastic (e.g., polyethylene terephthalate) or a metal (e.g., titanium). In a particular embodiment, the antimicrobial peptide is covalently attached to the surface of the medical implant or device. The antimicrobial peptide may be linked directly (e.g., via a bond) to the surface of the medical device or implant or covalently attached via a linker (e.g., a crosslinker).

The antimicrobial peptide attached to the surface of the medical device or medical implant may be any peptide having antimicrobial activity. In a particular embodiment, the antimicrobial peptide is listed in the antimicrobial peptide database (aps.unmc.edu/AP). In a particular embodiment, the antimicrobial peptide comprises one of the above sequences (e.g., SEQ ID NOs: 1-6 or 10-17). In a particular embodiment, the antimicrobial peptide is FK-16.

The instant invention also encompasses methods of synthesizing the coated medical device or medical implant of the instant invention. In a particular embodiment, the method comprises linking an antimicrobial peptide of the instant invention comprising a terminal cysteine to the medical device or medical implant with a sulfhydryl reactive crosslinker (e.g., a maleimide crosslinker). The crosslinker may be reacted with the antimicrobial peptide first, with the medical device or medical implant first, or with both simultaneously. In a particular embodiment, the antimicrobial peptide is linked to a biocompatible polymer (e.g., chitosan) with a sulfhydryl reactive crosslinker (e.g., a maleimide crosslinker), wherein the biocompatible polymer is attached to the medical device or medical implant.

The term "crosslinker" refers to a molecule capable of forming a covalent linkage between compounds. In a particular embodiment, the crosslinker forms a covalent linkage (e.g., a sulfide bond) via the sulfhydryl group of the terminal cysteine of the antimicrobial peptide. Crosslinkers are well known in the art. The cross-linker may be a bifunctional, trifunctional, or multifunctional crosslinking reagent. In a particular embodiment, the crosslinker is non-biodegradable or uncleavable under physiological conditions. In a particular embodiment, the crosslinker is a maleimide crosslinker.

In accordance with another aspect of the instant invention, nucleic acid molecules encoding the antimicrobial peptides are provided. Nucleic acid molecules encoding the antimicrobial peptides of the invention may be prepared by any method known in the art such as, without limitation: (1) synthesis from appropriate nucleotide triphosphates or (2) isolation and/or amplification from biological sources. The availability of nucleotide sequence information enables preparation of an isolated nucleic acid molecule of the invention by oligonucleotide synthesis. Indeed, knowledge of the amino sequence is sufficient to determine an encoding nucleic acid molecule. Synthetic oligonucleotides may be prepared by the phosphoramidite method employed in the Applied Biosystems 38A DNA Synthesizer or similar devices. The resultant construct may be purified according to methods known in the art, such as gel electrophoresis or high performance liquid chromatography (HPLC).

Nucleic acids of the present invention may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. Antimicrobial peptide encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the antimicrobial peptide nucleic acid molecules of the invention. Primers capable of specifically amplifying antimicrobial peptides encoding nucleic acids described herein are also contemplated herein. Such oligonucleotides are useful as probes and primers for detecting, isolating or amplifying antimicrobial peptide encoding nucleic acids.

The present invention also encompasses compositions comprising at least one nucleic acid encoding an antimicrobial peptide of the instant invention and at least one carrier (e.g., pharmaceutically acceptable carrier). The present invention also encompasses methods for preventing, inhibiting, and/or treating microbial infections (as explained hereinbelow). The compositions of the instant invention can be administered to an animal, in particular a mammal, more particularly a human, in order to treat, inhibit, and/or prevent a microbial (e.g., bacterial such as by E. coli, MRSA, etc.) infection (e.g., the composition may be administered before, during, and/or after a microbial infection). The compositions of the instant invention may also comprise at least one other antimicrobial agent (e.g., an antibiotic). The additional antimicrobial agent may also be administered in a separate composition from the antimicrobial peptides of the instant invention. The compositions may be administered at the same time or at different times (e.g., sequentially). The composition(s) comprising at least one anti-microbial peptide of the instant invention and the composition(s) comprising at least one additional antibiotic may be contained within a kit.

As stated hereinabove, the present invention also encompasses compositions comprising at least one antimicrobial peptide of the instant invention and at least one carrier (e.g., pharmaceutically acceptable carrier). The compositions comprising the antimicrobial peptides of the instant invention may be conveniently formulated for administration with any pharmaceutically acceptable carrier(s). For example, the antimicrobial peptides may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents, or suitable mixtures thereof, particularly an aqueous solution. The concentration of the antimicrobial peptide in the chosen medium may be varied and the medium may be chosen based on the desired route of administration of the pharmaceutical composition. Except insofar as any conventional media or agent is incompatible with the antimicrobial peptide to be administered, its use in the pharmaceutical composition is contemplated.

The present invention also encompasses methods for preventing, inhibiting, and/or treating microbial infections (e.g., viral or bacterial), particularly a bacterial infection such as S. aureus infections (e.g., MRSA). The method comprises administering at least one antimicrobial peptide of the instant invention to the subject. The method may further comprise administering at least one additional antimicrobial (e.g., antibiotic). In a particular embodiment, the microbe is an antibiotic-resistant bacteria or an ESKAPE pathogen. In a particular embodiment, the microbe is in a biofilm. In a particular embodiment, the microbe is selected from the group consisting of Enterococcus faecium, Staphylococcus aureus, Klebsiella pneumoniae, Acinetobacter baumanii, Pseudomonas aeruginosa, and Enterobacter species. The compositions of the instant invention can be administered to an animal, in particular a mammal, more particularly a human, in order to treat, inhibit, and/or prevent a microbial infection (e.g., the composition may be administered before, during, and/or after a microbial infection). The pharmaceutical compositions of the instant invention may also comprise at least one other antimicrobial agent, particularly at least one other antibiotic. The additional antimicrobial agent may also be administered in a separate composition from the antimicrobial peptides of the instant invention. The compositions may be administered at the same time and/or at different times (e.g., sequentially).

In a particular embodiment, the antimicrobial peptides of the instant invention are administered to the subject as a coating on a medical device or implant.

Bacterial infections that may be treated using the present methods include Gram-positive bacterial infections and Gram-negative bacterial infections. In a particular embodiment, the bacteria is a Gram-positive bacteria. In a particular embodiment, the bacteria is a staphylococcal strain. In yet another embodiment, the bacteria is Staphylococcus aureus. More particularly, the bacteria is MRSA. In a particular embodiment, the bacteria is an antibiotic-resistant bacteria or an ESKAPE pathogen. In a particular embodiment, the bacteria is selected from the group consisting of Enterococcus faecium, Staphylococcus aureus, Klebsiella pneumoniae, Acinetobacter baumanii, Pseudomonas aeruginosa, and Enterobacter species.

The antimicrobial peptides described herein will generally be administered to a patient as a pharmaceutical composition. The term "patient" as used herein refers to human or animal subjects. These antimicrobial peptides may be employed therapeutically, under the guidance of a physician.

The dose and dosage regimen of antimicrobial peptides according to the invention that are suitable for administration to a particular patient may be determined by a physician considering the patient's age, sex, weight, general medical condition, and the specific condition for which the antimicrobial peptides are being administered and the severity thereof. The physician may also take into account the route of administration, the pharmaceutical carrier, and the antimicrobial peptide's biological activity.

Selection of a suitable pharmaceutical composition will also depend upon the mode of administration chosen. For example, the antimicrobial peptides of the invention may be administered by direct injection or intravenously. In this instance, a pharmaceutical composition comprises the antimicrobial peptide dispersed in a medium that is compatible with the site of injection.

Antimicrobial peptides of the instant invention may be administered by any method. For example, the antimicrobial peptides of the instant invention can be administered, without limitation by injection, parenterally, subcutaneously, orally, nasally, topically, pulmonarily, rectally, vaginally, intravenously, intraperitoneally, intrathecally, intracerbrally, epidurally, intramuscularly, intradermally, intracarotidly, or other modes of administration such as controlled release devices. In a particular embodiment, the antimicrobial peptides are administered intramuscularly, subcutaneously, or to the bloodstream (e.g., intravenously). In a particular embodiment, the antimicrobial peptides are administered by injection. The composition may be directly administered (e.g., by injection) to the site of microbial infection. In general, pharmaceutical compositions and carriers of the present invention comprise, among other things, pharmaceutically acceptable diluents, preservatives, stabilizing agents, solubilizers, emulsifiers, adjuvants and/or carriers. Such compositions can include diluents of various buffer content (e.g., saline, Tris HCl, acetate, phosphate), pH and ionic strength; and additives such as detergents and solubilizing agents (e.g., Tween™ 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. Exemplary pharmaceutical compositions and carriers are provided, e.g., in "Remington's Pharmaceutical Sciences" by E. W. Martin (Mack Pub. Co., Easton, Pa.) and "Remington: The Science And Practice Of Pharmacy" by Alfonso R. Gennaro (Lippincott Williams & Wilkins) which are herein incorporated by reference. The compositions of the present invention can be prepared, for example, in liquid form, or can be in pill or dried powder form (e.g., lyophilized).

Pharmaceutical compositions for injection are known in the art. If injection is selected as a method for administering the antimicrobial peptide, steps must be taken to ensure that sufficient amounts of the molecules or cells reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing an antimicrobial peptide of the present invention as the active ingredient in intimate admixture with a pharmaceutically acceptable carrier can be prepared according to conventional pharmaceutical compounding techniques. The carrier may take a wide variety of forms depending on the form of pharmaceutical composition desired for administration, e.g., intravenous, oral, direct injection, intracranial, and intravitreal.

In yet another embodiment, the compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald al., Surgery (1980) 88:507; Saudek et al., N. Engl. J. Med. (1989) 321:574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105).

A pharmaceutical composition of the invention may be formulated in dosage unit form for ease of administration and uniformity of dosage. Dosage unit form, as used herein, refers to a physically discrete unit of the pharmaceutical composition appropriate for the patient undergoing treatment. Each dosage should contain a quantity of active ingredient calculated to produce the desired effect (e.g., curing, relieving, treating, and/or preventing the microbial infection, the symptoms of it, or the predisposition towards it) in association with the selected pharmaceutical carrier. The dosage should not be so large as to cause adverse side effects, such as unwanted cross-reactions, anaphylactic reactions, and the like. Procedures for determining the appropriate dosage unit are well known to those skilled in the art. Generally, the dosage will vary with the age, weight, condition, sex and extent of the disease in the patient and can be determined by one of skill in the art. Appropriate concentrations for alleviation of a particular pathological condition may be determined by dosage concentration curve calculations, as known in the art. The dosage can be adjusted by the individual physician in the event of any counter indications.

In accordance with the present invention, the appropriate dosage unit for the administration of antimicrobial peptides may be determined by evaluating the toxicity of the molecules or cells in animal models. Various concentrations of antimicrobial peptides in pharmaceutical composition may be administered to mice, and the minimal and maximal dosages may be determined based on the beneficial results and side effects observed as a result of the treatment. Appropriate dosage unit may also be determined by assessing the efficacy of the antimicrobial peptide treatment in combination with other standard drugs. The dosage units of antimicrobial peptide may be determined individually or in combination with each treatment according to the effect detected.

The pharmaceutical composition comprising the antimicrobial peptides may be administered at appropriate intervals until the pathological symptoms are reduced or alleviated, after which the dosage may be reduced to a maintenance level. The appropriate interval in a particular case would normally depend on the condition of the patient.

The instant also encompasses delivering the antimicrobial peptides of the instant invention to a cell in vitro (e.g., in culture). The antimicrobial peptide may be delivered to the cell in at least one carrier.

Definitions

The following definitions are provided to facilitate an understanding of the present invention.

The singular forms "a," "an," and "the" include plural referents unless the context clearly dictates otherwise.

The term "isolated" is not meant to exclude artificial or synthetic mixtures with other compounds or materials, or the presence of impurities that do not interfere with the fundamental activity, and that may be present, for example, due to incomplete purification, or the addition of stabilizers.

The term "substantially pure" refers to a preparation comprising at least 50-60% by weight of a given material (e.g., nucleic acid, oligonucleotide, protein, etc.). Particularly, the preparation comprises at least 75% by weight, at least 80% by weight, at least 90% by weight, or at least 95% or more by weight of the given compound. Purity may be measured by methods appropriate for the given compound (e.g. chromatographic methods, agarose or polyacrylamide gel electrophoresis, HPLC analysis, and the like).

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween™ 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., microbial (e.g., bacterial) infection) resulting in a decrease in the probability that the subject will develop the condition.

A "therapeutically effective amount" of a compound or a pharmaceutical composition refers to an amount effective to prevent, inhibit, treat, and/or lessen the symptoms of a particular disorder or disease. The treatment of a microbial infection (e.g., a bacterial infection such as a *S. aureus* infection) herein may refer to an amount sufficient to inhibit microbial growth or kill the microbe and/or curing, relieving, and/or preventing the microbial infection, the symptom of it, or the predisposition towards it.

As used herein, the term "antibiotic" refers to antimicrobial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

As used herein, the term "subject" refers to an animal, particularly a mammal, particularly a human.

The term "promoter" as used herein refers to a DNA sequence which directs transcription of a polynucleotide sequence operatively linked thereto (e.g., in a cell). The promoter may also comprise enhancer elements which stimulate transcription from the linked promoter. The term "enhancer" refers to a DNA sequence which binds to the transcription initiation complex and facilitates the initiation of transcription at the associated promoter.

A "vector" is a nucleic acid molecule such as a plasmid, cosmid, bacmid, phage, or virus, to which another genetic sequence or element (either DNA or RNA) may be attached/inserted so as to bring about the replication and/or expression of the sequence or element (e.g., under the control of a promoter contained within the vector).

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. An isolated nucleic acid (either DNA or RNA) may further represent a molecule produced directly by biological or synthetic means and separated from other components present during its production.

"Linker" refers to a chemical moiety comprising a covalent bond or a chain of atoms that covalently attach at least two compounds. The linker can be linked to any synthetically feasible position of the compounds, but preferably in such a manner as to avoid blocking the compounds desired activity. Linkers are generally known in the art. In a particular embodiment, the linker may contain from 0 (i.e., a bond) to about 50 atoms, from 0 to about 10 atoms, or from about 1 to about 5 atoms.

The term "antimicrobials" as used herein indicates a substance that kills or inhibits the growth of microorganisms such as bacteria, fungi, viruses, or protozoans, particularly bacteria.

The following examples describe illustrative methods of practicing the instant invention and are not intended to limit the scope of the invention in any way.

Example 1

Natural antimicrobial peptides (AMPs) are host defense molecules identified in various organisms ranging from bacteria to humans. The majority of these molecules contain 10-50 amino acids with net charges 0-+7 and hydrophobic contents 31-70% (Wang, G. (2013) Pharmaceuticals 6:728-758; Wang et al. (2016) Nucleic Acids Res., 44:D1087-1093). AMPs can rapidly kill invading pathogens by disrupting membranes, rendering it difficult for pathogens to develop resistance. Moreover, multiple types of AMPs could be expressed in humans to control pathogens by different mechanisms (Wang, G. (2014) Pharmaceuticals 7:545-594). In addition, these molecules can also regulate immune responses. All these properties made them appealing candidates for developing new therapies.

There is a high interest in linear AMPs because such peptides can be readily synthesized. It has been found that a 10-residue non-toxic bacterial membrane anchor can be converted to a 13-residue antibacterial peptide by extending the helix (Wang et al. (2005) J. Biol. Chem., 280:5803-5811). KR-12, corresponding to the minimal antimicrobial region of human cathelicidin LL-37, has also been identified based on NMR structural studies (Li et al. (2006) J. Am. Chem. Soc., 128:5776-5785; Wang, G. (2008) J. Biol. Chem., 283:32637-32643). 13-residue peptides against methicillin-resistant *S. aureus* (MRSA) with in vitro and in vivo efficacy have also been obtained based on the antimicrobial peptide database (APD) (Menousek et al. (2012) Int. J. Antimicrob. Agents 39:402-406; Mishra et al. (2012) J. Am. Chem. Soc., 134:12426-12429). These results imply that approximately 12-13 residues are required for helical AMPs.

Herein, shorter peptides (e.g., <10 amino acids) are provided as antibiotics or antibiofilm surfaces. This is because a short peptide can be made cost effectively. A short peptide template was identified with the aid of the APD database (Wang et al. (2016) Nucleic Acids Res., 44:D1087-1093). The temporin-SHf template possesses the highest phenylalanine content with moderate activity against MRSA (Abbassi et al. (2010) J. Biol. Chem., 285:16880-16892). To enhance the peptide activity, replacements of four phenylalanines (F) in temporin-SHf with tryptophans (W) were made as tryptophans prefer membrane interfaces (Yau et al. (1998) Biochemistry 37:14713-14718; Wang et al. (1996) Biochemistry 35:10358-10366; Khandelia et al. (2007) J. Phys. Chem. B 111:242-250). Based on these four replacements, the new peptide family is named as TetraF2W. Among the series of peptides designed, TetraF2W-RR with a pair of arginines shows higher activity against MRSA USA300 than other lysine-containing analogs. Further, the double arginine peptide is less cytotoxic to human skin and kidney cells. In addition, it is possible to covalently immobilize the most potent peptide to a polyethylene terephthalate (PET) surface, opening another use of these short peptides in preventing biofilm formation on medical devices where different microbes may exist in the same community.

Materials and Methods

Chemicals, Peptides and Surfaces

All the peptides in this study were chemically synthesized and purified to >95% (Genemed Synthesis, TX). The peptide used for surface immobilization was >90% pure. Peptides were solubilized in distilled water and their concentrations were determined by UV spectroscopy based on the Trp absorbance at 280 nm (Pace et al. (1995) Protein Sci., 4:2411-2423). The PET surfaces were purchased from Goodfellow Corporation (PA). All chemicals used in the immobilization were of analytical grade and purchased from Sigma (MO) unless specified.

HPLC Retention Time Measurements

The retention time of the peptide was measured on a Waters HPLC system equipped with an analytical reverse-phase Vydac® C18 column (4.6×250 mm). The peptide detected at 220 and 280 nm was eluted with a gradient of acetonitrile (containing 0.1% TFA) from 5% to 95% at a flow rate of 1 mL/minute (Mishra et al. (2012) J. Am. Chem. Soc., 134:12426-12429).

Peptide Parameter Calculations

Peptide molecular weight, net charge, hydrophobic content, and Boman index were calculated using the prediction tool of the antimicrobial peptide database (APD) (aps.unmc.edu/AP/prediction/prediction_main.php; Wang et al. (2016) Nucleic Acids Res., 44:D1087-1093).

Bacterial Strains

The bacterial strains used here included Gram-positive bacteria *Staphylococcus aureus* USA300 LAC, *Staphylococcus epidermidis* 1457, *Bacillus subtilis* 168, and Gram-negative *Escherichia coli* K12. Clinical strains of *S. aureus*, including Mu50, UAMS-1 and Newman, were also evaluated.

Antibacterial Assays

The antimicrobial activity of peptides was evaluated using a standard broth microdilution protocol (Wang, G. (2008) J. Biol. Chem., 283:32637-32643). In brief, exponential phase bacteria at $10^6$ CFU were incubated with serially diluted peptides overnight for ~20 hours at 37° C. The plates were read on a ChroMate® 4300 Microplate Reader at 630 nm (GMI, Ramsey, Minn.). The minimal inhibitory concentration (MIC) was defined as the lowest peptide concentration that fully inhibited bacterial growth. In addition, the effects of human serum (up to 10%), pH (6.8, 7.4 and 8.0) and 150 mM sodium chloride (NaCl) on MICs against *S. aureus* USA300 were also evaluated (Mishra et al. (2015) RSC Advances 5:59758-59769).

The minimal bactericidal concentration (MBC) was determined by plating 50 µl of the content in the clear wells of the above MIC assays. MBC was determined on the petri dishes without bacterial colony formation after overnight growth (Wang et al. (2012) Biochemistry 51:653-664).

Killing Kinetics

Killing kinetic experiments were conducted similar to antibacterial assays described above with the following modifications (Wang et al. (2012) Antimicrob. Agents Chemother., 56:845-856). Aliquots of cultures ($10^5$ CFU) treated with TetraF2W peptides were taken at 15, 30, 50, 90, and 120 minutes, diluted 100-fold, and plated on Luria-Bertani (LB) agar plates. Colonies were counted after overnight incubation at 37° C.

Membrane Permeation Measurements

Fluorescence spectroscopy was also used to follow bacterial killing. In brief, a serially diluted 10× peptide (10 µL) was made in 96-well corning COSTAR microtiter plates. Propidium iodide (2 µL) was added at 50 µM to each well which was finally incubated with *S. aureus* USA300 bacteria (88 µL at a final $OD_{600}$~0.1) with continuous shaking at 100 rpm, 37° C. in a FLUOstar® Omega (BMG LABTECH Inc, NC) microplate reader. The plates were read every 5 minutes for a total duration of 2 hours with excitation and emission wavelengths at 584 nm and 620 nm respectively. Plots were made using averaged readings from duplicated experiments after subtraction of the media control.

Confocal Laser Scanning Microscopy

The entrance of a fluorescent dye into live bacterial cells was also followed by confocal microscopy (Mishra et al. (2015) RSC Advances 5:59758-59769). In brief, *S. aureus* USA300 was grown to the exponential phase from the overnight culture. The cells were then washed twice with fresh 1×PBS (pH 7.2) and the final cell density was adjusted to $1 \times 10^8$ CFU/mL. 1500 µL of the culture was added to the chambers of cuvettes (borosilicate cover glass systems; Nunc Cat. No. 155380) with equimolar concentrations of TetraF2W-RK and fluorescein isothiocyanate FITC (9 µM). The samples were examined with a confocal laser scanning microscope (Zeiss 710) with live time series of picture taken every 5 seconds for 5 minutes and the data were processed using Zen 2010 software.

Anti-Biofilm Assays

Three types of experiments were conducted to evaluate the anti-biofilm activity of these peptides against *S. aureus* USA300, which was grown in tryptic soy broth (TSB) media in flat bottom, 96-well, polystyrene microtiter plates (Mishra et al. (2015) RSC Advances 5:59758-59769; Dean et al. (2011) BMC Microbiol., 11:114).

Inhibition of Bacterial Attachment

The first experiment measures the ability of the peptide to inhibit bacterial attachment, the initial step for biofilm formation. In short, overnight cultures of *S. aureus* USA300 were grown in TSB media to an optical density (600 nm) of ~1.0. 180 µL of this culture was added to each well of the microtiter plates containing 20 µL of 10× peptide solution. The plates are then incubated at 37° C. for 1 hour. Media with bacteria were then pipetted out and chambers were washed with 1×PBS to remove non-adherent cells. The inhibition of biofilms was estimated by XTT [2,3-bis(2-methyloxy-4-nitro-5-sulfophenyl)-2H-tetrazolium-5-carboxanilide] assay by following the manufacturer's instructions with modifications. 180 µL of fresh TSB and 20 µL of XTT solution was added to each well and the plates were again incubated for 2 hours at 37° C. Absorbance at 450 nm (only media with XTT containing wells served as the blank) was obtained using a Chromate® microtiter plate reader. Percentage of biofilm mass for the peptide was plotted assuming 100% biofilm growth is achieved on the bacterial wells without peptide treatment.

Inhibition of Biofilm Growth

The second experiment evaluates the ability of the peptide to inhibit biofilm formation of *S. aureus* USA300 in 24 hours. In brief, *S. aureus* USA300 ($10^5$ CFU/mL) was made in fresh TSB media from exponentially growing bacteria. 180 µL of this bacterial culture was added to each well of the microtiter plates containing 20 µL of 10× peptide solution. The plates were then incubated at 37° C. for 24 hours and inhibition of the biofilm formation by the peptides was quantitated using XTT as detailed above.

Preformed Biofilm Disruption

The third experiment evaluates the ability of the peptide to disrupt the biofilms of *S. aureus* USA300 formed in 24 hours. *S. aureus* USA300 ($10^5$ CFU/mL) in fresh TSB media was made from an exponentially growing culture. 200 µL of this bacterial culture was added to each well of the microtiter plates. The plates are then incubated at 37° C. for 24 hours to allow biofilm formation. Media was then carefully removed followed by washing with sterile 1×PBS to remove any unattached bacteria. Solution containing 20 µL of 10× peptide solution and 180 µL of fresh TSB were added. The plates were again incubated at 37° C. for another 24 hours. The extent of peptide disruption of biofilms was quantified using the same XTT method described above.

Confocal Microscopy of Biofilms in the Absence and Presence of Peptides

*S. aureus* USA300 ($10^5$ CFU/mL) was made from exponentially growing bacteria. 1800 µL was added to the chamber of cuvettes (borosilicate cover glass systems), and was incubated for 37° C., 24 hours for biofilm formation. Media was then pipetted out and chambers were washed with 1×PBS to remove non-adhered cells. To disrupt the preformed biofilms, 200 µL of 10× stocks of the peptide was added followed by 1800 µL of TSB. Control cuvettes contained water instead of peptide. The cuvettes were again incubated for another 24 hours at 37° C. Subsequently, the supernatant was pipetted out and the chambers were washed with 1×PBS. For evaluation under confocal microscope the biofilms were stained with 10 µL of LIVE/DEAD® kit (Invitrogen Molecular Probes) according to the manufacturer's instructions. The samples were examined with a confocal laser scanning microscope (Zeiss 710) and the data processed using Zen 2010 software.

Antifungal Assays

Fungal strains used in this study include *Candida albicans* ATCC 10231, *C. glabrata* ATCC 2001 and *C. tropicalis* ATCC 13803. The fungi were grown in Remel Dex broth (Thermo Fisher Scientific, KS). Antifungal assays were conducted essentially as described for antibacterial assays above, except for a higher starting density at an $OD_{600}$ 0.02 and a longer incubation time of ~48 hours prior to microplate reading (Mishra et al. (2015) RSC Advances 5:59758-59769).

Hemolytic Assays Using Red Blood Cells of Humans, Chickens, Pigs, and Cattle

Hemolytic analysis of selected peptides was performed using an established protocol (Mishra et al. (2015) RSC Advances 5:59758-59769). Briefly, human blood cells (UNMC Blood Bank) were washed three times with phosphate buffer saline (PBS) and diluted to a 2% solution. After peptide treatment, incubation at 37° C. for one hour, and centrifugation at 13,000 rpm, aliquots of the supernatant were transferred to a fresh 96-well microplate. To assess peptide cytotoxicity, the amount of hemoglobin released was measured at 545 nm. The percent lysis was calculated by assuming 100% release when human blood cells were treated with 1% TRITON™ X-100, and 0% release when incubated with PBS buffer. The hemolytic assays using chicken, bovine, and porcine blood cells (Lampire Biological Laboratories, Inc.) were performed in the same manner.

Cytotoxicity Assays Using Human HeLa, HEK293 and HaCaT Cells

HeLa CCL-2 epithelial adenocarcinoma cells from American Type Culture Collection (ATCC) were maintained in DMEM high glucose media with 4 mM L-glutamine (NyClone) and 100 U/mL penicillin, 100 µg/mL streptomycin (pen/strep) (Life Technologies), and 10% (v/v) inactivated fetal bovine serum (FBS) (NyClone). Cells were grown in 5% $CO_2$ at 37° C. and were detached from the culturing dish at 80% confluency using 0.025% trypsin-EDTA (NyClone) treatment. Peptide influence on the cell viability was estimated by using the MTS assay according to the manufacturer's protocol (MTS, CellTiter96® AQ One Solution Cell Proliferation Assay, Promega) with minor modifications and as described elsewhere (Mishra et al. (2015) RSC Advances 5:59758-59769). In short, cells were cultured in flat bottomed 96 well microtiter plates (Corning Life Science) at a seeding density of 20,000 cells/well. At confluence ~100% achieved after 20-24 hours of cultivation, the cells were washed twice with 100 µL Dulbecco's Phosphate Buffered Saline (Life Technologies). Further, 90 µL of DMEM media with 10% FBS, pen/step was added before exposure to 10 µL of the peptide solution in the concentration range 12.5-100 µM. Plates were incubated at 37° C. After 1 hour, 10 µL MTS, CellTiter96® was added. Plates were further incubated for another 2 hours at 37° C. and finally, the absorbance was measured on ChroMate® reader (Awareness Technology) at 492 nm. Culture medium and 0.2% SDS were used as negative and positive controls, respectively.

Human skin HaCaT (immortalized keratinocyte from AddexBio, T0020001) and kidney HEK293 cells were also cultivated for cytotoxicity evaluation of the peptides in a similar manner.

Peptide Stability to Proteases

After incubation with each protease at 37° C., peptide stability was evaluated by SDS-PAGE (Wang et al. (2014) ACS Chem. Biol., 9:1997-2002). When degraded, no peptide band could be detected on a 5% stacking/18% resolving tricine gel after 2-4 hours incubation at 37° C. Briefly, a solution (100 µL) containing 250 µM peptide and 6.25 µM protease (Sigma or Fisher) in 10 mM PBS buffer (pH 8) was incubated at 37° C. (peptide/protease molar ratio, 40:1). Aliquots (10 µL) of the reaction solutions were taken at 0, 6, and 24 hours and immediately mixed with 10 µL of 2× SDS loading buffer followed by boiling for 5 minutes to stop the reaction. For the peptide analysis, 10 µL of each sample was loaded to the well of a 5% stacking/18% resolving tricine gel. After electrophoresis, the gel was stained by Brilliant Blue R-250 (Fisher) and destained to view the peptide bands.

Site Specific Immobilization of CysTetraF2W-RR on the Polymer Surface

Polyethylene terephthalate (PET) surfaces were purchased from Goodfellow Corporation (PA). The flat surfaces were cleaned twice with ethanol and dried prior to use for any chemical reaction. Surfaces were cut into 1.0×1.0 cm rectangular pieces and irradiated with UV (Dymax Light Curing Systems, CT) at 400 W power. The sample was placed at a constant distance of 10 cm from the UV source while immersed in a solution containing 10% aqueous acrylic acid (monomer), 0.5 mM NaIO$_4$ and benzyl alcohol (0.5% v/V). UV initiated radical formation and self-polymerization of acrylic acid (AA) were carried out under this condition for 30 minutes to allow for AA-brush formation. The AA-brush functionalized PET (PET-AA) surfaces were cleaned to remove unbound monomers by washing thoroughly in water for 24 hours at 70° C. with constant stirring. Following this, the carboxyl group on the brush was activated with 1-ethyl-3-(3-dimethylaminopropyl) carbodiimide (EDC) (0.1% w/V) for 3 hours at 4° C. (Huh et al. (2001) J. Appl. Polym. Sci., 81:2769-2778). The surfaces were then washed with a copious amount of distilled water and allowed to react with chitosan (0.5 wt % of 85% deacetylated form dissolved in 0.1 M acetic acid). Chitosan reacted with the activated carboxyl group via amine forming an amide bond. The product (PET-Chi) contained multiple free amine groups that were allowed to react with an aqueous solution of 6-maleimidohexanoic acid (2 mg/mL) in the presence of EDC (0.1% w/V) for 5 hours at room temperature to produce surfaces with an exposed maleimide group (PET-Mal). Finally, an orientation specific covalent coupling of the CysTetraF2W-RR (1 mg/mL) peptide with the PET-Mal surface was accomplished in 50 mM potassium phosphate buffer pH 7.0 for 18 hours at room temperature with stirring at 60 rpm. Unbound peptides were removed by thorough rinsing with deionized water.

Biophysical Characterization of the Peptide-Coated Surface

The peptide-functionalized PET surfaces were dried before characterization by Fourier transform infrared spectroscopy (FT-IR) and X-ray photoelectron spectroscopy (XPS).

FT-IR Spectroscopy

FT-IR spectroscopy was used to monitor the successful proceedings of the immobilization of CysTetraF2W-RR onto the PET surface. The presence of signature bands in the IR spectrum confirmed the preceding reactions. The spectrum was recorded from 600 to 4000 cm$^{-1}$ by performing 20 scans on an IR Prestige-21 instrument (Shimadzu) using a Happ-Genzel apodization function.

X-Ray Photoelectron Spectroscopy (XPS)

Samples were analyzed using a Surface Science Instrument SSX-100 with an operating pressure at ~2×10$^{-9}$ Torr. Monochromatic Al K-alpha X rays (1486.6 eV) were used with a beam diameter of 1 mm. Photoelectrons were collected at a 55 degree emission angle. A hemispherical analyzer determined electron kinetic energy, using a pass energy of 150 V for wide/survey scans, and 50 V for high resolution scans. A flood gun was used for charge neutralization of non-conductive samples. Elements were identified from the survey spectra. High resolution spectra of carbon, nitrogen, oxygen and sulfur were recorded individually for elemental ratio comparison.

Measurement of the Surface CysTetraF2W-RR Concentration Using Sulfosuccinimidyl-4-o-(4,4-Dimethoxytrityl) Butyrate (Sulfo-SDTB)

The surface concentration of the covalently attached CysTetraF2W-RR was determined using a simple spectrophotometric assay. This method uses the high extinction coefficient of a complex ion formed by the reaction of the surface amino groups and Sulfo-SDTB (Gaur et al. (1989) Anal. Biochem., 180:253-258). In short, 1 mL of Sulfo-SDTB (3.0 mg/mL) solution was prepared in DMF and then made up to 50.0 mL with a 50 mM sodium bicarbonate solution (pH 8.5). 1.0 mL of this solution was added to the peptide coated PET samples and incubated for 1 hour at room temperature. The samples were then washed twice with 5.0 mL of distilled water to remove any unreacted reactant, and immersed in 2.0 mL of perchloric acid for another 30 minutes. Absorbance of the solution was measured at 498 nm to detect the DMTr cation. The number of amine groups on the surface of each sample was quantified using the Beer-Lambert law with an extinction coefficient of 70 000 M$^{-1}$ cm$^{-1}$ and finally the amount of immobilized CysTETRAF2W-RR was calculated by calibration with the predicted number of amines present in the peptide.

Antibacterial Assays of the Peptide-Coated PET Surface

Antibacterial activity of the PET-CysTetraF2W-RR samples was tested according to the published ISO 22196 protocol with minor modifications (Mishra et al. (2013) RSC Adv., 3:9534-9543; Kowalczuk et al. (2010) Int. J. Pharm., 402:175-183). In brief, the exponential phase S. aureus USA300 bacteria were adjusted to 10$^5$ CFU/mL in fresh TSB media. 20 µL of the cell suspension was added on the top of each PET surface placed in a well of a 24-well culture plate. Further, the plates were incubated at 37° C. for 2 hours, followed by addition of 280 µL of fresh TSB media. The media was mixed well to ensure all the adhered live cells to come off the surface and enter the media. 50 µL of the solution was then spread on the LB agar plates for CFU determination after 18 hour incubation. The PET surfaces that went through the series of reactions without peptide coupling were used as a negative control.

Propidium Iodide (PI) Based Membrane Permeation Assay of the CysTetraF2W-RR Coated PET Surface S. aureus USA300 was inoculated and incubated overnight in the TSB medium. Next morning, they were regrown in fresh TSB to attain the mid-exponential phase. A bacterial count of 1×10$^8$ CFU/mL was prepared in the same media. 200 µL of this culture was incubated with the PET surface with and without the peptide in a 24-well culture plate at 37° C., 150 rpm for 1 hour. For detection of bacterial permeability, a 250 µM propidium iodide (PI) solution was also added prior to incubation. Surface coated PETs without peptide were considered as a negative control. Simultaneous determination of the bacterial growth by optical density (OD$_{600}$) and PI fluorescence (excitation and emission wavelengths at 584 nm and 620 nm) caused by intercalation of the dye into the DNA of dead cells were monitored using FLUOstar® Omega (BMG LABTECH Inc, NC). Data were processed with the MARS software provided by the manufacturer.

Cellular Cytotoxicity Assessment for PET-CysTetraF2W-RR

HeLa CCL-2 cells from American Type Culture Collection (ATCC) were maintained in DMEM high glucose media with 4 mM L-glutamine (NyClone) and 100 U/mL penicillin, 100 µg/mL streptomycin (pen/strep; p/s) (Life Technologies), and 10% (v/v) inactivated fetal bovine serum (FBS, NyClone), DMEM with 10% FBS, p/s. Cells were grown in 5% CO$_2$ at 37° C. and were detached from culturing dish at 100% confluency using 0.025% trypsin-EDTA (NyClone) treatment, seeded (18,000 cells/well) in 24-well plates (Corning Life Science) and grown overnight in 200 µL DMEM media until 70% confluency. Then the old media were replaced with 500 µL of fresh DMEM media and continued to cultivate for 1 hour with the surfaces with or without peptides (1.0×1.0 cm). 200 µL of the liquid content of each well was taken out and mixed with 20 µL of MTS.

The plate was further incubated for another 2 hours at 37° C. To quantify the cytotoxicity, 100 μL of the solution was placed in a 96-well plate and the absorbance was measured on a ChroMate® reader (Awareness Technology) at 492 nm. For comparison, the same amounts of soluble peptides was used to treat them in the same way as described above. Water and 0.2% SDS were used as negative and positive controls, respectively.

Inhibition of Biofilm Formation by the Peptide-Coated Surfaces

The inhibition of the biofilm formation by the PET-CysTetraF2W-RR surface was quantified using XTT assays. Briefly, S. aureus USA300 was adjusted to $10^5$ CFU/mL. 1 mL of the culture was added to the wells of a 24-well culture plate containing surfaces that were uncoated, coated with and without the CysTetraF2W-RR peptide. The plates were then incubated at 37° C. for 24 hours to allow bacterial biofilm formation. Subsequently, media were removed and surfaces were washed three times with fresh autoclaved saline to remove any unattached cells. Fresh media containing 10% XTT solution with 1% PMS (N-Methylphenazonium methyl sulfate) were further incubated for 2 hours at 37° C. Plates were read at 450 nm for calorimetric estimation of the biofilm masses. Plots were made for various coated surfaces relative to uncoated PET surfaces, which were assumed to have reached 100% biofilm formation.

Statistical Analysis

For determining the minimal inhibitory concentrations, the experiments were conducted at least two times on different days and in duplicates wells. However, the average values were reported. For the rest of the experiments including biofilm inhibition assays, results were statistically analyzed based on paired student t-test with a two-tailed distribution with a significance level of $p<0.05$.

Results

Design and Antimicrobial Activity of Free Peptides

Design started from temporin-SHf, which is shortest in the helical family in the APD database (Wang et al. (2016) Nucleic Acids Res., 44:D1087-1093). This amphibian peptide is rich in phenylalanines (50%) with a partial helical structure bound to micelles (Abbassi et al. (2010) J. Biol. Chem., 285:16880-16892). Temporin-SHf is moderately active against E. coli ATCC 25922 and ML-35p strains (MIC 25-30 μM), but not E. coli ATCC 35218 (MIC>200 μM). It is also potent in killing Gram-positive B. megaterium (MIC 3 μM), although less effective against S. aureus ATCC 25923 (MIC 12.5 μM) (Abbassi et al. (2010) J. Biol. Chem., 285:16880-16892). In agreement with these data, a moderate activity for temporin-SHf against MRSA USA300 (MIC 25 μM) was found. Temporin-SHf appeared to possess a minimal antimicrobial sequence since it lost its activity against a panel of bacteria when a phenylalanine residue was truncated from the N-terminus. To enhance peptide activity against MRSA, this Phe-rich peptide was converted into a Trp-rich sequence, leading to a novel peptide TetraF2W (Table 1). This change was made based on the observation that tryptophans prefer the membrane interface (Yau, et al. (1998) Biochemistry 37:14713-14718; Wang et al. (1996) Biochemistry 35:10358-10366; Khandelia et al. (2007) J. Phys. Chem. B 111:242-250; Chan et al. (2006) Biochim. Biophys. Acta 1758:1184-1202; Blondelle et al. (1995) J. Appl. Bacteriol., 78:39-46). Anti-MRSA assays revealed an MIC of 3.1-6.2 μM, which is 4-8 folds more potent than temporin-SHf (Table 2). TetraF2W was also bactericidal to B. subtilis, but showed no activity against E. coli and S. epidermidis at 50-100 μM.

TABLE 1

Amino acid sequence and properties of the designed Trp-rich peptides. Peptide purity and retention time (tRP) were measured on HPLC. Molecular weight (M.Wt.), net charge, hydrophobic ratio (pho%), and Boman index of each peptide were calculated using the Antimicrobial Peptide Database prediction interface. NE: not evaluated. TetraF2W: SEQ ID NO: 1; TetraF2W-KR: SEQ ID NO: 2; TetraF2W-RK: SEQ ID NO: 3; TetraF2W-KK: SEQ ID NO: 4; TetraF2W-RR: SEQ ID NO: 5; TetraF2W-RK-d (all D-amino acids): SEQ ID NO: 6; Temporin-SHf: SEQ ID NO: 7.

| Peptide | Sequence | $t^{RP}$ (Min) | Purity (%) |
|---|---|---|---|
| Temporin-SHf | FFFLSRIF | 14.267 | 97.41 |
| TetraF2W | WWWLSRIW | 14.539 | 98.33 |
| TetraF2W-KR | WWWLKRIW | 13.657 | 95.62 |
| TetraF2W-RK | WWWLRKIW | 13.682 | 96.56 |
| TetraF2W-KK | WWWLKKIW | 13.586 | 96.03 |
| TetraF2W-RR | WWWLRRIW | 13.821 | 96.88 |
| TetraF2W-RK-d | wwwlrkiw | NE | 97.92 |

| M.Wt. | Net Charge | Pho% | Boman index |
|---|---|---|---|
| 1076.3 | +2 | 75 | −0.42 |
| 1232.5 | +2 | 75 | −0.10 |
| 1273.5 | +3 | 75 | 0.16 |
| 1273.5 | +3 | 75 | 0.16 |
| 1245.5 | +3 | 75 | −1.00 |
| 1301.6 | +3 | 75 | 1.33 |
| 1273.5 | +3 | 75 | 0.16 |

TABLE 2

Antibacterial activities of new Trp-rich peptides designed based on a natural template.

| | MIC (μM) | | |
|---|---|---|---|
| Peptide | E. coli K12 | S. epidermidis 1457 | B. subtilis 168 |
| Temporin-SHf | >100 | >100 | >100 |
| TetraF2W | >100 | >50 | 6.2 |
| TetraF2W-KR | 12.5-25 | 12.5 | 6.2 |
| TetraF2W-RK | 25 | 6.2 | 6.2 |
| TetraF2W-KK | 12.5-25 | 6.2 | 6.2 |
| TetraF2W-RR | 25 | 6.2-12.5 | 3.1-6.2 |
| TetraF2W-RK-d | 6.2 | 6.2 | 3.1 |

| S. aureus USA300 | MBC (μM) S. aureus USA300 |
|---|---|
| 25 | NE[1] |
| 3.1-6.2 | 6.2 |
| 3.1 | 12.5 |
| 3.1 | 12.5 |
| 3.1-6.2 | >25 |
| 1.6-3.1 | 3.1 |
| 3.1 | 12.5 |

NE: not evaluated.

Next, the polar S5 amino acid was changed to basic K5 to increase peptide solubility in water. Interestingly, the new peptide TetraF2W-KR (Table 1) gained activity against both E. coli K12 and S. epidermidis, indicating the importance of the basic lysine in inhibiting these two bacteria strains. To find the best basic pair, other peptides were made by replacing the RK pair with RK, KK, or RR (Table 1). These four peptides containing varying basic pairs showed similar antibacterial activity against E. coli, S. epidermidis, B. subtilis, and S. aureus USA300 in terms of MIC (Table 2). Notably, these peptides were able to inhibit clinical strains of S. aureus (Mu50, Newman, and UAMS-1) at 3-6 μM (Table 3). Although the four dibasic TetraF2W peptides had similar MIC values against bacteria, they showed different minimal bactericidal concentrations (MBCs) against *S. aureus* USA300 (Table 2). While TetraF2W-RR was most potent (MBC 3.1 µM), TetraF2W-KK was weakest (MBC>25 µM).

TABLE 3

Antimicrobial activities (in µM) of short Trp-rich peptides against *Staphylococcus aureus* clinical strains. The community-isolated *S. aureus* strain USA300 is used for comparison.

| Peptide | Mu50 | Newman | UAMS-1 | USA300 |
|---|---|---|---|---|
| TetraF2W-KK | 6.2 | 6.2 | 6.2 | 3.1-6.2 |
| TetraF2W-KR | 6.2 | 3.1-6.2 | 6.2 | 3.1 |
| TetraF2W-RK | 3.1 | 3.1 | 6.2 | 3.1 |
| TetraF2W-RR | 3.1 | 3.1 | 6.2 | 1.56-3.1 |

Since serum, salts, and pH can influence peptide activity, the effects of these factors on peptide activity against *S. aureus* USA300 were tested (Mishra et al. (2015) RSC Advances 5:59758-59769). The results are given in Table 4. Compared to the MIC values obtained in normal TSB (pH 7.4), the peptide activity was reduced by 4-8 folds in the presence of 5% human serum, probably due to association with serum proteins. However, these peptides were able to tolerate a change in pH. A drop of pH from 8 to 6.8 only caused a two-fold change in MIC for the three arginine-containing peptides (TetraF2W-RR, TetraF2W-RK and TetraF2W-KR). TetraF2W-KK, however, appeared to be more susceptible as its MIC reduced from 3.1 to 12.5 µM. This fact sheds light on the preferred Arg-Trp combinations in known Trp-rich peptides (Chan et al. (2006) Biochim. Biophys. Acta 1758:1184-1202). In addition, all TetraF2W peptides remained active (3.1-6.2 µM) even after the addition of 150 mM NaCl. Thus, these TetraF2W peptides, especially the RR variant, are resistant to salts and pH under the testing conditions.

TABLE 4

Serum, salt, and pH on antimicrobial activities (in µM) of TetraF2W dibasic variants against *S. aureus* USA300.

| Peptide | pH 8 | Normal medium (pH 7.4) |
|---|---|---|
| TetraF2W-KK | 3.1 | 3.1-6.2 |
| TetraF2W-KR | 3.1 | 3.1 |
| TetraF2W-RK | 3.1 | 3.1 |
| TetraF2W-RR | 3.1 | 1.56-3.1 |
| pH 6.8 | 150 mM NaCl | 5% Serum |
| 12.5 | 3.1-6.2 | 12.5 |
| 6.2 | 3.1 | 25 |
| 6.2 | 3.1 | 12.5 |
| 6.2 | 3.1 | 25 |

The candidacidal ability of the four peptides was also tested (Table 5). In contrast to the bacterial cases, TetraF2W-RR was poorest against *C. albicans, C. glabrata* and *C. tropicalis* and TetraF2W-KK was most active. The RK and KR pair showed identical antifungal activities in all the cases.

TABLE 5

Antifungal activities of Trp-rich TetraF2W peptides (MIC in µM).

| Peptide | Candida albicans | Candida glabrata | Candida tropicalis |
|---|---|---|---|
| TetraF2W-KK | 6.2 | 6.2-12.5 | 1.6 |
| TetraF2W-KR | 12.5 | 12.5 | 3.1-6.2 |
| TetraF2W-RK | 12.5 | 12.5 | 3.1-6.2 |
| TetraF2W-RR | 25 | >25 | 3.1 |

Mechanism of Action of the Short Trp-Rich Peptides

Figure 1A:
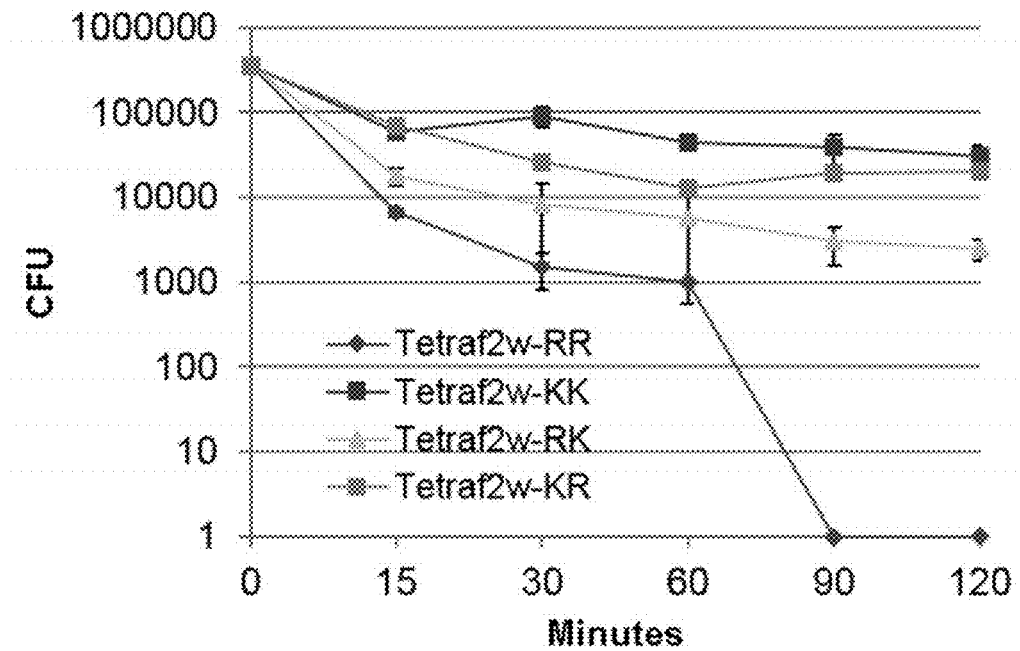

To further compare the potency of the new Trp-rich peptides, traditional killing experiments were conducted based on colony counting. The order of *S. aureus* USA300 killing rate is TetraF2W-RR>TetraF2W-RK>TetraF2W-KR>TetraF2W-KK (FIG. 1A). Thus, TetraF2W-RR showed the fastest killing and all the bacteria ($10^5$ CFU) were killed in 90 minutes. The rapid killing implies that the peptide targeted bacterial membranes (Zasloff, M. (2002) Nature 415:389-395).

Figure 1B:
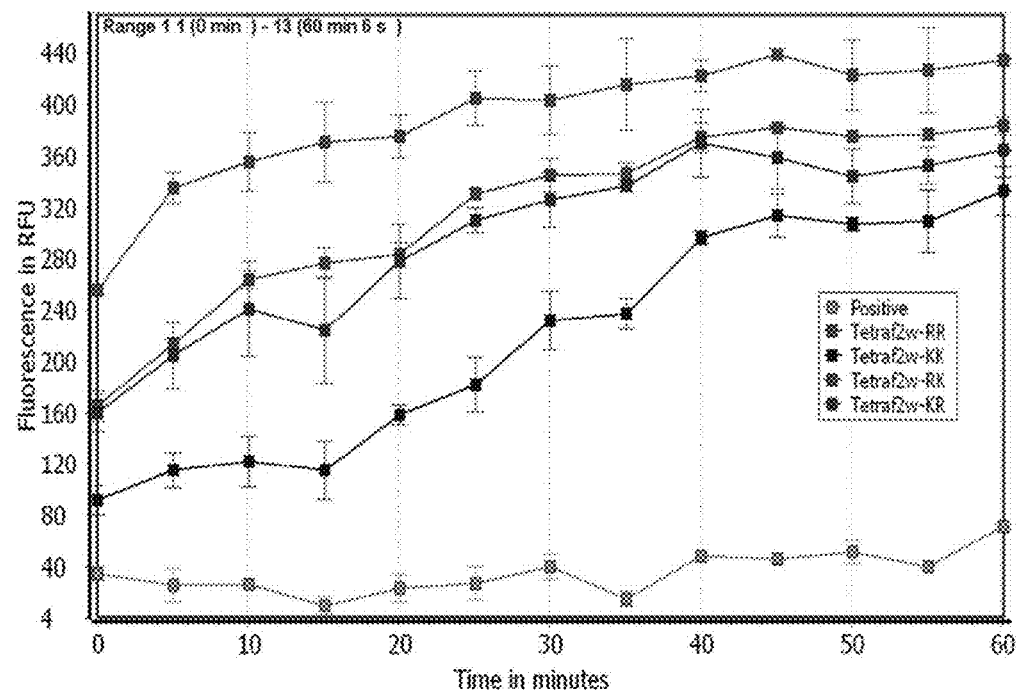

To confirm membrane targeting, the fluorescence change after peptide treatment of *S. aureus* USA300 was followed in the presence of propidium iodide, which does not fluoresce until bacterial membranes are compromised. This approach was validated by using a set of antibiotics with known mechanisms of action. While there is no increase in fluorescence when treated with vancomycin (cell wall targeting), a rapid increase in fluorescence occurs when treated with membrane-active daptomycin. The intensity of fluorescence was in the order of TetraF2W-RR>TetraF2W-KR~TetraF2W-RK>TetraF2W-KK (FIG. 1B). Thus, the peptide with the RR basic pair was most effective in damaging the membranes of *S. aureus*, whereas the peptide with the KK pair was least potent. The RK and KR peptides were found to have more or less similar potency in membrane permeation. Therefore, the results obtained here based on fluorescence spectroscopy are consistent with killing kinetics from colony counting obtained above, verifying that TetraF2W-RR is the most active peptide.

Since these four TetraF2W peptides (KK, KR, RK, and RR) are quite similar, they may work by a similar mechanism. To validate the membrane targeting of these peptides, a different member TetraF2W-RK in this peptide series was selected and it was incubated with live *S. aureus* USA300 in the presence of a different dye FITC. Again, a time dependent increment of fluorescence was observed by confocal microscopy. FITC entered the cells rapidly and the majority of cells became visible in the window in 30 seconds. The image at 115 seconds looked almost identical to those recorded at 295 seconds. This experiment also indicates that bacterial membranes were damaged by the peptide, opening the door to FITC (Oren et al. (1998) Biopolymers 47:451-463).

To provide additional insight, the MIC values of TetraF2W-RK synthesized using either entirely L-amino acids (normal one) or entirely D-amino acids were compared. In the cases of three Gram-positive bacteria such as *S. epidermidis, B. subtilis*, and *S. aureus*, the D-form peptide displayed an MIC similar to the L-form (Table 2). Because the L and D-forms are mirror-imaged to each other, this result indicates that a chiral molecule is not involved in the peptide action, further confirming membrane targeting of this peptide against the panel of Gram-positive bacteria (Chan et al. (2006) Biochim. Biophys. Acta 1758:1184-1202; Mishra et al. (2012) J. Am. Chem. Soc., 134:12426-

12429). However, rather different MIC values were obtained in the case of Gram-negative *E. coli* (25 µM for the L-form vs. 6.2 µM for the D form) (Table 2), indicating that TetraF2W-RK might have inhibited the growth of *E. coli* by a different mechanism.

Anti-Biofilm Activity of TetraF2W-RR

Figure 2A:
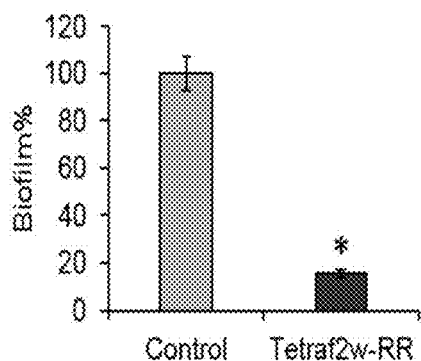
Figure 2B:
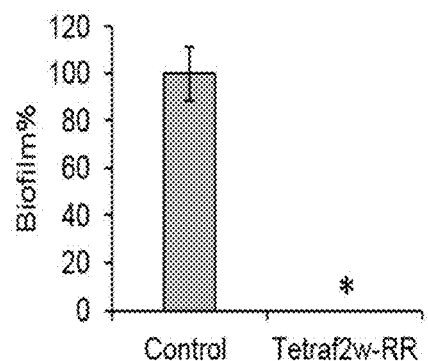
Figure 2C:
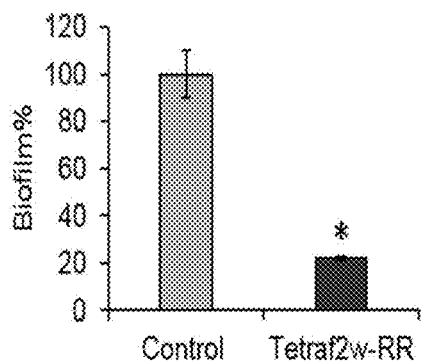
Figure 2D:
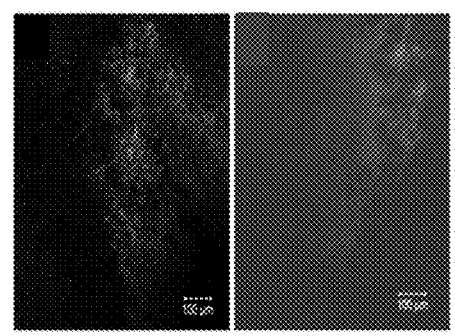

In many settings, bacteria live together in the form of biofilms, where the community works together in a house covered with polysaccharides, DNA, and/or proteins. Such a community of bacteria poses challenge to medical treatment. Therefore, an anti-biofilm property of the designed peptide is desired. The TetraF2W-RR peptide exhibited excellent anti-biofilm activity against *S. aureus* USA300 (FIG. 2). TetraF2W-RR could reduce the adherence of the bacterial cells by 83% at 25 µM (FIG. 2A). Surface adherence is regarded as the first step for biofilm formation. Furthermore, it actively inhibited biofilm growth even at 6.25 µM. As shown in FIG. 2B, the peptide completely inhibited the biofilm formation at 25 µM. Finally, TetraF2W-RR disrupted ~77% of the preformed biofilms at 25 µM (FIG. 2C). To visualize the peptide effect on biofilms, confocal laser scanning microscopy was utilized to view the 24 hours preformed biofilms after treatment with 25 µM of TetraF2W-RR (FIG. 2D). The cells in the biofilms were stained with a LIVE/DEAD® Kit. In FIG. 2D, live cells stained with the SYTO9 dye became green (left), while the dead cells, after staining with a DNA-binding dye propidium iodide, turned red (right). Hence, TetraF2W-RR is capable of killing *S. aureus* USA300 in 24 hour biofilms preformed on the 96-well tissue culture treated sterile polystyrene plate.

Cytotoxicity of Free Peptides

Figure 2E:
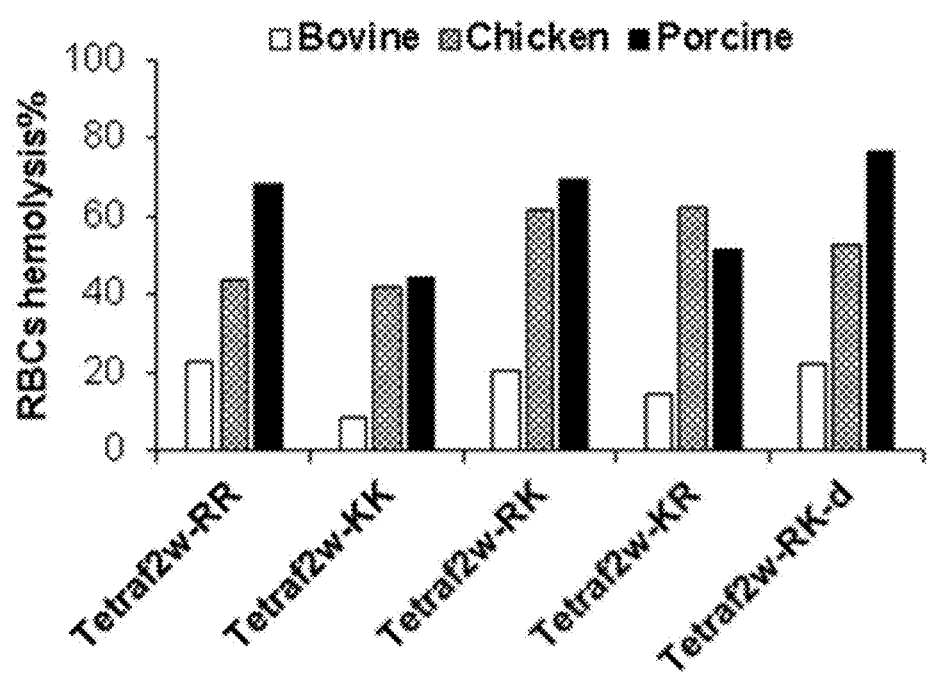

To develop peptide therapeutics, cytotoxicity to mammalian cells must be minimized. To better evaluate the cytotoxicity of these peptides, a variety of eukaryotic cells were utilized. As shown in Table 6, TetraF2W peptides gave similar 50% lytic concentrations ($LC_{50}$) (Mishra et al. (2015) RSC Advances 5:59758-59769). The susceptibility of different types of animal blood cells was compared to these new Trp-rich peptides and the $LC_{50}$ values are also given in Table 6. Overall, similar 50% hemolytic concentrations (HL50) were observed, although TetraF2W-RR appeared to be slightly more toxic than TetraF2W-KK in the cases of human and porcine blood cells. To further compare the results for the three animal blood cells, cell lysis was plotted at 50 µM (FIG. 2E). It seems that the porcine blood cells were most susceptible with 50-80% lysis. The chicken blood cells were slightly less lysed with 40-60% lysis, while the bovine blood cells were least lysed (10-20%). Thus, blood cells have different susceptibility to these peptides with porcine results more similar to humans.

TABLE 6

Hemolytic abilities ($LC_{50}$ µM) of new Trp-rich peptides TetraF2W using different animal blood cells and human cells.

| Peptide | TetraF2W-KK | TetraF2W-KR | TetraF2W-RK | TetraF2W-RR |
|---|---|---|---|---|
| Human RBCs | 40 | 30 | 30 | 20 |
| Porcine RBCs | 55 | 50 | 40 | 40 |
| Chicken RBCs | 50 | 35 | 35 | 55 |
| Human HEK293 | 50 | 55 | 60 | 70 |
| Human HaCaT | 50 | 60 | 60 | 70 |
| Human HeLa | 70 | 100 | >100 | 60 |

To better measure peptide cytotoxicity, additional human cell lines were utilized: HeLa, HaCaT and HEK293. While HeLa cells are cancer cells, HaCaT and HEK293 are normal human skin and kidney cells, respectively. In the case of HeLa cells, the following lytic order was found: TetraF2W-RR~TetraF2W-KK>TetraF2W-KR~TetraF2W-RK (FIG. 3A). A different cytotoxicity order was observed for human HaCaT (FIG. 3B) and HEK293 (Table 6) cells: TetraF2W-KK>TetraF2W-RK~TetraF2W-KR>TetraF2W-RR. These results revealed small differences in peptide cytotoxicity depending on cell types. Note that the less toxic effects of the arginine variant on both HaCaT and HEK293 cells would make the TetraF2W-RR peptide more selective than the lysine analog.

Stability of Free Peptides to Select Host and Pathogen Proteases

Figure 4:
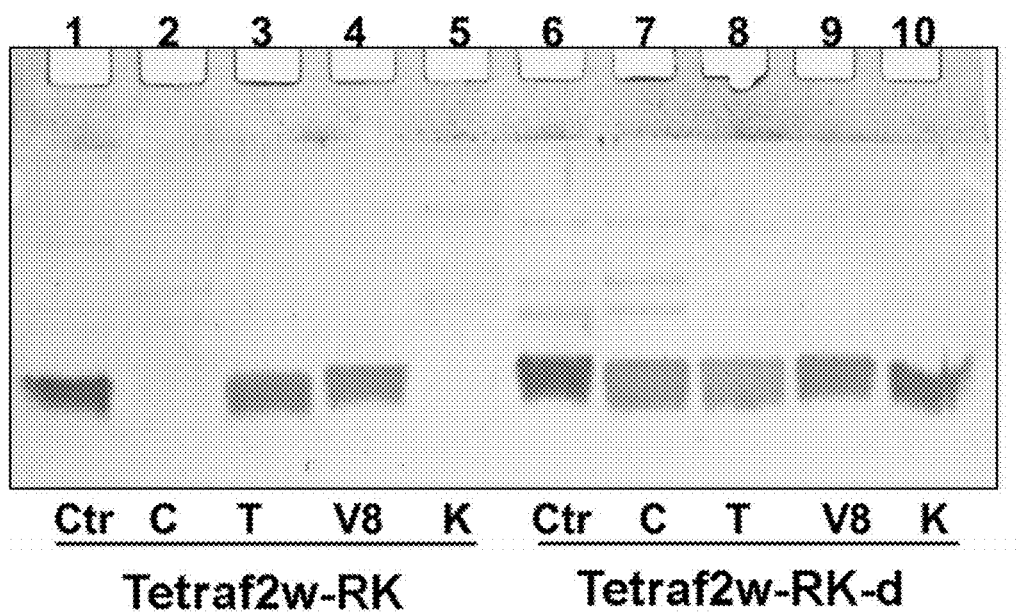
FIG. 4 shows the peptide stability comparison of the L- and D-forms of TetraF2W-RK after 24 hour incubation with chymotrypsin, trypsin, *Staphylococcus aureus* V8 protease, or proteinase K, which are represented with C, T, V8, and K, respectively.

Because the L and D forms of peptides are known to have different stability to proteases (Mishra et al. (2012) J. Am. Chem. Soc., 134:12426-12429; Bessalle et al. (1990) FEBS Lett., 274:151-155; Merrifield et al. (1995) Int. J. Pept. Protein Res., 46:214-220), the digestion of TetraF2W-RK by a set of important proteases from both host and pathogens was studied. This includes mammalian chymotrypsin, trypsin, *S. aureus* V8 protease, and fungal proteinase K. Interestingly, the L-form of TetraF2W-RK was not cut by trypsin and the *S. aureus* V8 protease at a peptide:protease molar ratio of 40:1, although it was completely degraded by chymotrypsin and fungal proteinase K in 24 hours. In the case of the D-form, TetraF2W-RK remained stable to all the proteases tested here (FIG. 4). Thus, TetraF2W-RK has inherent stability to trypsin and the *S. aureus* V8 protease, and became even more stable when made in D-amino acids.

Covalent Immobilization of CysTetraF2W-RR on the PET Surface

FIG. 5 depicts a schematic diagram for the immobilization of CysTetraF2W-RR onto the PET surface. A cysteine residue was appended at the N-terminus of the peptide (i.e., CysTetraF2W-RR) to allow for coupling to the surface via the maleimide-cysteine reaction. To increase peptide coating density, "brushes" were generated on the PET surface through irradiation with high energy UV. The transfer of UV-generated radicals led to the formation of acrylic acid polymers (brushes) with protruding carboxyl groups, which were further activated by EDC. These activated carboxylic functional groups were then coupled to amine groups of chitosan via forming an amide bond. Since chitosan is a long chain polymer, it was used as a spacer to increase the chance for the coupled peptide to remain antimicrobial. Next, 6-maleimidohexanoic acid was coupled with an amide group of chitosan. This coupling generated free maleimide groups on the surface for site-directed peptide coupling via the sulfhydryl group of the N-terminal cysteine of TetraF2W-RR at pH 7. In the following, physical, chemical, and biological evidence for the success coating of the peptide are provided.

Characterization of the PET-CysTetraF2W-RR Surface

FT-IR and XPS analysis of the immobilized CysTetraF2W-RR. Each chemical reaction toward peptide coupling was monitored by FT-IR based signature peaks generated (FIG. 6A). The grafting of acrylic acid brush lead to a broad band at 1718 cm$^{-1}$ characteristic of stretching absorption band of the carbonyl group C=O, and weak vibration bands at 1456 cm$^{-1}$ corresponding to the —CH$_2$— group. The coupling between the in-plane OH bending and C—O stretching vibration of neighboring carboxyl group generated the bands at 1248 cm$^{-1}$ and 1174 cm$^{-1}$, respectively (Moharram et al. (2002) J. Applied Polymer Sci., 85:1619-1623). The chitosan and maleimide coupling to the surface generated the 1080 cm$^{-1}$ band typical for glucopyranose form chitosan (Costa et al. (2015) Biomaterials 52:531-538) and the increment of the 1718 cm$^{-1}$ band for additional C=O groups from the acetylated chitosan and maleimide units. Subsequent peptide immobilization led to the increment of the amide I stretching band at 1650 cm$^{-1}$ which was hidden in the shoulder of 1718 cm$^{-1}$ and is now more prominent. Further, the band at 1560 cm$^{-1}$ corresponds to the amide II from the immobilized CysTetraF2W-RR. These spectral signatures convey a strong evidence for the successful proceedings of the reactions to the final product.

An elemental composition analysis of the reaction product by XPS revealed wide range spectra for the N 1s, C 1s, O 1s and S 2p electrons. Since sulfur is only present in the peptide, the S 2p peak appearing around 164 eV (FIG. 6B) would support a successful grafting of the CysTetraF2W-RR peptide onto the PET surface. While the peak intensity for sulfur is low, the success of peptide coupling to the PET surface is also supported by other experiments below.

The immobilized peptide was quantified by using a simple calorimetric method that estimates the amount of free amino group on the surface. The Sulfo-SDTB reacts specifically with the free surface amino group and produces a complex, which on further acid treatments breaks to form a 4,4'-dimethoxytrityl cation (DMTr ion). This ion has a strong absorbance at 498 nm with a high extinction coefficient of 70,000 M$^{-1}$ cm$^{-1}$ (Gaur et al. (1989) Anal. Biochem., 180: 253-258). Based on the amounts of free amine present in the peptide, the amount of peptide tethered was back calculated. Since chitosan also have free amino groups, its contribution ($6.92\pm1.10\times10^{-10}$ mol cm$^{-2}$) had to be deducted from the total amount of amino groups. The coating density of CysTetraF2W-RR was found to be $2.81\pm0.68\times10^{-10}$ mol cm$^{-2}$.

To demonstrate surface activity, both traditional killing experiments based on a modified ISO 22196 protocol and fluorescence-based monitoring of dead bacteria were conducted. The PET-CysTetraF2W-RR surface was found to have excellent biocidal properties against S. aureus USA300. In the traditional colony counting assay, it eradicated about 95% of live bacteria compared to the control surface without peptide immobilization (FIG. 7A). In another assay where the surface was incubated with more bacteria, they did not allow any further growth and reduced the overall bacterial burden, too. While the bacterial growth (OD$_{600}$) showed a 1.5-fold increment for the surface devoid of peptide, the CysTetraF2W-RR coated PET surface decreased the growth by 40% (FIG. 7B). This observation was also validated by an increase in the PI fluorescence (FIG. 7C), which corresponds to a drop in OD$_{600}$ measured in the same experiment. The increase in the PI fluorescence here is reminiscent of the previous observation with the same peptide in the free form (FIG. 1B). Thus, the immobilized peptide also killed S. aureus via membrane permeation.

The cytotoxicity of the peptide immobilized surface was also studied. When 1 cm$^2$ of the TetraF2W-RR peptide coated surface was incubated with HeLa CCL-2 cells for an hour, no change in the percentage of live cells was observed (FIG. 7D), confirming that the surface was not toxic to these cells. Under the same conditions, an equivalent amount of free peptide CysTetraF2W-RR was also nontoxic (FIG. 7D).

FIG. 8 shows the outcome of anti-biofilm assays using the peptide coated surface. The PET-CysTetraF2W-RR surface reduced the formation of biofilm of S. aureus USA300 by 70% after 24 hour incubation. On contrary, there was no significant change in the biofilm mass formed on the uncoated PET surface, or the surface that went through the same chemistry without the last step of peptide coupling. Hence, the reduction in biofilms could be attributed to the effect of the covalently attached peptide, rather than other chemicals, including chitosan, that facilitate the coupling of the peptide to the PET surface.

There is a great interest in developing AMPs into therapeutic molecules (Boman, H. G. (2003) J. Intern. Med., 254:197-215; Hancock et al. (2006) Nat. Biotechnol., 24:1551-1557). Short peptides occupy an important niche because they may be made cost effectively (Mishra et al. (2010) Amino Acids 39:1493-1505; Mangoni et al. (2011) Cell Mol. Life Sci., 68:2267-2280). The construction of the APD database facilitates peptide discovery (Wang et al. (2016) Nucleic Acids Res., 44:D1087-1093; Wang et al. (2010) Antimicrob, Agents Chemother., 54:1343-1346). With the aid of the database, a family of short Trp-rich peptides based on a Phe-rich temporin-SHf template was generated (Abbassi et al. (2010) J. Biol. Chem., 285:16880-16892). The TetraF2W peptides contain only eight residues with 50% Trp, higher than those in known Trp-rich peptides (Wang et al. (2016) Nucleic Acids Res., 44:D1087-1093; Chan et al. (2006) Biochim. Biophys. Acta 1758:1184-1202). In particular, the anti-Staphylococcal activity of the double arginine variant TetraF2W-RR increased by 8 fold, emerging as the most potent peptide for killing MRSA (MBC 3.1 µM in Table 2). To elucidate the molecular basis for this, it was found that the MBCs of the four TetraF2W variants corresponded exactly to their HPLC retention times. It indicates that the double RR variant is slightly more hydrophobic than the lysine-containing peptides (Table 1), explaining its more efficient MRSA-killing ability (Table 2). Likewise, the Boman index also correlates with MBC of these peptides. Because Boman index was derived from the partition coefficient of the peptide between water and cyclohexane (Boman, H. G. (2003) J. Intern. Med., 254:197-215; Radzicka et al. (1998) Biochemistry 27:1664-1670), it is related to peptide hydrophobicity as well. Interestingly, in a combined classification of 20 amino acids based on 144 hydrophobic scales, arginine appears in the hydrophobic amino acid group, whereas lysine is located in the hydrophilic group (Trinquier et al. (1998) Protein Eng., 11:153-169). The more efficient killing of the arginine variant is also attributed to the bifurcated hydrogen bonding ability of arginines (Hart et al. (1987) Biochem. Biophys. Res. Commun., 146:346-353; Nguyen et al. (2011) Biochim. Biophys. Acta. 1808:2297-2303; Schmidt et al. (2011) J. Am. Chem. Soc., 133:6720-6727). It is also likely that the cation of the arginine side chain interacts with the π electron of aromatic amino acids (Chan et al. (2006) Biochim. Biophys. Acta 1758:1184-1202). Such unique properties may explain why arginines are preferred in short Trp-rich peptides obtained from combinatorial libraries (Blondelle et al. (1995) J. Appl. Bacteriol., 78:39-46). Of particular interest is the finding that the arginine variant tends to be more potent against bacteria, but less cytotoxic to select human cells than the lysine-containing analogs. Such a Trp-Arg combination would lead to a more selective defense molecule, revealing a fundamental design principle for Trp-rich AMPs.

The growth of biofilms on medical devices constitutes a difficult-to-treat problem in hospitals, especially when different microbes are involved. To prevent biofilm formation, the most potent peptide TetraF2W-RR was coated to the PET surface, which is widely used in medical devices. A surface with anti-biofilm ability may get rid of the need to replace infected medical implants. Chitosan was used as a linker here, which was insufficient by itself to exert the anti-biofilm property (FIG. 8). Additionally, brush-based chemistry was also utilized, which is advantageous because it can increase coating density of anti-biofilm peptides (Jiang et al. (2013) Chem. Soc. Rev., 42:3394-3426). It has been found that coating more of the hLf1-11 peptide to titanium via surface-initiated atom transfer radial polymerization better reduced bacterial attachment than the silanization method (Godoy-Gallardo et al. (2015) Biomacromolecules 16:483-496). Coating of a 13mer GL13K peptide also made the titanium surface an anti-biofilm (Chen et al. (2014) PLoS One 9:e111579). Likewise, immobilization of a 15mer lasioglossin LL-III to silicone catheters conferred antibiofilm ability to the device (Mishra et al. (2014) J. Mater. Chem. B 2:1706-1716). It has been shown that synthetic lactams could also inhibit the growth of Streptococcus mutans on titanium (Xavier et al. (2016) Mater. Sci. Eng. C Mater. Biol. Appl., 68:837-841).

The design of shorter AMPs (8mers) for coating has a practical consequence because such peptides can be made more cost effectively than long peptides. It is also advantageous that the designed peptide disrupted S. aureus USA300 membranes both in the free and immobilized forms. Such a mechanism of action renders it difficult for this superbug to develop resistance to the newly designed compound (Hancock et al. (2006) Nat. Biotechnol., 24:1551-1557; Zasloff, M. (2002) Nature 415:389-395; Wang et al. (2015) Pharmaceuticals 8:123-150). Surface immobilization of antimicrobial peptides offers other advantages such as decrease in potential cytotoxicity and increase in lifetime of the peptide (Godoy-Gallardo et al. (2015) Biomacromolecules 16:483-496; Chen et al. (2014) PLoS One 9:e111579). Significantly, such coated surfaces can relieve the pain and cost of patients and the burden of doctors in replacing infected medical devices.

In summary, a group of new Trp-rich antibacterial peptides are provided based on the shortest helix template in the antimicrobial peptide database. Compared to the temporin-SHf template, the designer peptide gain 8-fold potency against MRSA USA300. The potency of the double arginine peptide TetraF2W-RR is attributed to its increased hydrophobicity than other dibasic analogs containing KK, KR, or RK pairs. Importantly, at the Staphylococcal killing concentration (3 µM), none of these short peptides would be toxic to the host. In addition, these short Trp-rich peptides also possess inherent stability to select proteases and are easy to synthesize chemically, making them attractive templates for developing new antimicrobials to combat MRSA. Thus, an important design principle of Trp-rich AMPs was elucidated—that a combination of Trp and Arg appears to generate a needed advantage: potency against invading microbes, but low cytotoxicity to the host.

Covalent immobilization of TetraF2W-RR onto the polymer surface prevents bacterial biofilm formation. Notably, the peptide after immobilization kills S. aureus USA300 in the same mechanism as the free TetraF2W-RR by disrupting bacterial membranes. Thus, these short peptides can be used as antimicrobials to treat patients and biofilm-resistant agents coated on the surfaces of implanted medical devices.

Example 2

Biofilm-related infections on implanted medical devices are a challenging issue (Darouiche, R. O. (2004) New Eng. J. Med., 350:1422-1429). Such infections can cause implant failures, increase treatment costs, and lead to high morbidity and mortality (Zhao et al. (2009) J. Biomed. Mater. Res. B Appl. Biomater., 91B:470-480; Xavier et al. (2016) Mater. Sci. Eng. C Mater. Biol. Appl., 68:837-841). Therefore, the best strategy is to prevent such infections (Costa et al. (2011) Acta Biomater., 7:1431-1440; Onaizi et al. (2011) Biotechnol. Adv., 29:67-74). One promising method is to coat antimicrobials on the biomaterial surface. In the past years, both metals (e.g., silver, zinc, copper, and zirconium) and non-metals (e.g., selenium and antibiotics) have been used for coating (Gallo et al. (2014) Int. J. Mol. Sci., 15:13849-13880). The effective use of metals such as silver is complicated by leaching and cytotoxicity issues. However, a prolonged use of antibiotics results in reduced efficacy due to the emergence of multi-drug resistant pathogens (Zhao et al. (2009) J. Biomed. Mater. Res. B Appl. Biomater., 91B: 470-480; Knetsch et al. (2011) Polymers 3(1):340-366).

Antimicrobial peptides (AMPs), currently with over 2,800 entries in the antimicrobial peptide database (website: aps.unmc.edu/AP), are potent against resistant pathogens. They possess promising characteristics such as membrane disruption, rapid killing, immune modulation, and wound healing (Zasloff, M. (2002) Nature 415(6870):389-395; Wang, G. ed. (2017) Antimicrobial peptides: discovery, design and novel therapeutic strategies. Oxfordshire (UK): CABI, $2^{nd}$ version). The field is moving forward rapidly with ~100 new naturally occurring AMPs discovered annually from the six kingdoms of life (Wang et al. (2015) Pharmaceuticals 8:123-150; Wang et al. (2016) Nucleic Acids Res., 44(D1):D1087-D1093). To date, >100 AMPs have been documented from humans alone (Wang et al. (2014) Biochim. Biophys. Acta., 1838:2160-2172; Wang et al. (2014) ACS Chem. Biol., 9:1997-2002). While multiple defensins have been identified, there is only one cathelicidin gene found in humans. LL-37, a 37-residue antimicrobial peptide starting with a pair of leucines, is one of the mature peptides released from the precursor of human cathelicidin. LL-37 is known to have broad-spectrum antimicrobial activity against bacteria, viruses, fungi, and parasites. In addition, it has wound healing, immune modulating, and anticancer effects (Durr et al. (2006) Biochim. Biophys. Acta., 1758: 1408-1425; Wang et al. (2014) Biochim. Biophys. Acta., 1838:2160-2172; Wang et al. (2014) ACS Chem. Biol., 9:1997-2002). Antimicrobial peptides are attractive as new coating agents to prevent microbial infection. The peptides can be surface coated noncovalently or covalently. While the non-covalent approach deals with surface adsorption of AMPs, the covalent immobilization method holds the molecule strongly onto the surface. Consequently, covalent immobilization is preferred because molecules coated in this manner are unlikely to leach into the surrounding environment (Santos et al., (2013) ACS Appl. Mater. Interfaces 5:12789-12793). It is noticed that in covalent linking, the orientation of the peptide can be crucial. Site-specific immobilization of AMPs that keeps the peptide backbone intact is advantageous to random adsorption (Gabriel et al. (2006) Bioconjug. Chem., 17:548-550; Mishra et al. (2014) Mater. Chem. B 2:1706-1716). Indeed, some AMPs have been immobilized on polymeric and metal surfaces, including silicone, polyethylene terephthalate, silicon, titanium, and stainless steel, and were found to possess antibacterial and anti-biofilm characteristics (Costa et al. (2011) Acta Biomater. 7:1431-1440). For instance, cecropin B (Xu et al. (2013) Colloids Surf. B Biointerfaces 110:225-235) and hLf1-11, human lactoferrin-derived AMP (Godoy-Gallardo et al. (2014) Acta Biomater., 10:3522-3534), are effective in reducing bacterial adhesion and biofilm formation of Bacillus subtilis, Staphylococcus aureus, Escherichia coli, Pseudomonas aeruginosa, Streptococcus sanguinis and Lactobacillus salivarius. Tet213 (sequence KRWWKWWRRC; SEQ ID NO: 8) inhibits the growth of S. aureus and P.

aeruginosa (Kazemzadeh-Narbat et al. (2013) Biomaterials 34:5969-5977). Note that the treatment of polymicrobial biofilms could be more challenging due to the co-aggregation of microorganisms.

Titanium is widely used in dental and orthopedic implants because of its excellent mechanical strength, corrosion resistance, and biocompatibility (Bauer et al. (2013) Antimicrob. Agents Chemother., 57:2726-2737; Godoy-Gallardo et al. (2014) Acta Biomater., 10:3522-3534). However, its use is limited due to ease of bacterial colonization, causing subsequent infection (Pye et al. (2009) J. Hosp. Infect., 72:104-110). Human cathelicidin LL-37 has been immobilized onto the titanium surface with retained antibacterial activity (Gabriel et al. (2006) Bioconjug. Chem. 17:548-550). However, human LL-37 is relatively long with 37 amino acids, and can be costly to synthesize chemically. Thus, there is a desire to shorten LL-37 by removing unwanted regions. Several fragments of LL-37 (e.g., P10, P60.4Ac, FK-16, IG-25, KR-12, KS-30, and KR-20) have since been evaluated with the goal of identifying better antimicrobial and anti-biofilm properties (Durr et al. (2006) Biochim. Biophys. Acta. 1758:1408-1425; Feng et al. (2013) Peptides 49:131-137; Wang et al. (2014) Biochim. Biophys. Acta 1838:2160-2172). Among them, FK-16 is the major antimicrobial fragment corresponding to residues 17-32 of human LL-37 (Li et al. (2006) J. Am. Chem. Soc., 128:5776-5785). GF-17, a glycine-appended FK-16 peptide (Wang et al. (2012) Antimicrob. Agents Chemother., 56:845-856), is more active than the full-length LL-37 against both planktonic and biofilm formed S. aureus (Mishra et al. (2016) ACS Med. Chem. Lett., 7:117-121). KR-12, the same minimal antimicrobial peptide of LL-37 (Wang, G. (2008) J. Biol. Chem., 283:32637-32643), has also been immobilized (Nie et al. (2016) RSC Adv., 6:46733-46743; Song et al. (2016) Acta Biomater., 39:146-155). Different from FK-16, free KR-12 is only active against Gram-negative bacteria such as E. coli, but not Gram-positive S. aureus USA300. Herein, orientation-specific immobilization of FK-16 (amino acid sequence FKRIVQRIKDFLRNLV (SEQ ID NO: 9)), the most potent LL-37 peptide, on a titanium surface is provided, which shows activity against a panel of the ESKAPE pathogens, including Enterococcus faecium, S. aureus, Klebsiella pneumoniae, Acinetobacter baumannii, P. aeruginosa and Enterobacter cloacae. The peptide coated surface also demonstrates anti-biofilm activity against methicillin-resistant S. aureus (MRSA) and E. coli. Significantly, the initial inoculum-dependent biofilm inhibition properties of the FK-16 peptide coated titanium surface are shown for an extended time period.

Materials and Methods
Peptides, Surface and Chemicals

Peptides were chemically synthesized and purified to >95% when used in the free form (Genemed Synthesis, San Antonio, Tex.). Peptides were solubilized in autoclaved distilled water and their concentrations were determined by UV spectroscopy (Waddell, W. J. (1956) J. Lab. Clin. Med., 48:311-314). Titanium foils (>99.6% pure) of 0.125 mm thickness were purchased from Goodfellow Corporation (Coraopolis, Pa.). All chemicals used in the immobilization were of analytical grade and purchased from Sigma (Saint Louis, Mo.) unless specified.

Bacteria and Growth Media

Bacterial strains used in this study included Enterococcus faecium ATCC51559, Staphylococcus aureus USA300 LAC, Klebsiella pneumoniae ATCC13883, Acinetobacter baumannii B2367-12, Pseudomonas aeruginosa PAO1, Enterobacter cloacae B2366-12 and Escherichia coli ATCC 25922, wherein the first six constituting the ESKAPE pathogens. Tryptic soy broth (TSB) for bacterial growth was obtained from BD Bioscience (Sparks, Md.).

Antimicrobial Assays

The antibacterial activity of peptides was evaluated using a standard broth microdilution protocol as described (Wang et al. (2012) Antimicrob. Agents Chemother., 56:845-856). In brief, 5 µl of each bacterium (stored at −80° C.) were inoculated into TSB medium (2 ml) and grown overnight. A second inoculation was made in the morning by delivering 10 µl of the overnight culture to a fresh TSB medium. After 2-3 hours growth at 37° C., 225 rpm, logarithmic phase bacterial cultures ($OD_{600} \approx 0.5$) were diluted and partitioned into a 96-well polystyrene microplate with $\sim 10^5$ colony forming units (CFU) per well (90 µl aliquots). After treatment with 10 µl of peptide solutions at various concentrations, microplates were incubated at 37° C. overnight and read on a ChroMate® 4300 Microplate Reader at 630 nm (GMI, Ramsey, Minn.). The medium was used as a blank where no bacteria should grow. The minimal inhibitory concentration (MIC) was defined as the lowest peptide concentration that completely inhibited bacterial growth.

Measurement of Peptide Hemolysis

Blood was obtained from the Blood Bank of the University of Nebraska Medical Center (UNMC) and washed three times (800 g, 10 minutes) with normal saline to remove plasma. A final solution containing 2% human red blood cells (hRBC) was then prepared in normal saline and used for the assay. 90 µl of this solution were added to 10 µl of serially diluted peptide solutions and incubated at 37° C. for 1 hour. It was then centrifuged at 15,700 g for 5 minutes on an Eppendorf® bench-top centrifuge 5415D. Aliquots of the supernatant (~80 µl) were carefully transferred to a fresh 96-well microplate (Costar, Corning, N.Y.) and absorbance was read at 545 nm to detect the amount of hemoglobin released. Percent lysis was calculated based on the extent of hemoglobin released, where 100% release is assumed in the presence of 1% TRITON™ X-100 and 0% release is assumed in saline.

Preparation of Peptides

In order to couple the peptide to a titanium surface, a cysteine residue was appended to either the N or C-terminus of FK-16. These peptides were characterized by mass spectrometry and HPLC with purity at least 90% (Genemed Synthesis).

Modification of the Titanium Surface

Prior to any chemical reactions, titanium (Ti) foils (1 cm×1 cm) were first cleaned ultrasonically with ethanol, distilled water and acetone, each for 15 minutes at 50 Hz. Initial surface activation was accomplished by alkaline etching with 5 M NaOH for 24 hours at 60° C. (Godoy-Gallardo et al. (2014) Acta Biomater., 10:3522-3534). Samples were then thoroughly cleaned by immersion in distilled water for 30 minutes twice, washed with acetone and dried. These hydroxylated surfaces were silanized with (3-aminopropyl)triethoxysilane (APTES, 0.5% vol.) in anhydrous toluene for 1 hour at 70° C. to obtain free amine groups. Excess and adsorbed reactants were removed by cleaning the foils ultrasonically with distilled water for 10 minutes. Surfaces were again profusely washed with ethanol, isopropanol, distilled water and acetone, and dried.

Orientation-Specific Immobilization of FK-16Cys to the Titanium Surface

The amino silanized Ti surfaces were reacted with a short bifunctional cross linker 6-maleimidoheaxanoic acid. The reaction of the free amines and cross linker (2 mg ml$^{-1}$) were carried out in 0.1 M 2-(N-morpholino)ethanesulfonic acid (MES) buffer at pH 4.7 in the presence of 1-ethyl-3-(3-dimethylaminopropyl) carbodiimide (EDC) (0.01% w v$^{-1}$) for 24 hours at room temperature. The amide reaction generated free maleimide groups that enabled the coupling with the C-terminal cysteine of FK-16Cys, leading to a similar orientation on the Ti-surface. The reaction was conducted overnight at room temperature in phosphate buffer (PBS) at a peptide concentration of 2.5 mg ml$^{-1}$. Finally, the surfaces were washed with ethanol, isopropanol, distilled water and acetone to remove any unbound peptide. The FK-16 peptide coated titanium surfaces (Ti-FK-16Cys) were dried and kept at −20° C. till other assays were performed. The detailed scheme of the reaction is illustrated in FIG. 9A.

Fourier-Transformed Infrared (FT-IR) Spectroscopy

The presence of signature bands in the IR spectrum confirmed the success of the stepwise coupling leading to the final product. The spectrum was recorded 20 scans from 600 cm$^{-1}$ to 4,000 cm$^{-1}$ with an IR Prestige-21 instrument (Shimadzu, Columbia, Md.) using Happ-Genzel apodization function.

X-Ray Photoelectron Spectroscopy (XPS)

Samples were analyzed using a Surface Science Instrument SSX-100 (Thermo Fisher Scientific, Waltham, Mass.) with an operating pressure of ~2×10$^{-9}$ torr. Monochromatic Al K-alpha X-rays (1,486.6 eV) were used with a beam diameter of 1 mm. Photoelectrons were collected at a 55° emission angle. A hemispherical analyzer determined electron kinetic energy, using a pass energy of 150 V for wide/survey scans, and 50 V for high resolution scans. A flood gun was used for charge neutralization of non-conductive samples. Elements were identified from the survey spectra. High resolution spectra of carbon, nitrogen, oxygen and sulfur were recorded individually for comparison of the element ratio.

Quantification of Surface Attached FK-16Cys Using Sulfosuccinimidyl-4-o-(4,4-Dimethoxytrityl) Butyrate (Sulfo-SDTB)

The amount of the covalently attached FK-16Cys on the Ti surface was measured using a spectrophotometric assay. This method utilizes the high extinction coefficient value of a complex ion formed by the reaction of the surface amino groups and Sulfo-SDTB. The immobilized peptide concentration was determined using an established protocol (Gaur et al. (1989) Anal. Biochem., 180:253-258). In brief, 1 ml of the Sulfo-SDTB (3.0 mg ml$^{-1}$) solution was prepared in dimethylformamide (DMF) and then diluted to 50.0 ml with a 50 mM sodium bicarbonate solution (pH 8.5). One ml of this solution was added to the peptide coated Ti samples followed by 1 hour incubation at room temperature. The samples were then washed twice with 5.0 ml of distilled water to remove any unused reactant, and immersed in 2.0 ml of perchloric acid for another 30 minutes. Absorbance of the solution was measured at 498 nm to detect the 4,4'-dimethyloxytrityp (DMTr) cation. The number of amine groups on the surface of each sample was quantified using the Beer-Lambert law with an extinction coefficient of 70,000 M$^{-1}$ cm$^{-1}$ and finally the amount of immobilized FK-16Cys was calculated based on the number of amines present in the peptide.

Microbiological Assays of Immobilized FK-16Cys

Antibacterial activity of the Ti-FK-16Cys surfaces was evaluated according to the published International Organization for Standardization (ISO) 22196 protocol with minor modifications (Kowalczuk et al. (2010) Int. J. Pharm., 402: 175-183). Briefly, a mid-exponential phase bacterial culture was washed with sterile PBS and adjusted to 10$^5$ CFU ml$^{-1}$. Twenty µl of the cell suspension were added on the top of each Ti surface placed in each well of a 24-well culture plate. Further, the plates were incubated at 37° C. for 2 hours. After incubation, 980 µl of fresh PBS were added and mixed to allow all the adhered cells to come into the PBS solution. Then, 100 µl of the solution were spread on LB agar plates for CFU determination after 18 hour incubation at 37° C. The Ti surface coated up to maleimide but without the peptide was used as a control.

In addition, the effects of serum and salt on the antimicrobial activity of the peptide immobilized surfaces were also analyzed. The samples, containing 10% of human serum (Human Serum, Pooled, MP Biomedicals, Santa Ana, Calif.) or 150 mM NaCl, were tested using *S. aureus* USA300. The samples were processed in the same manner as detailed above.

Inhibition of Bacterial Adhesion onto the FK-16Cys Coated Ti Surface

A quantitative estimation of bacterial adhesion inhibition by the FK-16Cys coated Ti surface was made using the 2,3-bis-(2-methoxy-4-nitro-5-sulfophenyl)-2H-tetrazolium-5-carboxanilide (XTT) assay (Mishra et al. (2016) ACS Med. Chem. Lett., 7:117-121). In short, *S. aureus* USA300 was grown in TSB overnight. One ml of the culture was then added to the wells of 24-well culture plates with surfaces coated with the linker and the FK-16 peptide, or the linker but no peptide. The plates were then incubated at 37° C. for 1 hour to allow for bacterial attachment. After removal of the medium, surfaces were washed three times with fresh PBS to remove unattached cells. Finally, fresh TSB medium containing 10% XTT solution with 1% PMS (N-methylphenazonium methyl sulfate) was further incubated for 2 hours at 37° C. Plates were read at 450 nm for calorimetric estimation of bacterial attachment. Comparison was made between the surfaces with and without the coated peptide to measure the anti-adhesion activity. The anti-adhesion activity was also assayed for *E. coli* in the same manner.

Inhibition of Biofilm Formation by FK-16Cys Coated Titanium

Inhibition of the biofilm formation by the Ti-FK-16Cys surface was also evaluated using *S. aureus* and *E. coli*. In short, bacteria at the exponential phase were adjusted to 10$^5$ or 10$^3$ CFU ml$^{-1}$ in fresh TSB medium. One ml of the culture was then added to the wells of 24-well culture plate containing the surface that was coated up to maleimide or peptide. The plates were then incubated at 37° C. for 24 hours to allow for biofilm formation. Media were then removed and surfaces were washed with fresh PBS three times. Quantification of live bacteria in the biofilm was performed using the XTT assay as described above, except for the use of 20% XTT.

Cytotoxicity Assays of Ti-FK-16Cys to Human Keratinocytes

In vitro spontaneously transformed keratinocytes from histologically normal human skin (HaCaT cells) from Fisher (Hampton, N.H.) (Cat # T0020001) were maintained in DMEM high glucose medium with 4 mM L-glutamine (HyClone, South Logan, Utah) and 100 U ml$^{-1}$ penicillin, 100 µg ml$^{-1}$ streptomycin (pen/strep, p/s) (Life Technologies, Carlsbad, Calif.), and 10% (v v$^{-1}$) inactivated fetal bovine serum (FBS, NyClone), DMEM with 10% FBS, p/s. Cells were grown in 5% CO$_2$ at 37° C. and were detached from culturing dish at 100% confluency by treating with 0.025% trypsin-EDTA (NyClone), seeded (100,000 cells well$^{-1}$) in 24-well plates (Corning Life Science, Salt Lake City, Utah) and grown overnight in 200 µl of DMEM medium to reach a 70% confluency. The peptide-coated surfaces (1.0×1.0 cm) were placed in a 24-well plate DMEM with or without 10% FBS, p/s for 1 hour. Samples were taken out and 60 µl of CellTiter96® MTS were added. Plates were further incubated for another 2 hours at 37° C. Subsequently, 100 µl of the solution were placed in a clean 96-well plate to measure the absorbance at 492 nm on a ChroMate® reader (GMI). For comparison, the toxicity of the soluble peptides was also measured and they were treated in the same way as described above. The culture medium and a 0.2% SDS solution were used as negative and positive controls, respectively.

Interestingly, the FK-16Cys peptide showed broader activity (Table 7). It is active against most of the strains in the range of 12.5-50 µM. Therefore, the addition of a cysteine at the C-terminus of FK-16 retained more peptide activity. It is likely that the cationic N-terminus of FK-16, including K18 and R19 (as numbered in LL-37), can rapidly recognize anionic pathogens via electrostatic interactions followed by the anchoring into bacterial membranes through the hydrophobic surface containing the aromatic ring of F17 (Wang, G. (2008) J. Biol. Chem., 283:32637-32643; Wang et al. (2012) Antimicrob. Agents Chemother., 56:845-856). Thus, FK-16Cys was chosen as a candidate for surface immobilization.

TABLE 7

Antibacterial activities of FK-16 and cysteine-attached variants against the ESKAPE pathogens. EF: *E. faecium* ATCC51559; SA: *S. aureus* USA300 LAC; KP: *K. pneumonia* ATCC 13883; AB: *A. baumannii* B2367-12; PA: *P. aeruginosa* PAO1; ECl: *E. cloacae* B2366-12 and EC: *E. coli* ATCC 25922.

| | MIC (µM) | | | | | | |
|---|---|---|---|---|---|---|---|
| Peptide | EF | SA | KP | AB | PA | ECl | EC |
| FK-16 | 3.1 ± 0 | 4.67 ± 1.8 | 4.67 ± 1.5 | 4.67 ± 2.2 | 50 ± 0 | 12.5 ± 0 | 4.67 ± 2.2 |
| CysFK-16 | 6.25 ± 0 | 18 ± 7.2 | ≥50 | 25 ± 0 | >50 | >50 | >50 |
| FK-16Cys | 12.5 ± 0 | 18 ± 7.2 | 12.5 ± 0 | 12.5 ± 0 | >50 | 50 ± 0 | 37.5 ± 17.6 |
| Merecidin | ≤3.1 | 3.1 ± 0 | ≤3.1 | 3.1 ± 0 | 6.25 ± 0 | 6.25 ± 0 | 3.1 ± 0 |

Hemolysis of the FK-16Cys Coated Ti Surface

Blood cells were prepared as described above for soluble peptides; 450 µl of this solution were then added to the peptide coated surfaces (1.0×1.0 cm) placed in a 24-well plate. The remaining 50 µl contained PBS, TRITON™-X100, or soluble peptides. The plate was incubated for 1 hour at 37° C. Then 100 µl of the cell suspension were centrifuged at 15,700 g for 5 minutes on an Eppendorf® bench-top centrifuge 5415D. Supernatants were transferred to a clean 96-well plate (Costar, Corning, N.Y.) and absorbance was read at 545 nm to detect the amount of hemoglobin released. For a positive control 1% TRITON™ X-100 was used (100% lysis), while PBS served as a negative control (0% lysis).

Results

Impact of a Terminal Cysteine Appendage on the Antimicrobial and Cytotoxic Activity of Free FK-16

To preserve peptide orientation on the surface, a specific maleimide-thiol based coupling method was selected. In this method, cysteine from the peptide reacts with maleimide from the linker (Hermanson, G. T. (2013) Chapter 8—Dendrimers and dendrons. In: Bioconjugate techniques (3rd ed.) Hermanson, G. T., ed. Boston (Mass.): Academic Press; p. 351-386). This requires the addition of a cysteine amino acid to FK-16. The FK-16 variant with a cysteine added to the N-terminus is named CysFK-16, while the variant with a cysteine at the C-terminus is referred to as FK-16Cys. The impact of the addition of the cysteine on peptide activity was evaluated. Antimicrobial activities of FK-16 and its two variants are summarized in Table 7. Similar to the engineered peptide merecidin (Wang et al. (2014) ACS Chem. Biol., 9:1997-2002), FK-16 was found to be active against almost all the tested ESKAPE pathogens with a minimal inhibitory concentration (MIC) in the range of 3.1-12.5 µM, although it was less active against *P. aeruginosa* PAO1 (MIC=50 µM). CysFK-16 lost activity against *K. pneumonia*, *P. aeruginosa*, *E. cloacae* and *E. coli* (MIC>50 µM); it only retained activity against *E. faecium* at 6.25 µM, *S. aureus* at 18 µM, and *A. baumannii* at 25 µM, respectively.

The cytotoxicity of FK-16Cys before immobilization was also evaluated. Free FK-16Cys showed a 50% lethal concentration ($LC_{50}$) to HaCaT cells over 100 µM and 50% hemolytic concentration ($HL_{50}$) of ~35 µM. A $HL_{50}$ of ~100 µM for GF-17, which contains one additional glycine at the N-terminus compared to FK-16, was also determined (Mishra et al. (2016) ACS Med. Chem. Lett., 7:117-121). Therefore, the addition of a cysteine at the C-terminus of FK-16 made the peptide more hemolytic. However, this toxicity could be masked after surface coating of this peptide (see below).

Orientation-Specific Immobilization of FK-16Cys

Next, hydroxyls were generated on the titanium surface by alkaline treatment (5 M NaOH) overnight at 50° C. The resultant hydroxyl groups were covalently silanized with (3-aminopropyl)triethoxysilane (APTES) to generate surface amines. Subsequently, a bifunctional short spacer, 6-maleimidohexanoic acid, was coupled to the APTES amine via a 1-ethyl-3-(3-dimethylaminopropyl) carbodiimide (EDC) coupling reaction, leading to a free maleimide. The free maleimide group can react very specifically with thiol (peptide-cysteine) in the pH range of 6.5-7.5 to form a stable thioether linkage (Hermanson, G. T. (2013) Chapter 8—Dendrimers and dendrons. In: Bioconjugate techniques (3rd ed.) Hermanson, G. T., ed. Boston (Mass.): Academic Press; p. 351-386). The scheme of the series of reactions for peptide coating is depicted in FIG. 9A.

Surface Characterization of Ti-FK-16Cys Surfaces

The stepwise proceeding of the reaction was monitored using FT-IR spectroscopy (FIG. 9B). The signature stretching vibration band of amide I at 1,650 cm$^{-1}$ and amide II at 1,560 cm$^{-1}$ confirmed the immobilization of the peptide onto the Ti surface. Although the same bands also appeared on the Ti-Mal coated surface because of the amide reaction between the surface amine and carboxyl group of the spacer, sharp increases in their intensities yielded clear evidence for peptide grafting. XPS was used to verify the peptide immobilization. The wide range spectra for carbon 1s, nitrogen 1s, and oxygen 1s at corresponding binding energy confirmed the presence of respective elements as anticipated during the proceeding of the reaction. However, the signal of the sulfur 2p peak at 164 eV provided strong evidence for successful immobilization of FK-16Cys because it only existed in the peptide (FIG. 9C). In addition, the increments of the nitrogen and carbon elemental composition, and the decrease in the oxygen content from 48.04 to 17.53% of samples coated with maleimide and peptide, also support immobilization.

Immobilized Peptide Quantification

Having established the chemical platform, the amount of FK-16Cys on the surface was quantitated using a spectroscopic method (Gaur et al. (1989) Anal. Biochem., 180:253-258). The free amines of the peptide were titrated with sulfo-SDTB. The resultant product by acid lysis led to the chromophore, 4,4'-dimethoxytrityl cation (DMTr), which has a high extinction coefficient of 70,000 $M^{-1}$ $cm^{-1}$ at 498 nm. Beer's Lambert law was employed to calculate the amount of cation released, which was correlated with the amount of free amines of the immobilized peptide, which include two lysines and the N-terminus (Gabriel et al. (2006) Bioconjug. Chem., 17:548-550). Based on this, a surface peptide density at $6 \times 10^{-10}$ mol $cm^{-2}$ was determined. This FK-16Cys coated peptide density is four times the amount of LL-37 ($1.47 \times 10^{-10}$ mol $cm^{-2}$) coated to the same titanium surface (Gabriel et al. (2006) Bioconjug. Chem., 17:548-550).

Antibacterial Activity of Immobilized FK-16Cys Against the ESKAPE Pathogens

The antimicrobial activity of the FK16-immobilized surface was evaluated against the ESKAPE pathogens which account for >90% of the nosocomial infections. Using the ISO 22196 protocol, a method for evaluation of the antibacterial activity on non-porous surfaces (Kowalczuk et al. (2010) Int. J. Pharm., 402:175-183), the surface was found to be very active (FIG. 10). It reduced the growth of E. faecium by ~1 log (~80% in FIG. 10A) and S. aureus by ~1.5 log (over ~95% in FIG. 10B). Further, it completely inhibited the growth of K. pneumonia and E. coli (FIGS. 10C and 10F), although it only reduced the CFU of A. baumannii by 0.5 log (FIG. 10D). A 2 log CFU reduction was observed for P. aeruginosa (~98% inhibition in FIG. 10E). Only E. cloacae was not significantly inhibited by the FK16-coated surface. Thus, the new surface immobilized with FK-16 possessed broad antimicrobial activity against planktonic bacterial cells, which is in concordance with the activity of free FK-16 (Table 7). In addition, the activity of the peptide coated surfaces in the presence of 10% human serum (FIG. 11A) and 150 mM NaCl (FIG. 11B) was also determined against S. aureus USA300. The FK-16 immobilized surface was not significantly effective in the presence of serum, but remained active in the presence of the salt.

Anti-Biofilm Activity of FK-16Cys Coated Ti Surface

Since it is difficult to remove biofilms from implanted medical devices, the anti-biofilm property of the FK-16Cys coated titanium surface was also tested using both Gram-positive S. aureus USA300 and Gram-negative E. coli ATCC 25922. Bacterial surface attachment is regarded as the first stage of biofilm formation. To test this peptide property, the anti-attachment potential of this surface was investigated against a high density overnight bacterial culture (~$5.0 \times 10^9$ CFU $ml^{-1}$ for both bacteria). It reduced the attachment of S. aureus by ~30% (FIG. 12A). However, the new surface was even more active in the case of E. coli; a ~85% reduction was observed (FIG. 12B). Following bacterial attachment to the substratum, biofilms could further develop into a complicated structure covered with extra cellular materials such as carbohydrates, eDNA, and proteins.

The biofilm inhibition capability of these peptide coated surfaces was tested. At an initial bacterial inoculum of $10^5$ CFU, they reduced the biofilms of S. aureus and E. coli by ~75% and ~80%, respectively (FIG. 13). The length of time the FK-16Cys coated surface could retain anti-biofilm property was also determined. The surface failed to show significant biofilm inhibitory activity at $10^5$ CFU when the biofilm forming time was extended to 48 or 72 hours (FIG. 13). However, this FK-16 coated titanium surface remained effective at 48 or 72 hours when a reduced initial inoculum of $10^3$ CFU was used (FIG. 13).

Biocompatibility of Ti-FK-16Cys Against Human Keratinocytes and Red Blood Cells

An important prerequisite of implanted medical devices is biocompatibility. The cytotoxicity of the FK-16Cys coated titanium surface was tested using human epidermal keratinocytes (HaCaT cells) and human erythrocytes hRBCs. While no significant reduction in HaCaT cell growth was observed with or without FBS (FIG. 14A), the surface was devoid of hemoglobin release after incubation with hRBCs (FIG. 14B). These results indicate that the cell toxicity of the FK-16Cys immobilized surface was little to none.

Biofilms usually consist of complex bacterial communities covered with biopolymers such as polysaccharides and eDNA. Such a structure is resistant to host defenses or antibiotic treatments. Therefore, a preferred strategy would be to prevent the formation of biofilms on implanted medical devices. Although traditional antibiotics have been coated to surfaces, they may not provide sufficient protection as a consequence of the growing antibiotic resistance problem. Antimicrobial peptides are regarded as useful candidates for surface coatings (Costa et al. (2011) Acta Biomater., 7:1431-1440; Onaizi et al. (2011) Biotechnol. Adv., 29:67-74). Several laboratories have tested surface coating of human cathelicidin LL-37. The PEG linker between the peptide and surface, as well as orientational coupling via the maleimide chemistry, was found to be essential for E. coli killing by the peptide-immobilized titanium surface (Gabriel et al. (2006) Bioconjug. Chem., 17:548-550). Likewise, it was found that both peptide structure and activity could be influenced by the length of the linker as well as the orientation of the peptide coated to the surface (Han et al. (2014) J. Phys. Chem. B, 118:2904-2912). Furthermore, the LL-37 molecule, after being immobilized onto the poly-hydroxyethyl methacrylate (pHEMA) surface, is active against P. aeruginosa, but not S. aureus (Dutta et al. (2016) Biofouling 32:429-438). However, LL-37 (37 amino acids) is relatively long and costly to manufacture. Consequently, there is a great desire to use its active fragments. IG-25 is a C-terminal fragment of LL-37 corresponding to residues 13-37, which possesses both antibacterial and anticancer activities (Li et al. (2006) J. Am. Chem. Soc., 128:5776-5785). This 25mer peptide, when attached to a fluorous surface via the specific click chemistry (Santos et al., (2013) ACS Appl. Mater. Interfaces 5:12789-12793), kills P. aeruginosa by permeating bacterial membranes. Further, the lens modified with IG-25 reduces the colonization of P. aeruginosa PAO1 by 98%. Some non-peptide agents also have this property. For instance, it was found that lactam can inhibit Streptococcus mutans growth on titanium (Xavier et al. (2016) Mater. Sci. Eng. C Mater. Biol. Appl., 68:837-841). In addition, KR-12, the smallest antibacterial peptide (residues 18-29) of human LL-37, retains activity against E. coli K12, but not S. aureus USA300 (Wang, G. (2008) J. Biol. Chem., 283:32637-32643; Epand et al. (2009) Antimicrob. Agents Chemother., 53:3705-3714). KR-12 was connected to the surface via a reaction between amine of the silanization agent and the carboxylic acid of the peptide for 8 hours at room temperature. The KR-12 coated surface reduces the adherence of *Staphylococcus epidermidis* (Nie et al. (2016) RSC Adv., 6:46733-46743). It is evident that only one to two bacterial strains were tested for each of the above LL-37 peptide coated surfaces. Therefore, this study represents the first case where surfaces immobilized with FK-16 show efficacy against a wide range of bacteria, including nearly all the ESKAPE pathogens (FIG. 10). Note that the presence of serum reduces the surface effectiveness, probably due to the serum binding property of the LL-37 cathelicidin peptides (Dun et al. (2006) Biochim. Biophys. Acta., 1758:1408-1425). However, 150 mM NaCl did not reduce the antimicrobial activity of the surface (FIG. 11B) against *S. aureus* USA300. While both the IG-25 and KR-12 surfaces were subjected to anti-adhesion tests, no biofilm inhibition was tested using the LL-37 peptide coated surfaces prior to the current study. Therefore, biofilm inhibition ability of the FK-16 coated titanium surface has been shown (FIGS. 12 and 13).

Significantly, the utility of this new surface in inhibiting biofilm formation for an extended time period of 48 hours and 72 hours is also shown, particularly when an initial $10^3$ CFU of bacteria are inoculated. Note that it is common practice to minimize the potential pathogen contamination when medical devices are implanted via surgery. Such a practice may lead to lower initial bacterial CFUs, if there are any. Therefore, the use of a low CFU concentration of $10^3$ in these assays better mimics starting conditions after surgery. Under such a 'clean' condition, it was anticipated the coated surfaces would be effective. In other words, a high starting CFU such as $10^5$ or more is not realistic unless there is already infection, which needs pre-treatment before inserting any medical device. Interestingly, the same $10^3$ inoculum is reported to be critical to evaluate the immune response to various *S. aureus* strains in a mouse orthopedic-implant biofilm infection model since all the differences disappeared at a higher CFU (Vidlak et al. (2016) Infect. Immun., 84:1957-1965). Thus, the use of $10^3$ CFU is medically relevant.

There are reports that commensal bacteria can prevent colonization of invading pathogens (Hwang et al. (2016) Drug Resist Update 27:59-71). While maintaining an elegant balance of commensal microbiota can be a helpful strategy to fight antibiotic resistance, it may not be a general practice for implanted medical devices. Depending on the location of the device in human bodies, however, the colonization of commensal bacteria may not be desired, especially those opportunistic pathogens. The broad antimicrobial activity of the FK-16 coated surface may not allow the colonization of such bacteria. On the other hand, rapid attachment of human cells to implanted devices could be desired so that the device becomes an integral part of the body. Notably, the KR-12 coated titanium surface can improve the attachment and proliferation of human bone marrow mesenchymal stem cells (Nie et al. (2016) RSC Adv., 6:46733-46743). It is also important that the coated surfaces have negligible cytotoxicity to the surrounding tissues. Under the conditions tested, the FK-16 coated surface showed no hemolysis and little toxicity to human skin cells. Therefore, these results underscore the biocompatibility of the FK-16 coated anti-biofilm surfaces.

It is clear that the FK-16 coated titanium surface retained the antimicrobial and anti-biofilm effects of the major antimicrobial region of LL-37. It also retained the serum binding property known to the parent peptide LL-37 (Durr et al. (2006) Biochim. Biophys. Acta., 1758:1408-1425). These results indicate that the chemistry used here is proper. The current FK-16 coated surface may be used for serum-free cases (e.g., medical tools and surfaces for operation). It can also be applied to situations where serum is limited and, when generated, is only limited to the initial stage. Under such circumstances, the areas may be rinsed with saline to remove serum to mitigate any interference. Recently, it has been demonstrated that injection of merecidin, a peptide designed also based on the major antimicrobial region of human LL-37, can prevent staphylococcal biofilm formation in an animal catheter model and boost immune responses (Wang et al. (2014) ACS Chem. Biol., 9:1997-2002). Taken together, the major antimicrobial region of human cathelicidin LL-37 can be developed into different medical treatment options to control bacterial biofilms involving the ESKAPE pathogens.

In summary, a titanium-based antimicrobial and antibiofilm platform was developed where FK-16, a peptide corresponding to the major antimicrobial region of the human cathelicidin LL-37, is directionally coupled to the surface via a short six-carbon linker. Except for *E. cloacae*, the FK-16 coated titanium surfaces were able to inhibit not only superbugs such as the ESKAPE pathogens but also bacterial surface adhesion of both *S. aureus* USA300 and *E. coli* ATCC 25922. Importantly, it was also demonstrated that inhibition of biofilm formation by the FK-16 immobilized surface occurred for an extended time frame, from 24 to 72 hours. Also, these antimicrobial effects could be achieved at a concentration not toxic to human cells. Thus, the titanium surfaces covalently immobilized with the major antimicrobial peptide of human LL-37 can be used to prevent biofilm-related infection on implanted medical devices.

Example 3

Naturally occurring antimicrobial peptides (AMPs) are endogenous defense molecules of living organisms (Zasloff, M. (2002) Nature 415:389-395; Hancock et al. (2006) Nat. Biotechnol., 24:1551-1557; Epand et al. (1999) Biochim. Biophys. Acta 1462:11-28). They remain potent for millions of years, making them appealing templates for developing the next generation of antimicrobials to combat superbugs and difficult-to-kill viruses. The amino acid use in such peptides is biased so that they have the desired sequence feature to recognize invading pathogens. In α-helical amphibian AMPs, glycine, leucine, alanine, and lysine are rich, whereas glycine, arginine, and cysteine are abundant in β-sheet peptides. Such abundant amino acids can determine the peptide scaffold (Wang et al. (2016) Nucleic Acids Res., 42:D1087-D1093; Wang, G. (2010) Antimicrobial Peptides: Discovery, Design and Novel Therapeutic Strategies, Cambridge, CABI). In contrast, certain amino acids, such as histidine (His) and tryptophan (Trp), are less frequently deployed on average in natural AMPs (aps.unmc.edu/AP). However, Trp and His can be abundant in some peptides. Interest in Trp-rich peptides remains high because they are relatively short yet potent against superbugs. Usually, these Trp-rich peptides are also accompanied by arginine (Arg) (Chan et al. (2006) Biochim. Biophys. Acta 1758:1184-1202; Rozek et al. (2000) Biochemistry 39:15765-15774; Schibli et al. (1999) Biochemistry 38:16749-16755). The combination of hydrophobic Trp and cationic Arg are sufficient to generate amphipathic sequences. Such amphipathic sequences lay the foundation for AMPs to target bacterial membranes. While cationic residues can recognize anionic surfaces, hydrophobic Trp amino acids can anchor the entire peptide to the membrane. Structural determination of membrane-bound AMPs enables one to view the active conformation and provides a basis for structure-based peptide design. Most of the structures of small AMPs are determined by the classic two-dimensional (2D) nuclear magnetic resonance (NMR) method, which typically requires the recording of TOCSY, DQF-COSY, and NOESY spectra. Due to the complex nature of biological membranes, most of the structural characterization of Trp-containing AMPs was conducted in membrane-mimetic environments such as micelles. The structures of indolicidin and tritrpticin are extended with multiple turns (Chan et al. (2006) Biochim. Biophys. Acta 1758:1184-1202; Rozek et al. (2000) Biochemistry 39:15765-15774; Schibli et al. (1999) Biochemistry 38:16749-16755). How the multiple aromatic rings bind to membranes is not always obvious because they are not all located on the same hydrophobic surface. The story is further complicated since those Trp-rich peptides can also interact with bacterial DNA (Fojan et al. (2017) Methods Mol. Biol., 1548:201-215).

Materials and Methods

Peptide Quantification

Chemically synthesized peptides ordered from a commercial source (Genemed, TX). They were highly purified by HPLC as indicated by the major peak (purity >95%) on the chromatograms detected at 220 nm. Since these peptides are rich in Trp, they were solubilized in water and quantified by UV at 280 nm based on the established molar extinction coefficient 5550 $M^{-1}$ $cm^{-1}$.

HPLC Elution Time

Peptides were solubilized in water and subjected to a high-speed spin at 14,000 rpm before injection into the HPLC. The retention time of the peptide was measured on a WATERS HPLC system fitted with a reverse phase Symmetry® C18 waters column (4.6×150 mm) in the analytical mode. The peptide was eluted with a gradient of acetonitrile (containing 0.1% trifluoroacetic acid; TFA) from 5-95% at flow rate of 1 mL/minute. Peptide was detected by UV at 280 nm.

NMR Spectroscopy

For NMR measurements, the peptide concentration was 4 mM in 0.3 ml of aqueous solution of 90% $H_2O$ and 10% $D_2O$ at pH 6.2. The peptide/dodecylphosphocholine molar ratio was 1:57. The pH of each sample was adjusted by using microliter aliquots of HCl or NaOH solution and measured directly in the 5-mm NMR tube with a micro-pH electrode (Wilmad-Labglass). All proton NMR data were collected at 25° C. on a Varian INOVA 600 MHz NMR spectrometer equipped with a triple-resonance cryoprobe. A set of NMR spectra was collected for the TetraF2W-RK peptide using States-TPPI (Marion et al. (1989) J. Magn. Reson., 85:393-399). NOESY spectra (Jeener et al. (1979) J. Chem. Phys., 71:4546-4553) were acquired at a mixing time of 100 ms. TOCSY experiments were performed with a mixing time of 80 ms using a clean MLEV-17 pulse sequence (Braunschweiler et al. (1983) J. Magn. Reson., 53:521-528). Typically, two-dimensional homonuclear spectra were collected with 400 increments (16 scans each) in t1 and 2,048 data points in t2 time domains using a spectral width of 10,000 Hz in both dimensions with the $^1H$ carrier on the water resonance. The water signal was suppressed by low power presaturation during both the relaxation delay and the mixing period in NOESY experiments and during relaxation delay only for TOCSY (Bax et al. (1985) J. Magn. Reson., 65:355-360) and DQF-COSY (Rance et al. (1983) Biochem. Biophys. Res. Commun., 117:479-485) experiments. To obtain backbone $^{15}N$, $^{13}C\alpha$, and $^{13}C\beta$ chemical shifts, gradient enhanced HSQC spectra (Kay et al. (1992) J. Am. Chem. Soc., 114:10663-10665), between $^1H$ and $^{15}N$ as well as between $^1H$ and $^{13}C$, were collected at the natural abundance. The $^1H$, $^{15}N$, and $^{13}C$ carriers were set at 4.77, 118.27, and 36.37 ppm, respectively. Typically, 60 increments (128 scans) and 120 increments (64 scans) were collected for the $^{15}N$ (spectral width 2,000 Hz) and aliphatic $^{13}C$ (spectral width 21118.4 Hz) dimensions, respectively. All NMR data were processed on an Octane work station using the NMRPipe software (Delaglio et al. (1995) J. Biomol. NMR 6:277-293). The data points in the indirect dimension were doubled by liner prediction (Zhu et al. (1990) J. Magn. Reson., 90:405-410). NMR data were apodized by a 63° shifted squared sine-bell window function in both dimensions, zero-filled prior to Fourier transformation to yield a data matrix of 2,048×1,024. Because anionic DSS interacts with cationic peptides (Wang et al. (2003) Protein Sci., 12:1087-1096), it was not used as an internal chemical shift standard to prevent the detergent additive effect. Instead, the proton chemical shifts of the peptide were referenced to the water signal, which in turn was referenced to internal DSS at 0.00 ppm (Hartel et al. (1982) Eur. J. Biochem., 129:343-357). $^{15}N$ and $^{13}C$ chemical shifts were referenced based on the ratios recommended by IUPAC (Markley et al. (1998) J. Biomol. NMR 12:1-23). NMR data were analyzed with the program PIPP (Garrett et al. (1991) J. Magn. Reson., 95:214-220). The peptide proton signals were assigned using the standard procedure (Wüthrich, K. (1986) NMR of Proteins and Nucleic Acids, Wiley, New York) based on two-dimensional TOCSY, DQF-COSY, and NOESY spectra. $^{15}N$, $^{13}C\alpha$, and $^{13}C\beta$ chemical shifts of the peptides were assigned on the basis of the known proton chemical shifts.

Structural Calculations

Three-dimensional structures of the peptides in complex with DPC-d38 at pH 6.2 and 25° C. were calculated based on both distance and angle restraints by using the simulated annealing protocol (Nilges et al. (1988) Protein Eng., 2:27-38) in the National Institutes of Health version of X-PLOR (Brünger, A. T. (1992) X-PLOR: A system for X-ray Crystallography and NMR, Yale University Press, New Haven; Schwieters et al. (2002) J. Magn. Reson., 160:65-73). The distance restraints were obtained by classifying the NOE cross peak volumes into strong (1.8-2.8 Å), medium (1.8-3.8 Å), weak (1.8-5.0 Å), and very weak (1.8-6.0 Å) ranges (Clore et al. (1989) CRC Crit. Rev. Biochem. Mol. Biol., 24:479-654). The distance was calibrated on the basis of the typical NOE patterns in an α-helix (Wüthrich, K. (1986) NMR of Proteins and Nucleic Acids, Wiley, New York). Peptide backbone restraints were obtained from the TALOS (Cornilescu et al. (1999) J. Biomol. NMR 13:289-302) analysis of a set of heteronuclear chemical shifts, including $^1H\alpha$, $^{13}C\alpha$, $^{13}C\beta$, and $^{15}N$ A covalent peptide structure with random angles but trans-planar peptide bonds was used as a starting structure. All peptide structural templates were also amidated at the C terminus using X-PLOR (Brünger, A. T. (1992) X-PLOR: A system for X-ray Crystallography and NMR, Yale University Press, New Haven). In total, 100 structures were calculated. An ensemble of 20 structures with the lowest total energy was chosen for structural analysis. This final ensemble of accepted structures satisfies the following criteria: no NOE violations greater than 0.30 Å, r.m.s.d. for bond deviations from the ideal less than 0.01 Å, and r.m.s.d. for angle deviations from the ideal less than 5°.

Antibacterial Activity Assays

The antimicrobial activity of peptides was evaluated using a standard broth microdilution protocol. In brief, exponential phase bacteria at $10^6$ CFU were incubated with serially diluted peptides overnight for ~20 hours at 37° C. The plates were read on a ChroMate® 4300 Microplate Reader at 630 nm (GMI, Ramsey, Minn.). The minimal inhibitory concentration (MIC) was defined as the lowest peptide concentration that fully inhibited bacterial growth.

Hemolytic Ability

Hemolytic analysis of selected peptides was performed using an established protocol. Briefly, human blood cells (UNMC Blood Bank) were washed three times with phosphate buffer saline (PBS) and diluted to a 2% solution. After peptide treatment, incubation at 37° C. for one hour, and centrifugation at 13,000 rpm, aliquots of the supernatant were transferred to a fresh 96-well microplate. To assess peptide cytotoxicity, the amount of hemoglobin released was measured at 545 nm. The percent lysis was calculated by assuming 100% release when human blood cells were treated with 1% TRITON™ X-100, and 0% release when incubated with PBS buffer.

Membrane Permeation of Peptides

Fluorescence spectroscopy was also used to follow bacterial killing. In brief, 10 µL of serially diluted 10× peptide concentrations were done in 96-well corning COSTAR microtiter plates. Propidium iodide at a fixed concentration of 20 µM per well was added to each well which was finally incubated with 88 µL of S. aureus USA300 (with a final $OD_{600}$~0.1) with continuous shaking at 100 rpm with meander corner well shaking, 37° C. in a FLUOstar® Omega (BMG LABTECH Inc., NC) microplate reader. The plates were read every 5 minutes for a total duration of 2 hours with excitation and emission wavelengths at 584 nm and 620 nm, respectively.

Live Cell Penetration Experiment

The entrance of a fluorescent dye into live bacterial cells was followed by confocal microscopy (Mishra et al. (2015) RSC Advances 5:59758-59769). In short, S. aureus USA300 was grown to the exponential phase from the overnight culture. The cells were then washed twice with fresh 1×PBS (pH 7.2) and the final cell density was adjusted to $1\times10^8$ CFU/mL. 1500 µL of the culture was added to the chambers of cuvettes (borosilicate cover glass systems) with equimolar concentrations of TetraF2W-RK and fluorescein isothiocyanate FITC (12.5 µM). The samples were examined with a confocal laser scanning microscope (Zeiss 710) with a series of live time pictures taken at every 5 seconds for 5 minutes and the data were processed using Zen 2010 software.

Antibiofilm Assays

Two types of experiments were conducted to evaluate the anti-biofilm activity of these peptides against S. aureus USA300 grown under a static condition for 24 hours to form established biofilms in presence of tryptic soy broth (TSB). The experiment was set up using a flat bottom, 96-well, polystyrene microtiter plates (Corning, COSTAR). In short, S. aureus USA300 ($10^5$ CFU/mL) in fresh TSB media was made from an exponentially growing culture. 200 µL of this bacterial culture was added to each well of the microtiter plates. The plates are then incubated at 37° C. for 24 hours to allow biofilm formation. Media was then carefully removed followed by washing with sterile 1×PBS to remove any unattached bacteria. Solution containing 20 µL of 10× peptide solution and 180 µL of fresh TSB were added. The plates were again incubated at 37° C. for another 24 hours. To measure the extent of biofilm disruption by the peptides as a function of biofilm reduction, crystal violet staining was performed. Media was pipetted out and the wells were carefully washed with 200 µL of PBS to remove the loosely attached cells. Subsequently, 200 µL of 99% methanol was added for fixation and the plates were allowed to sit for 15 minutes. The plates were finally aspirated and dried. Lastly, staining was done with 200 µL of 1% crystal violet in water for 5 minutes. Excess stain was gently rinsed off with tap water, and plates were air-dried. Further, stains were solubilized in 200 µL of 33% glacial acetic acid followed by colorimetric measurement at 600 nm on a Chromate® microtiter plate reader. The amounts of biofilm growth with and without compound treatments were calculated.

In addition, live cell contents of the peptide acted biofilms was estimated by XTT [2,3-bis(2-methyloxy-4-nitro-5-sulfophenyl)-2H-tetrazolium-5-carboxanilide]assay by following the manufacturer's instructions with modifications. A 10% XTT solution in TSB media was added to each well and the plates were again incubated for 2 hours at 37° C. Absorbance at 450 nm (only media with XTT containing wells served as the blank) was obtained using Chromate® microtiter plate reader. Percentage of biofilm reduction for the peptide was plotted assuming 100% biofilm growth is achieved on the bacterial wells without peptide treatment.

Confocal Microscopy of Biofilms in the Absence and Presence of Peptides

S. aureus USA300 ($10^5$ CFU/mL) was made from exponentially growing bacteria. 1800 µL was added to the chamber of cuvettes (Borosilicate cover glass systems), and was incubated for 37° C., 24 hours for biofilm formation. Media was then pipetted out and chambers were washed with 1×PBS to remove non-adhered cells. To disrupt the preformed biofilms, 200 µL of 10× stocks of the peptide was added followed by 1800 µL of TSB. Control cuvettes contained water instead of peptide. The cuvettes were again incubated for another 24 hours at 37° C. Subsequently, the supernatant was pipetted out and the chambers were washed with 1×PBS. For evaluation under confocal microscope the biofilms were stained with 10 µL of LIVE/DEAD® kit (Invitrogen Molecular Probes) according to the manufacturer's instructions. The samples were examined with a confocal laser scanning microscope (Zeiss 710) and the data processed using Zen 2010 software.

Results

A unique structure is provided herein for a newly designed Trp-rich peptide TetraF2W-RK (WWWLRKIW-amide; SEQ ID NO: 3), which contains 50% Trp, one of the highest percentages known to date. This peptide appears to act on bacterial membranes. First, Staphylococcus aureus USA300 can be rapidly killed. Second, the peptides synthesized using L- or D-amino acids give an identical minimal inhibitory concentration (MIC) against S. aureus, indicating a chiral protein-like interface is not involved. Third, after peptide treatment, a non-permeable dye fluorescein isothiocyanate (FITC) can enter S. aureus in 30 seconds, indicating membrane damage by the peptide. These results laid a solid basis to determine the 3D structure of TetraF2W-RK bound to membrane-mimetic micelles. The improved 2D NMR method (Wang et al. (2005) J. Biol. Chem. 280:5803-5811) was utilized for structural determination because recent studies show the importance of this method for peptides rich in certain amino acids (e.g., leucine and cysteine) (Conibear et al. (2012) Biochemistry 51:9718-9726; Wang, G. (2013) Pharmaceuticals 6:728-758). In this method, five 2D NMR spectra are recorded ($^1H$-$^1H$ TOCSY, DQF-COSY, NOESY, $^1H$-$^{13}C$ HSQC, and $^1H$-$^{15}N$ HSQC). The $^{15}N$ and $^{13}C$ resonances have a broader range of chemical shifts, enabling the validation of proton assignments. In addition, these heteronuclear chemical shifts also contain structural information and can be used to refine the nuclear Overhauser effect (NOE)-derived structure to achieve high quality (Wang, G. (2013) Pharmaceuticals 6:728-758). Different from indolicidin and tritrpticin, this membrane-targeting Trp-rich peptide, TetraF2W-RK, forms a regular two-turn α-helix with a clear amphipathic nature, enabling one to decipher the role of each residue via single residue substitutions. The results reveal that the π configuration of the N-terminal Trp triplet (WWW) of this short cationic peptide plays a critical role in disrupting the preformed biofilms of *S. aureus* USA300 based on quantification of both biomass and live bacteria.

The NMR spectra of TetraF2W-RK bound to perdeuterated dodecylphosphocholine (DPC-d38) are well dispersed, leading to complete assignments. Based on the $^1$H chemical shifts, a total of 225 NOEs were assigned and converted to distance restraints for structural calculations. The number of NOEs per residue is 28, which is high for a micelle-bound peptide (Chan et al. (2006) Biochim. Biophys. Acta 1758: 1184-1202; Rozek et al. (2000) Biochemistry 39:15765-15774; Schibli et al. (1999) Biochemistry 38:16749-16755). Multiple (i, i+3) and (i, i+4) types of NOEs indicate a helical conformation, consistent with the secondary 1Hα chemical shift analysis. Moreover, peptide backbone dihedral angles derived from a set of heteronuclear chemical shifts also indicate a helical structure (Cornilescu et al. (1999) J. Biomol. NMR 13:289-302). All the distance and angle restraints were utilized for structural calculations. Using an ensemble of 20 energy minimized 3D structures with backbone atoms superimposed, the backbone structure of TetraF2W-RK was found to be well defined (rmsd=0.06 Å). The 3D structure of the peptide consists of a two-turn helix. This can be seen in the Ramachandran plot, where nearly all the backbone angles (φ and φ) are clustered into the helical region. Remarkably, the side chains of the peptide also superimpose well and each Trp side chain is clearly visible. The aromatic rings of three Trp residues (W1, W3, and W8), as well as L4 and I7, occupy the same side, constituting the hydrophobic surface. W2, however, is located between the hydrophilic and hydrophobic interface where it is adjacent to the side chain of K6. R5 is the only side chain that is clearly on the hydrophilic surface. Hence, TetraF2W-RK forms one of the shortest amphipathic helices after binding to membrane-mimetic micelles.

To provide evidence for the binding of the amphipathic helix to the micelles, the water exchange cross peaks of the side chain NH of the four Trp residues was compared. The exchange peak for W2 is strongest, indicating that it was most exposed to water. The exchange cross peaks for W1 and W3 side chains reached 50% of the peak intensity of W2, implying that these two aromatic rings inserted deeper into the micelles. There is no clear cross peak with water for the side chain of W8, implying an even deeper penetration into the micelles. Such a Trp side chain proton exchange picture of the peptide with water is fully consistent with the amphipathic structure of TetraF2W-RK with the hydrophobic side chains buried into the micelles.

There are multiple NOE cross peaks between the aliphatic portion of K6 and the aromatic ring of W2, indicating a possible aromatic-charge interaction. However, it did not appear to matter much whether it is lysine or arginine (Arg) at position 6, because a swap of the positions between R5 and K6, leading to TetraF2W-KR, did not influence bacterial killing efficiency. When all possible dibasic pairs in the same peptide context were compared, the order of *S. aureus* USA300 killing efficiency is RR>RK~KR>KK. This means that arginines at both positions of this peptide template are more effective than lysines in bacterial killing (based on both colony count and membrane permeation experiments). Indeed, the preference of Trp-rich peptides to bind anionic membranes, indicating that these arginines are involved in interaction with anionic phosphatidylglycerols (PGs) (Chan et al. (2006) Biochim. Biophys. Acta 1758:1184-1202; Rozek et al. (2000) Biochemistry 39:15765-15774; Schibli et al. (1999) Biochemistry 38:16749-16755). Direct Arg-PGs contacts between a human cathelicidin LL-37 peptide and dioctanoylphosphatidylglycerol has been observed by intermolecular NOE spectroscopy (Wang, G. (2007) Biochim. Biophys. Acta 1768:3271-3281; Li et al. (2006) J. Am. Chem. Soc., 128:5776-5785; Wang, G. (2008) J. Biol. Chem. 283:32637-32643). Interestingly, the double arginine variant, TetraF2W-RR, is less cytotoxic to human HEK293 and HaCaT cells. It appears that the Arg-Trp combination, frequently observed in Trp-rich peptides, offers an evolutional advantage by optimizing the desired antimicrobial effect and minimizing toxicity to the host.

It was then asked whether insertion of additional arginines to the peptide would be helpful to the peptide in terms of potency and selectivity. For this purpose, six single arginine variants were made based on the above double arginine variant TetraF2W-RR template (wild type WT). The sequences of these peptides are given in Table 8. The quality of these synthetic peptides was confirmed by HPLC chromatograms as well as correct masses. Antimicrobial activities of these peptides were evaluated by the microdilution method as described above using both Gram-negative *Escherichia coli* and Gram-positive *S. aureus* (Table 8). In the case of *E. coli* ATCC 25922, there was a four-fold increase in the minimal inhibitory concentration (MIC) for all the variants, except for the I7R peptide (viz, 17 is substituted by R), which retained the same MIC. When methicillin-resistant *S. aureus* (MRSA) USA300 was tested, a four-fold loss in activity was observed for the W1R, W3R, L4R, and W8R variants compared to the WT (Table 8). However, the anti-MRSA activity of W2R was less reduced, indicating that W2 is less important here than other Trps in the peptide. Interestingly, like the case of *E. coli*, the activity of I7R against *S. aureus* USA300 also remained the same (MIC 3.1 μM).

TABLE 8

Antibacterial and hemolytic effects of TetraF2W-RR (WT) and its single residue variants. C-terminal amidation. SA: *S. aureus* USA300; EC: *E. coli* ATCC 25922; WT: wild type; W1R: residue W1 is replaced by an arginine, and so on; tR, the retention time of a peptide measured on a Waters HPLC system. SEQ ID NOs are in parentheses.

| Name | Peptide Sequence | S. aureus (μM) | E. coli (μM) | HL$_{50}$ (μM) | t$_R$ (min) |
|---|---|---|---|---|---|
| WT | WWWLRRIW (5) | 3.1 | 6.2 | 35 | 12.10 |
| W1R | RWWLRRIW (10) | 12.5 | 25 | >200 | 11.48 |
| W2R | WRWLRRIW (11) | 6.2 | 25 | 100 | 10.86 |
| W3R | WWRLRRIW (12) | 12.5 | 25 | >200 | 10.77 |

TABLE 8-continued

Antibacterial and hemolytic effects of TetraF2W-RR (WT) and its single residue variants. C-terminal amidation. SA: S. aureus USA300; EC: E. coli ATCC 25922; WT: wild type; W1R: residue W1 is replaced by an arginine, and so on; tR, the retention time of a peptide measured on a Waters HPLC system. SEQ ID NOs are in parentheses.

| Name | Peptide Sequence | S. aureus ($\mu$M) | E. coli ($\mu$M) | $HL_{50}$ ($\mu$M) | $t_R$ (min) |
|------|------------------|--------------------|--------------------|----------------------|--------------|
| L4R  | WWWRRRIW (13)    | 12.5               | 25                 | >200                 | 10.78        |
| I7R  | WWWLRRRW (14)    | 3.1                | 6.2                | 150                  | 11.07        |
| W8R  | WWWLRRIR (15)    | 12.5               | 25                 | >200                 | 10.87        |

To further appreciate these activity differences, the growth inhibition as well as membrane permeation power of these peptide variants in Table 8 were compared. I7R is almost equally effective to the WT in inhibiting the growth of *S. aureus* USA300 at 3.1 µM (FIG. 15A). The L4R variant is also potent followed by the W2R peptide. The substitution of W1, W2, or W8, however, made the peptide less inhibitory in this experiment. A similar trend was also observed with membrane permeation by propidium iodide (PI) (FIG. 15B). The WT is most potent followed by the 17R and W2R variants. These results reinforce the significance of aromatic amino acids W1, W3, and W8 in anchoring the peptide to the membranes of *S. aureus USA*300.

In nature, most bacteria live in the biofilm form, and the formation of biofilms makes it more resistant to traditional antibiotics. To further understand the activity of these peptides in Table 8, their ability in disrupting the 24-hour biofilms of *S. aureus* USA300 were compared. After peptide treatment (3.1 to 25 µM), biofilms were stained with either crystal violet (FIGS. 16A-16G) or the XTT-based cell proliferation kit (FIGS. 16H-16N). Crystal violet staining measures the amount of biofilms. When the C-terminal hydrophobic residues were replaced, the peptide variants showed only slightly reduced antibiofilm capability (FIGS. 16E-16G). However, substitution of any of the N-terminal Trp residues (FIGS. 16B-16D) had a detrimental effect on antibiofilm ability, although W2R became more effective at 12.5-25 µM (FIG. 16C). These plots underscore the importance of the N-terminal Trp triplet in disrupting the *S. aureus* biofilms.

Dead bacteria was estimated by using the XTT assay that reports the amount of live cells. At a low concentration of 3.1 µM, none of the peptides were effective. At 6.2 µM, only the WT was active. When the peptide reached 12.5 µM, nearly all *S. aureus* USA300 was eliminated by the WT (FIG. 16H). In addition, the W2R, L4R, I7R, and W8R variants also displayed some effects, with W2R and I7R (80% killing in FIGS. 16J and 16M) being much more effective than L4R and W8R (20% killing in FIGS. 16L and 16N). At 25 µM, these four peptide variants killed nearly all *S. aureus* in the biofilms based on the XTT staining. The stronger effect of the WT may result from its higher hydrophobicity (longest HPLC retention time in Table 8). Notably, neither W1R nor W3R was able to kill the *S. aureus* USA300 strain in the biofilms even at 25 µM, indicating that W1 and W3 are critical in both biofilm disruption and bacterial killing based on a combined use of two biofilm staining dyes (FIG. 16).

The cytotoxicity of these peptides was also compared using human red blood cells. A concentration dependent hemolysis enabled for the estimation of $HL_{50}$, the concentration that causes 50% hemolysis. The results are included in Table 8. Based on $HL_{50}$ and MIC values, the cell selectivity index, which is defined as the ratio of $HL_{50}$ and MIC, was also calculated. While the cell selectivity index for the WT peptide is 35/3.1=11, it is 150/3.1=48 for I7R. Thus, the hemolytic ability of the I7R variant was reduced (Table 8) by four-fold compared to the WT. Therefore, through this structure-activity relationship studies, a more selective peptide, the I7R variant, was obtained that retains antibacterial activity (the same MIC), making it a novel antimicrobials to combat MRSA.

To further verify that the I7R variant remains membrane targeting, a live cell experiment was also conducted by following the entry of a non-membrane permeable dye FITC into *S. aureus* USA300. Only after peptide treatment, green fluorescent bacteria was seen in 28 seconds, indicating membrane permeation by the peptide. To view the dead bacteria directly, the 24 hour preformed biofilms of *S. aureus* USA300 were also treated with the I7R peptide followed by confocal microscopy. Without treatment with the I7R variant, green cells (live) were observed. After treatment, the majority of cells are red, indicating that this peptide killed MRSA in biofilms as well. Similar results were obtained using the WT peptide, indicating I7R, like the WT, killed *S. aureus* USA300 in the biofilms.

The peptide activity (Table 8) was then correlated with the 3D structure. W2, being located in the interface of the amphipathic helix, is less significant for membrane binding, consistent with only a two-fold loss in activity (Table 8). Likewise, 17 is close to the interface and its change to an arginine probably has compensated the loss, leading to the same MIC in Table 8 for both bacteria. These two peptide variants also retained antibiofilm capability similar to the WT (FIGS. 16H-16N). In contrast, residues W1, W3, L4, and W8 are all located on the hydrophobic surface, critical for anchoring the peptide into bacterial membranes. A change of any of these residues into an arginine caused a substantial drop in antibacterial activity (Table 8). The same is true of the biofilm cases, especially when XTT was utilized (FIGS. 16H-16N). It is worthwhile to point out that W1, W3, L4 and W8 are also important for hemolysis since their arginine variants became much less toxic (Table 8).

In the disruption of the MRSA biofilms, however, W1 and W3 of the peptide play an even more critical role than L4 or W8. When samples are stained with crystal violet, there are more biofilms left for the W1R and W3R variants (FIG. 16B, 16D) than for L4R and W8R (FIG. 16E, 16G). Remarkably, the peptide variants of W1 and W3 completely lost their killing ability when stained with XTT (FIG. 16I, 16K), indicating that biofilm disruption based on crystal violet did not entirely reflect bacterial killing based on XTT. Interestingly, the three Trp residues at the N-terminus of TetraF2W-RK of the structure assemble into a π configuration, where W2 is the horizontal bar, while W1 and W3 constitute the two legs critical for interdigitation into the membranes. These aromatic rings of the WWW motif stack with each other. For instance, a cross peaks between W2 and W3 as well as between W1 and W3 can be observed. Also, W1 and W3 are perpendicular to each other, leading to the ring current shifts of multiple protons. It seems that aromatic-aromatic interactions play a role in stabilizing the π-configuration of the WWW structural motif.

In conclusion, the 3D structure for a newly designed Trp-rich peptide (50% Trp) was determined. This structure nicely correlates with antibacterial and antibiofilm activities. It also revealed a novel n-configuration for the Trp triplet stabilized by both aromatic-aromatic and aromatic-aliphatic interactions. This π-configuration of the WWW motif, especially the two legs (W1 and W3), is critical for biofilm disruption and bacterial killing in the biofilms. Such a critical structural motif may be utilized to guide the design of novel peptides. To obtain better peptides, the WWW motif at the N-terminus may be retained by varying the C-terminal residues. The identification of the I7R variant, which retains antimicrobial and antibiofilm activities but with reduced toxicity to human cells, provides an excellent example for this. In addition, the WWW motif can be applied to peptide ends to enhance antimicrobial activity (Schmidtchen et al. (2009) J. Biol. Chem., 284:17584-17594). Collectively, antimicrobial peptides have been identified and a novel n-configuration for a tryptophan triplet has been uncovered via studying the structure-activity relationship of a new Trp-rich peptide that yields novel insight into membrane targeting, MRSA killing, and biofilm disruption.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated peptide comprising the amino acid sequence WWWLX$_1$X$_2$X$_3$W (SEQ ID NO: 17), wherein X$_1$ and X$_2$ are independently Arg or Lys, and wherein X$_3$ is selected from the group consisting of Ile, Arg, and Lys.

2. The isolated peptide of claim 1, wherein X$_1$ and X$_2$ are Arg.

3. The isolated peptide of claim 1, wherein X$_3$ is Arg.

4. The isolated peptide of claim 1, wherein said peptide comprises SEQ ID NO NOs: 2, 3, 4, 5, 6, or 14.

5. The isolated peptide of claim 1, wherein said peptide comprises at least one D-amino acid.

6. The isolated peptide of claim 1, wherein all of the amino acids are D-amino acids.

7. The isolated peptide of claim 1, wherein said peptide comprises at least one modification selected from the group consisting of amidation and acetylation.

8. The isolated peptide of claim 1, wherein said peptide is less than 12 amino acids in length.

9. A composition comprising at least one the peptide of claim 1 and at least one pharmaceutically acceptable carrier.

10. The composition of claim 9, further comprising at least one antibiotic.

11. A method for inhibiting a bacterial infection in a subject in need thereof, said method comprising administering to said subject the peptide of claim 1.

12. The method of claim 11, further comprising the administration of at least one additional antibiotic.

13. The method of claim 11, wherein said bacterial infection is a staphylococcal infection.

14. The method of claim 11, wherein said bacterial infection is a methicillin-resistant *Staphylococcus aureus* (MRSA) infection.

15. The method of claim 11, wherein said peptide is covalently attached to the surface of a medical device or implant.

16. A medical device or implant comprising the peptide of claim 1 covalently attached to the surface of the medical device or implant.

17. The isolated peptide of claim 1, wherein said peptide comprises SEQ ID NO: 14.

18. The isolated peptide of claim 1, wherein said peptide is less than 25 amino acids in length.

19. The isolated peptide of claim 17, wherein said peptide is less than 25 amino acids in length.

20. The isolated peptide of claim 19, wherein said peptide is less than 12 amino acids in length.

21. The isolated peptide of claim 19, wherein said peptide is antibacterial.

22. The isolated peptide of claim 1, wherein said peptide is antibacterial.

23. The isolated peptide of claim 1, wherein said peptide is less than 10 amino acids in length.

24. The isolated peptide of claim 1, consisting of the amino acid sequence WWWLX$_1$X$_2$X$_3$W (SEQ ID NO: 17), wherein X$_1$ and X$_2$ are independently Arg or Lys, and wherein X$_3$ is selected from the group consisting of Ile, Arg, and Lys.

* * * * *

UNITED STATES PATENT AND TRADEMARK OFFICE
CERTIFICATE OF CORRECTION

PATENT NO. : 10,144,767 B2  
APPLICATION NO. : 15/680429  
DATED : December 4, 2018  
INVENTOR(S) : Wang Page 1 of 1

It is certified that error appears in the above-identified patent and that said Letters Patent is hereby corrected as shown below:

On the Title Page

Item (12) delete "Wang" and insert --Wang et al.--  
Item (72) inventor: is corrected to read (72) Inventors: Guangshun Wang, Omaha, NE (US); Biswajit Miahra, Omaha, NE (US)

Signed and Sealed this  
Second Day of April, 2019

Andrei Iancu  
*Director of the United States Patent and Trademark Office*

SEQUENCE LISTING

```
<160> NUMBER OF SEQ ID NOS: 17

<210> SEQ ID NO 1
<211> LENGTH: 8
<212> TYPE: PRT
<213> ORGANISM: Artificial Sequence
<220> FEATURE:
<223> OTHER INFORMATION: TetraF2W

<400> SEQUENCE: 1

Trp Trp Trp Leu Ser Arg Ile Trp
 1               5

<210> SEQ ID NO 2
<211> LENGTH: 8
<212> TYPE: PRT
<213> ORGANISM: Artificial Sequence
<220> FEATURE:
<223> OTHER INFORMATION: TetraF2W-KR

<400> SEQUENCE: 2

Trp Trp Trp Leu Lys Arg Ile Trp
 1               5

<210> SEQ ID NO 3
<211> LENGTH: 8
<212> TYPE: PRT
<213> ORGANISM: Artificial Sequence
<220> FEATURE:
<223> OTHER INFORMATION: TetraF2W-RK

<400> SEQUENCE: 3

Trp Trp Trp Leu Arg Lys Ile Trp
 1               5

<210> SEQ ID NO 4
<211> LENGTH: 8
<212> TYPE: PRT
<213> ORGANISM: Artificial Sequence
<220> FEATURE:
<223> OTHER INFORMATION: TetraF2W-KK

<400> SEQUENCE: 4

Trp Trp Trp Leu Lys Lys Ile Trp
 1               5

<210> SEQ ID NO 5
<211> LENGTH: 8
<212> TYPE: PRT
```

```
<213> ORGANISM: Artificial Sequence
<220> FEATURE:
<223> OTHER INFORMATION: TetraF2W-RR

<400> SEQUENCE: 5

Trp Trp Trp Leu Arg Arg Ile Trp
1               5

<210> SEQ ID NO 6
<211> LENGTH: 8
<212> TYPE: PRT
<213> ORGANISM: Artificial Sequence
<220> FEATURE:
<223> OTHER INFORMATION: TetraF2W-RK-d
<220> FEATURE:
<221> NAME/KEY: VARIANT
<222> LOCATION: (1)...(8)
<223> OTHER INFORMATION: all amino acids are D-amino acids

<400> SEQUENCE: 6

Trp Trp Trp Leu Arg Lys Ile Trp
1               5

<210> SEQ ID NO 7
<211> LENGTH: 8
<212> TYPE: PRT
<213> ORGANISM: Pelophylax saharica

<400> SEQUENCE: 7

Phe Phe Phe Leu Ser Arg Ile Phe
1               5

<210> SEQ ID NO 8
<211> LENGTH: 10
<212> TYPE: PRT
<213> ORGANISM: Artificial Sequence
<220> FEATURE:
<223> OTHER INFORMATION: Tet213

<400> SEQUENCE: 8

Lys Arg Trp Trp Lys Trp Trp Arg Arg Cys
1               5                   10

<210> SEQ ID NO 9
<211> LENGTH: 16
<212> TYPE: PRT
<213> ORGANISM: Artificial Sequence
<220> FEATURE:
<223> OTHER INFORMATION: FK-16

<400> SEQUENCE: 9

Phe Lys Arg Ile Val Gln Arg Ile Lys Asp Phe Leu Arg Asn Leu Val
1               5                   10                  15

<210> SEQ ID NO 10
<211> LENGTH: 8
<212> TYPE: PRT
<213> ORGANISM: Artificial Sequence
<220> FEATURE:
<223> OTHER INFORMATION: W1R

<400> SEQUENCE: 10

Arg Trp Trp Leu Arg Arg Ile Trp
1               5

<210> SEQ ID NO 11
<211> LENGTH: 8
```

```
<212> TYPE: PRT
<213> ORGANISM: Artificial Sequence
<220> FEATURE:
<223> OTHER INFORMATION: W2R

<400> SEQUENCE: 11

Trp Arg Trp Leu Arg Arg Ile Trp
1               5

<210> SEQ ID NO 12
<211> LENGTH: 8
<212> TYPE: PRT
<213> ORGANISM: Artificial Sequence
<220> FEATURE:
<223> OTHER INFORMATION: W3R

<400> SEQUENCE: 12

Trp Trp Arg Leu Arg Arg Ile Trp
1               5

<210> SEQ ID NO 13
<211> LENGTH: 8
<212> TYPE: PRT
<213> ORGANISM: Artificial Sequence
<220> FEATURE:
<223> OTHER INFORMATION: L4R

<400> SEQUENCE: 13

Trp Trp Trp Arg Arg Arg Ile Trp
1               5

<210> SEQ ID NO 14
<211> LENGTH: 8
<212> TYPE: PRT
<213> ORGANISM: Artificial Sequence
<220> FEATURE:
<223> OTHER INFORMATION: I7R

<400> SEQUENCE: 14

Trp Trp Trp Leu Arg Arg Arg Trp
1               5

<210> SEQ ID NO 15
<211> LENGTH: 8
<212> TYPE: PRT
<213> ORGANISM: Artificial Sequence
<220> FEATURE:
<223> OTHER INFORMATION: W8R

<400> SEQUENCE: 15

Trp Trp Trp Leu Arg Arg Ile Arg
1               5

<210> SEQ ID NO 16
<211> LENGTH: 8
<212> TYPE: PRT
<213> ORGANISM: Artificial Sequence
<220> FEATURE:
<223> OTHER INFORMATION: antimicrobial peptide
<220> FEATURE:
<221> NAME/KEY: VARIANT
<222> LOCATION: (4)...(7)
<223> OTHER INFORMATION: Xaa = any amino acid

<400> SEQUENCE: 16

Trp Trp Trp Xaa Xaa Xaa Xaa Trp
1               5
```

```
<210> SEQ ID NO 17
<211> LENGTH: 8
<212> TYPE: PRT
<213> ORGANISM: Artificial Sequence
<220> FEATURE:
<223> OTHER INFORMATION: antimicrobial peptide
<220> FEATURE:
<221> NAME/KEY: VARIANT
<222> LOCATION: (5)...(7)
<223> OTHER INFORMATION: Xaa = any amino acid

<400> SEQUENCE: 17

Trp Trp Trp Leu Xaa Xaa Xaa Trp
 1               5
```